(12) United States Patent
Skillrud et al.

(10) Patent No.: US 10,722,257 B2
(45) Date of Patent: Jul. 28, 2020

(54) RETRIEVAL OF MATERIAL FROM VESSEL LUMENS

(71) Applicant: Covidien LP, Mansfield, MA (US)

(72) Inventors: Erik Skillrud, Newport Beach, CA (US); Daniel Deen, Signal Hill, CA (US); Evan Epstein, Costa Mesa, CA (US)

(73) Assignee: COVIDIEN LP, Mansfield, MA (US)

(*) Notice: Subject to any disclaimer, the term of this patent is extended or adjusted under 35 U.S.C. 154(b) by 331 days.

(21) Appl. No.: 15/594,449

(22) Filed: May 12, 2017

(65) Prior Publication Data

US 2018/0325531 A1  Nov. 15, 2018

(51) Int. Cl.
| | | |
|---|---|---|
| *A61B 17/221* | (2006.01) | |
| *A61B 17/3207* | (2006.01) | |
| *A61F 2/95* | (2013.01) | |
| *A61B 17/22* | (2006.01) | |
| *A61B 17/34* | (2006.01) | |

(52) U.S. Cl.
CPC .. *A61B 17/221* (2013.01); *A61B 2017/22034* (2013.01); *A61B 2017/22094* (2013.01); *A61B 2017/320716* (2013.01); *A61B 2017/3435* (2013.01); *A61F 2/95* (2013.01)

(58) Field of Classification Search
CPC ........... A61B 17/221; A61B 17/0218; A61B 17/00008; A61B 2017/22094; A61B 2017/3435; A61B 2017/22034; A61B 2017/22001; A61B 2017/320741; A61B 2017/22095; A61B 2017/0225; A61B 17/32056; A61B 17/3207; A61B 2017/32073; A61B 17/22031; A61F 2002/016; A61F 2002/018; A61F 2/01
See application file for complete search history.

(56) References Cited

U.S. PATENT DOCUMENTS

| | | |
|---|---|---|
| 2,918,919 A | 12/1959 | Wallace |
| 2,943,626 A | 7/1960 | Dormia |
| 3,996,938 A | 12/1976 | Clark, III |
| 4,347,846 A | 9/1982 | Dormia |
| 4,611,594 A | 9/1986 | Grayhack et al. |
| 4,650,466 A | 3/1987 | Luther |
| 4,657,020 A | 4/1987 | Lifton |
| 4,699,147 A | 10/1987 | Chilson et al. |

(Continued)

FOREIGN PATENT DOCUMENTS

| | | |
|---|---|---|
| CN | 1640505 A | 7/2005 |
| CN | 102036611 A | 4/2011 |

(Continued)

*Primary Examiner* — Elizabeth Houston
*Assistant Examiner* — Michael G Mendoza
(74) *Attorney, Agent, or Firm* — Fortem IP LLP; Vijay Kumar

(57) ABSTRACT

Devices for removing clot material from a blood vessel lumen and associated systems and methods are disclosed herein. A clot retrieving device may include, for example, an elongated shaft, a capture structure having a proximal region coupled to the distal zone of the elongated shaft, a cover, and a connector coupling the cover to the distal zone of the elongated shaft. The device may further include a jacket at least partially over the proximal terminus of the connector and a portion of the filaments protruding from the connector.

26 Claims, 21 Drawing Sheets

(56) References Cited

U.S. PATENT DOCUMENTS

| | | |
|---|---|---|
| 4,790,812 A | 12/1988 | Hawkins, Jr. et al. |
| 4,807,626 A | 2/1989 | McGirr |
| 4,832,055 A | 5/1989 | Palestrant |
| 4,873,978 A | 10/1989 | Ginsburg |
| 4,969,891 A | 11/1990 | Gewertz |
| 4,998,539 A | 3/1991 | Delsanti |
| 5,034,001 A | 7/1991 | Garrison et al. |
| 5,057,114 A | 10/1991 | Wittich et al. |
| 5,059,178 A | 10/1991 | Ya |
| 5,102,415 A | 4/1992 | Guenther et al. |
| 5,147,400 A | 9/1992 | Kaplan et al. |
| 5,152,777 A | 10/1992 | Goldberg et al. |
| 5,192,286 A | 3/1993 | Phan et al. |
| 5,300,086 A | 4/1994 | Gory et al. |
| 5,329,942 A | 7/1994 | Gunther et al. |
| 5,443,478 A | 8/1995 | Purdy |
| 5,449,372 A | 9/1995 | Schmaltz et al. |
| 5,458,375 A | 10/1995 | Anspach, Jr. et al. |
| 5,490,859 A | 2/1996 | Mische et al. |
| 5,496,330 A | 3/1996 | Bates et al. |
| 5,509,900 A | 4/1996 | Kirkman |
| 5,653,684 A | 8/1997 | Laptewicz et al. |
| 5,658,296 A | 8/1997 | Bates et al. |
| 5,709,704 A | 1/1998 | Nott et al. |
| 5,733,302 A | 3/1998 | Myler et al. |
| 5,741,325 A | 4/1998 | Chaikof et al. |
| 5,792,156 A | 8/1998 | Perouse |
| 5,827,324 A | 10/1998 | Cassell et al. |
| 5,846,251 A | 12/1998 | Hart |
| 5,895,398 A | 4/1999 | Wensel et al. |
| 5,941,869 A | 8/1999 | Patterson et al. |
| 5,947,995 A | 9/1999 | Samuels |
| 5,968,090 A | 10/1999 | Ratcliff et al. |
| 5,971,938 A | 10/1999 | Hart et al. |
| 5,972,019 A | 10/1999 | Engelson et al. |
| 5,984,957 A | 11/1999 | Laptewicz, Jr. et al. |
| 6,001,118 A | 12/1999 | Daniel et al. |
| 6,033,394 A | 3/2000 | Vidlund et al. |
| 6,042,598 A | 3/2000 | Tsugita et al. |
| 6,053,932 A | 4/2000 | Daniel et al. |
| 6,066,149 A | 5/2000 | Samson et al. |
| 6,066,158 A | 5/2000 | Engelson et al. |
| 6,096,053 A | 8/2000 | Bates |
| 6,099,534 A | 8/2000 | Bates et al. |
| 6,146,403 A | 11/2000 | St. Germain |
| 6,159,220 A | 12/2000 | Gobron et al. |
| 6,165,200 A | 12/2000 | Tsugita et al. |
| 6,168,603 B1 | 1/2001 | Leslie et al. |
| 6,174,318 B1 | 1/2001 | Bates et al. |
| 6,176,873 B1 | 1/2001 | Ouchi |
| 6,190,394 B1 | 2/2001 | Lind et al. |
| 6,217,609 B1 | 4/2001 | Haverkost |
| 6,221,006 B1 | 4/2001 | Dubrul et al. |
| 6,245,088 B1 | 6/2001 | Lowery |
| 6,245,089 B1 | 6/2001 | Daniel et al. |
| 6,248,113 B1 | 6/2001 | Fina |
| 6,264,664 B1 | 7/2001 | Avellanet |
| 6,302,895 B1 | 10/2001 | Gobron et al. |
| 6,309,399 B1 | 10/2001 | Barbut et al. |
| 6,348,056 B1 | 2/2002 | Bates et al. |
| 6,350,266 B1 | 2/2002 | White et al. |
| 6,364,895 B1 | 4/2002 | Greenhalgh |
| 6,371,971 B1 | 4/2002 | Tsugita et al. |
| 6,383,195 B1 | 5/2002 | Richard |
| 6,383,196 B1 | 5/2002 | Leslie et al. |
| 6,391,044 B1 | 5/2002 | Yadav et al. |
| 6,402,771 B1 | 6/2002 | Palmer et al. |
| 6,409,750 B1 | 6/2002 | Hyodoh et al. |
| 6,416,505 B1 | 7/2002 | Fleischman et al. |
| 6,425,909 B1 | 7/2002 | Dieck et al. |
| 6,436,112 B2 | 8/2002 | Wensel et al. |
| 6,443,972 B1 | 9/2002 | Bosma et al. |
| 6,458,139 B1 | 10/2002 | Palmer et al. |
| 6,485,497 B2 | 11/2002 | Wensel et al. |
| 6,494,884 B2 | 12/2002 | Gifford, III et al. |
| 6,506,204 B2 | 1/2003 | Mazzocchi |
| 6,514,273 B1 | 2/2003 | Voss et al. |
| 6,530,935 B2 | 3/2003 | Wensel et al. |
| 6,540,657 B2 | 4/2003 | Cross, III et al. |
| 6,540,768 B1 | 4/2003 | Diaz et al. |
| 6,551,342 B1 | 4/2003 | Shen et al. |
| 6,575,997 B1 | 6/2003 | Palmer et al. |
| 6,585,753 B2 | 7/2003 | Eder et al. |
| 6,592,605 B2 | 7/2003 | Lenker et al. |
| 6,592,607 B1 | 7/2003 | Palmer et al. |
| 6,602,271 B2 | 8/2003 | Adams et al. |
| 6,605,102 B1 | 8/2003 | Mazzocchi et al. |
| 6,610,077 B1 | 8/2003 | Hancock et al. |
| 6,616,679 B1 | 9/2003 | Khosravi et al. |
| 6,620,148 B1 | 9/2003 | Tsugita |
| 6,635,068 B1 | 10/2003 | Dubrul et al. |
| 6,636,758 B2 | 10/2003 | Sanchez et al. |
| 6,638,245 B2 | 10/2003 | Miller et al. |
| 6,638,293 B1 | 10/2003 | Makower et al. |
| 6,641,590 B1 | 11/2003 | Palmer et al. |
| 6,645,199 B1 | 11/2003 | Jenkins et al. |
| 6,652,505 B1 | 11/2003 | Tsugita |
| 6,652,548 B2 | 11/2003 | Evans et al. |
| 6,660,021 B1 | 12/2003 | Palmer et al. |
| 6,663,650 B2 | 12/2003 | Sepetka et al. |
| 6,673,042 B1 | 1/2004 | Samson et al. |
| 6,679,893 B1 | 1/2004 | Tran |
| 6,685,738 B2 | 2/2004 | Chouinard et al. |
| 6,692,508 B2 | 2/2004 | Wensel et al. |
| 6,692,509 B2 | 2/2004 | Wensel et al. |
| 6,695,858 B1 | 2/2004 | Dubrul et al. |
| 6,702,782 B2 | 3/2004 | Miller et al. |
| 6,730,104 B1 | 5/2004 | Sepetka et al. |
| 6,745,080 B2 | 6/2004 | Koblish |
| 6,746,468 B1 | 6/2004 | Sepetka et al. |
| 6,749,619 B2 | 6/2004 | Ouriel et al. |
| 6,755,813 B2 | 6/2004 | Ouriel et al. |
| 6,800,080 B1 | 10/2004 | Bates |
| 6,824,545 B2 | 11/2004 | Sepetka et al. |
| 6,855,155 B2 | 2/2005 | Denardo et al. |
| 6,872,211 B2 | 3/2005 | White et al. |
| 6,872,216 B2 | 3/2005 | Daniel et al. |
| 6,890,341 B2 | 5/2005 | Dieck et al. |
| 6,893,431 B2 | 5/2005 | Naimark et al. |
| 6,905,503 B2 | 6/2005 | Gifford, III et al. |
| 6,913,612 B2 | 7/2005 | Palmer et al. |
| 6,936,059 B2 | 8/2005 | Belef |
| 6,939,362 B2 | 9/2005 | Boyle et al. |
| 6,945,977 B2 | 9/2005 | Demarais et al. |
| 6,953,465 B2 | 10/2005 | Dieck et al. |
| 6,964,672 B2 | 11/2005 | Brady et al. |
| 7,004,955 B2 | 2/2006 | Shen et al. |
| 7,004,956 B2 | 2/2006 | Palmer et al. |
| 7,037,320 B2 | 5/2006 | Brady et al. |
| 7,041,126 B2 | 5/2006 | Shin et al. |
| 7,048,014 B2 | 5/2006 | Hyodoh et al. |
| 7,058,456 B2 | 6/2006 | Pierce |
| 7,097,653 B2 | 8/2006 | Freudenthal et al. |
| 7,101,380 B2 | 9/2006 | Khachin et al. |
| 7,169,165 B2 | 1/2007 | Belef et al. |
| 7,179,273 B1 | 2/2007 | Palmer et al. |
| 7,182,771 B1 | 2/2007 | Houser et al. |
| 7,235,061 B2 | 6/2007 | Tsugita |
| 7,240,516 B2 | 7/2007 | Pryor |
| 7,399,308 B2 | 7/2008 | Borillo et al. |
| 7,534,252 B2 | 5/2009 | Sepetka et al. |
| 7,578,830 B2 | 8/2009 | Kusleika et al. |
| 7,621,870 B2 | 11/2009 | Berrada et al. |
| 7,837,702 B2 | 11/2010 | Bates |
| 8,070,791 B2 | 12/2011 | Ferrera et al. |
| 8,088,140 B2 | 1/2012 | Ferrera et al. |
| 8,105,333 B2 | 1/2012 | Sepetka et al. |
| 8,197,493 B2 | 6/2012 | Ferrera et al. |
| 8,603,014 B2 | 12/2013 | Alleman et al. |
| 8,837,800 B1 | 9/2014 | Bammer et al. |
| 9,119,656 B2 | 9/2015 | Bose et al. |
| 9,126,018 B1 | 9/2015 | Garrison |
| 9,211,132 B2 | 12/2015 | Bowman |
| 9,241,699 B1 | 1/2016 | Kume et al. |

(56) References Cited

U.S. PATENT DOCUMENTS

| | | |
|---|---|---|
| 9,265,512 B2 | 2/2016 | Garrison et al. |
| 9,308,007 B2 | 4/2016 | Cully et al. |
| 9,399,118 B2 | 7/2016 | Kume et al. |
| 9,445,828 B2 | 9/2016 | Turjman et al. |
| 9,445,829 B2 | 9/2016 | Brady et al. |
| 9,492,637 B2 | 11/2016 | Garrison et al. |
| 9,539,022 B2 | 1/2017 | Bowman |
| 9,561,345 B2 | 2/2017 | Garrison et al. |
| 9,579,119 B2 | 2/2017 | Cully et al. |
| 9,585,741 B2 | 3/2017 | Ma |
| 9,642,635 B2 | 5/2017 | Vale et al. |
| 9,655,633 B2 | 5/2017 | Leynov et al. |
| 9,737,318 B2 | 8/2017 | Monstadt et al. |
| 9,770,251 B2 | 9/2017 | Bowman et al. |
| 9,801,643 B2 | 10/2017 | Hansen et al. |
| 9,861,783 B2 | 1/2018 | Garrison et al. |
| 9,993,257 B2 | 6/2018 | Losordo et al. |
| 10,028,782 B2 | 7/2018 | Orion |
| 10,029,008 B2 | 7/2018 | Creighton |
| 10,039,906 B2 | 8/2018 | Kume et al. |
| 2001/0041909 A1 | 11/2001 | Tsugita et al. |
| 2001/0044632 A1 | 11/2001 | Daniel et al. |
| 2001/0044634 A1 | 11/2001 | Don Michael et al. |
| 2001/0051810 A1 | 12/2001 | Dubrul et al. |
| 2002/0002396 A1 | 1/2002 | Fulkerson |
| 2002/0004667 A1 | 1/2002 | Adams et al. |
| 2002/0026211 A1 | 2/2002 | Khosravi et al. |
| 2002/0058904 A1 | 5/2002 | Boock et al. |
| 2002/0062135 A1 | 5/2002 | Mazzocchi et al. |
| 2002/0072764 A1 | 6/2002 | Sepetka et al. |
| 2002/0082558 A1 | 6/2002 | Samson et al. |
| 2002/0123765 A1 | 9/2002 | Sepetka et al. |
| 2002/0138094 A1 | 9/2002 | Borillo et al. |
| 2002/0151928 A1 | 10/2002 | Leslie et al. |
| 2002/0169474 A1 | 11/2002 | Kusleika et al. |
| 2002/0188314 A1 | 12/2002 | Anderson et al. |
| 2002/0193825 A1 | 12/2002 | McGuckin et al. |
| 2003/0004542 A1 | 1/2003 | Wensel et al. |
| 2003/0023265 A1 | 1/2003 | Forber |
| 2003/0040771 A1 | 2/2003 | Hyodoh et al. |
| 2003/0050663 A1 | 3/2003 | Khachin et al. |
| 2003/0060782 A1 | 3/2003 | Bose et al. |
| 2003/0093087 A1 | 5/2003 | Jones et al. |
| 2003/0144687 A1 | 7/2003 | Brady et al. |
| 2003/0153935 A1 | 8/2003 | Mialhe |
| 2003/0171771 A1 | 9/2003 | Anderson et al. |
| 2003/0176884 A1 | 9/2003 | Berrada et al. |
| 2003/0195556 A1 | 10/2003 | Stack et al. |
| 2004/0068288 A1 | 4/2004 | Palmer et al. |
| 2004/0073243 A1 | 4/2004 | Sepetka et al. |
| 2004/0079429 A1 | 4/2004 | Miller et al. |
| 2004/0133232 A1 | 7/2004 | Rosenbluth et al. |
| 2004/0138692 A1 | 7/2004 | Phung et al. |
| 2004/0153025 A1 | 8/2004 | Seifert et al. |
| 2004/0153118 A1 | 8/2004 | Clubb et al. |
| 2004/0172056 A1 | 9/2004 | Guterman et al. |
| 2004/0199201 A1 | 10/2004 | Kellett et al. |
| 2004/0199243 A1 | 10/2004 | Yodfat |
| 2004/0210116 A1 | 10/2004 | Nakao |
| 2004/0267301 A1 | 12/2004 | Boylan et al. |
| 2005/0004594 A1 | 1/2005 | Nool et al. |
| 2005/0033348 A1 | 2/2005 | Sepetka et al. |
| 2005/0038447 A1 | 2/2005 | Huffmaster |
| 2005/0043680 A1 | 2/2005 | Segal et al. |
| 2005/0043756 A1 | 2/2005 | Lavelle et al. |
| 2005/0049619 A1 | 3/2005 | Sepetka et al. |
| 2005/0055033 A1 | 3/2005 | Leslie et al. |
| 2005/0055047 A1 | 3/2005 | Greenhalgh |
| 2005/0059995 A1 | 3/2005 | Sepetka et al. |
| 2005/0080356 A1 | 4/2005 | Dapolito et al. |
| 2005/0085826 A1 | 4/2005 | Nair et al. |
| 2005/0085847 A1 | 4/2005 | Galdonik et al. |
| 2005/0085849 A1 | 4/2005 | Sepetka et al. |
| 2005/0090857 A1 | 4/2005 | Kusleika et al. |
| 2005/0090858 A1 | 4/2005 | Pavlovic |
| 2005/0125024 A1 | 6/2005 | Sepetka et al. |
| 2005/0131450 A1 | 6/2005 | Nicholson et al. |
| 2005/0171566 A1 | 8/2005 | Kanamaru |
| 2005/0203571 A1 | 9/2005 | Mazzocchi et al. |
| 2005/0209609 A1 | 9/2005 | Wallace |
| 2005/0216030 A1 | 9/2005 | Sepetka et al. |
| 2005/0216050 A1 | 9/2005 | Sepetka et al. |
| 2005/0234501 A1 | 10/2005 | Barone |
| 2005/0234505 A1 | 10/2005 | Diaz et al. |
| 2005/0277978 A1 | 12/2005 | Greenhalgh |
| 2005/0283166 A1 | 12/2005 | Greenhalgh |
| 2005/0283186 A1 | 12/2005 | Berrada et al. |
| 2006/0004404 A1 | 1/2006 | Khachin et al. |
| 2006/0009784 A1 | 1/2006 | Behl et al. |
| 2006/0030925 A1 | 2/2006 | Pryor |
| 2006/0047286 A1 | 3/2006 | West |
| 2006/0058836 A1 | 3/2006 | Bose et al. |
| 2006/0058837 A1 | 3/2006 | Bose et al. |
| 2006/0058838 A1 | 3/2006 | Bose et al. |
| 2006/0095070 A1 | 5/2006 | Gilson et al. |
| 2006/0129166 A1 | 6/2006 | Lavelle |
| 2006/0129180 A1 | 6/2006 | Tsugita et al. |
| 2006/0155305 A1 | 7/2006 | Freudenthal et al. |
| 2006/0190070 A1 | 8/2006 | Dieck et al. |
| 2006/0195137 A1 | 8/2006 | Sepetka et al. |
| 2006/0229638 A1 | 10/2006 | Abrams et al. |
| 2006/0253145 A1 | 11/2006 | Lucas |
| 2006/0271153 A1 | 11/2006 | Garcia et al. |
| 2006/0276805 A1 | 12/2006 | Yu |
| 2006/0282111 A1 | 12/2006 | Morsi |
| 2006/0287668 A1 | 12/2006 | Fawzi et al. |
| 2007/0112374 A1 | 5/2007 | Paul et al. |
| 2007/0118165 A1 | 5/2007 | DeMello et al. |
| 2007/0149996 A1 | 6/2007 | Coughlin |
| 2007/0185500 A1 | 8/2007 | Martin et al. |
| 2007/0185501 A1 | 8/2007 | Martin et al. |
| 2007/0197103 A1 | 8/2007 | Martin et al. |
| 2007/0198029 A1 | 8/2007 | Martin et al. |
| 2007/0198030 A1 | 8/2007 | Martin et al. |
| 2007/0198051 A1 | 8/2007 | Clubb et al. |
| 2007/0225749 A1 | 9/2007 | Martin et al. |
| 2007/0233236 A1 | 10/2007 | Pryor |
| 2007/0265656 A1 | 11/2007 | Amplatz et al. |
| 2008/0109031 A1 | 5/2008 | Sepetka et al. |
| 2008/0183198 A1 | 7/2008 | Sepetka et al. |
| 2008/0188885 A1 | 8/2008 | Sepetka et al. |
| 2008/0262528 A1 | 10/2008 | Martin |
| 2008/0262532 A1 | 10/2008 | Martin |
| 2009/0069828 A1 | 3/2009 | Martin et al. |
| 2009/0105722 A1 | 4/2009 | Fulkerson et al. |
| 2009/0105737 A1 | 4/2009 | Fulkerson et al. |
| 2009/0125053 A1 | 5/2009 | Ferrera et al. |
| 2009/0192518 A1 | 7/2009 | Golden et al. |
| 2009/0287291 A1 | 11/2009 | Becking et al. |
| 2009/0299393 A1 | 12/2009 | Martin et al. |
| 2010/0076452 A1 | 3/2010 | Sepetka et al. |
| 2010/0100106 A1 | 4/2010 | Ferrera |
| 2010/0174309 A1 | 7/2010 | Fulkerson et al. |
| 2010/0185210 A1 | 7/2010 | Hauser et al. |
| 2010/0217187 A1 | 8/2010 | Fulkerson et al. |
| 2010/0256600 A1 | 10/2010 | Ferrera |
| 2010/0318097 A1 | 12/2010 | Ferrera et al. |
| 2011/0152823 A1* | 6/2011 | Mohiuddin .......... A61B 17/221 604/500 |
| 2011/0160742 A1 | 6/2011 | Ferrera et al. |
| 2011/0160757 A1 | 6/2011 | Ferrera et al. |
| 2011/0160760 A1 | 6/2011 | Ferrera et al. |
| 2011/0160761 A1 | 6/2011 | Ferrera et al. |
| 2011/0160763 A1 | 6/2011 | Ferrera et al. |
| 2011/0166586 A1 | 7/2011 | Sepetka et al. |
| 2011/0288572 A1 | 11/2011 | Martin |
| 2011/0319917 A1 | 12/2011 | Ferrera et al. |
| 2012/0143230 A1 | 6/2012 | Sepetka et al. |
| 2012/0197285 A1 | 8/2012 | Martin et al. |
| 2013/0030461 A1 | 1/2013 | Marks et al. |
| 2013/0281788 A1 | 10/2013 | Garrison |
| 2013/0317589 A1 | 11/2013 | Martin et al. |
| 2014/0276074 A1 | 9/2014 | Warner |

(56) References Cited

U.S. PATENT DOCUMENTS

| | | |
|---|---|---|
| 2014/0276403 A1* | 9/2014 | Follmer .......... A61B 17/22032 604/103.02 |
| 2014/0343595 A1 | 11/2014 | Monstadt et al. |
| 2015/0359547 A1 | 12/2015 | Vale et al. |
| 2016/0015402 A1 | 1/2016 | Brady et al. |
| 2016/0015935 A1 | 1/2016 | Chan et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113665 A1 | 4/2016 | Brady et al. |
| 2016/0151618 A1 | 6/2016 | Powers et al. |
| 2016/0157985 A1 | 6/2016 | Vo et al. |
| 2016/0199620 A1 | 7/2016 | Pokorney et al. |
| 2016/0296690 A1 | 10/2016 | Kume et al. |
| 2016/0302808 A1 | 10/2016 | Loganathan et al. |
| 2016/0354098 A1 | 12/2016 | Martin et al. |
| 2016/0375180 A1 | 12/2016 | Anzai |
| 2017/0020542 A1 | 1/2017 | Martin et al. |
| 2017/0079766 A1 | 3/2017 | Wang et al. |
| 2017/0079767 A1 | 3/2017 | Leon-Yip |
| 2017/0086862 A1 | 3/2017 | Vale et al. |
| 2017/0100143 A1 | 4/2017 | Grandfield |
| 2017/0105743 A1 | 4/2017 | Vale et al. |
| 2017/0164963 A1 | 6/2017 | Goyal |
| 2017/0215902 A1 | 8/2017 | Leynov et al. |
| 2017/0224953 A1 | 8/2017 | Tran et al. |
| 2017/0281909 A1 | 10/2017 | Northrop et al. |
| 2017/0290599 A1 | 10/2017 | Youn et al. |
| 2018/0049762 A1 | 2/2018 | Seip et al. |
| 2018/0084982 A1 | 3/2018 | Yamashita et al. |
| 2018/0116717 A1 | 5/2018 | Taff et al. |
| 2018/0132876 A1 | 5/2018 | Zaidat |
| 2018/0140314 A1 | 5/2018 | Goyal et al. |
| 2018/0140315 A1 | 5/2018 | Bowman et al. |
| 2018/0140354 A1 | 5/2018 | Lam et al. |
| 2018/0185614 A1 | 7/2018 | Garrison et al. |

FOREIGN PATENT DOCUMENTS

| | | |
|---|---|---|
| DE | 3501707 A1 | 7/1986 |
| EP | 200688 A2 | 11/1986 |
| EP | 1312314 A1 | 5/2003 |
| EP | 2319575 B1 | 11/2013 |
| JP | 2002537943 A | 11/2002 |
| JP | 2007-522881 A | 8/2007 |
| JP | 2007252951 A | 10/2007 |
| JP | 2008539958 A | 11/2008 |
| JP | 2011508635 | 3/2011 |
| JP | 2014004219 A | 1/2014 |
| JP | 2018118132 A | 8/2018 |
| KR | 20180102877 A | 9/2018 |
| WO | WO-94/09845 A1 | 5/1994 |
| WO | WO-95/09586 A1 | 4/1995 |
| WO | WO-9601591 A1 | 1/1996 |
| WO | WO-96/17634 A2 | 6/1996 |
| WO | WO-96/19941 A1 | 7/1996 |
| WO | WO-97/27808 A1 | 8/1997 |
| WO | WO-97/27893 A1 | 8/1997 |
| WO | WO-98/03120 A1 | 1/1998 |
| WO | WO-00/53120 A1 | 9/2000 |
| WO | WO-0072909 A1 | 12/2000 |
| WO | WO-01/32254 A1 | 5/2001 |
| WO | WO-01/54622 A1 | 8/2001 |
| WO | WO-01/67967 A1 | 9/2001 |
| WO | WO-02/02162 | 1/2002 |
| WO | WO-02/28291 A2 | 4/2002 |
| WO | WO-03/000334 A1 | 1/2003 |
| WO | WO-03/061730 A2 | 7/2003 |
| WO | WO-03/089039 A1 | 10/2003 |
| WO | WO-2006/031410 A2 | 3/2006 |
| WO | WO-2006/122076 A1 | 11/2006 |
| WO | WO-2007092820 A2 | 8/2007 |
| WO | WO-2008/036156 A1 | 3/2008 |
| WO | WO-2008036156 | 3/2008 |
| WO | WO-2008/131116 A1 | 10/2008 |
| WO | WO-2009/034456 A2 | 3/2009 |
| WO | WO-2009/086482 A1 | 7/2009 |
| WO | WO-2011/091383 A1 | 7/2011 |
| WO | WO-2011091383 | 7/2011 |
| WO | WO-2012009675 A2 | 1/2012 |
| WO | WO-2012/162437 A1 | 11/2012 |
| WO | WO-2013/106146 A1 | 7/2013 |
| WO | 2015141317 A1 | 9/2015 |
| WO | 2017192999 A1 | 11/2017 |
| WO | 2018019829 A1 | 2/2018 |
| WO | 2018033401 A1 | 2/2018 |
| WO | 2018046408 A2 | 3/2018 |
| WO | 2018137029 A1 | 8/2018 |
| WO | 2018137030 A1 | 8/2018 |
| WO | 2018145212 A1 | 8/2018 |
| WO | 2018156813 A1 | 8/2018 |
| WO | 2018172891 A1 | 9/2018 |
| WO | 2018187776 A1 | 10/2018 |

* cited by examiner

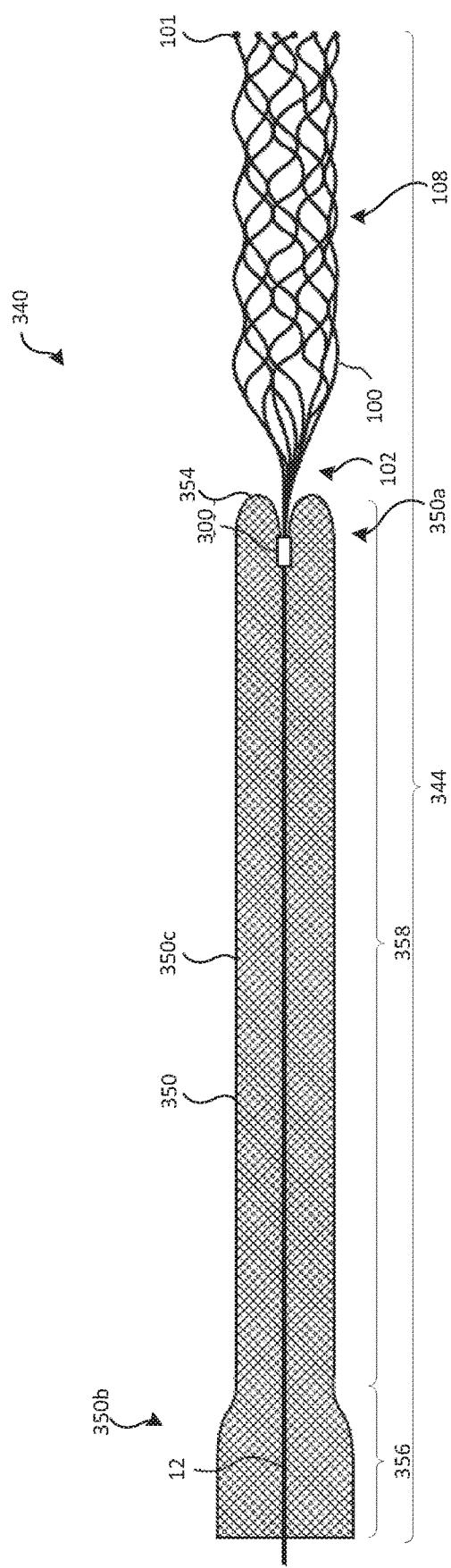
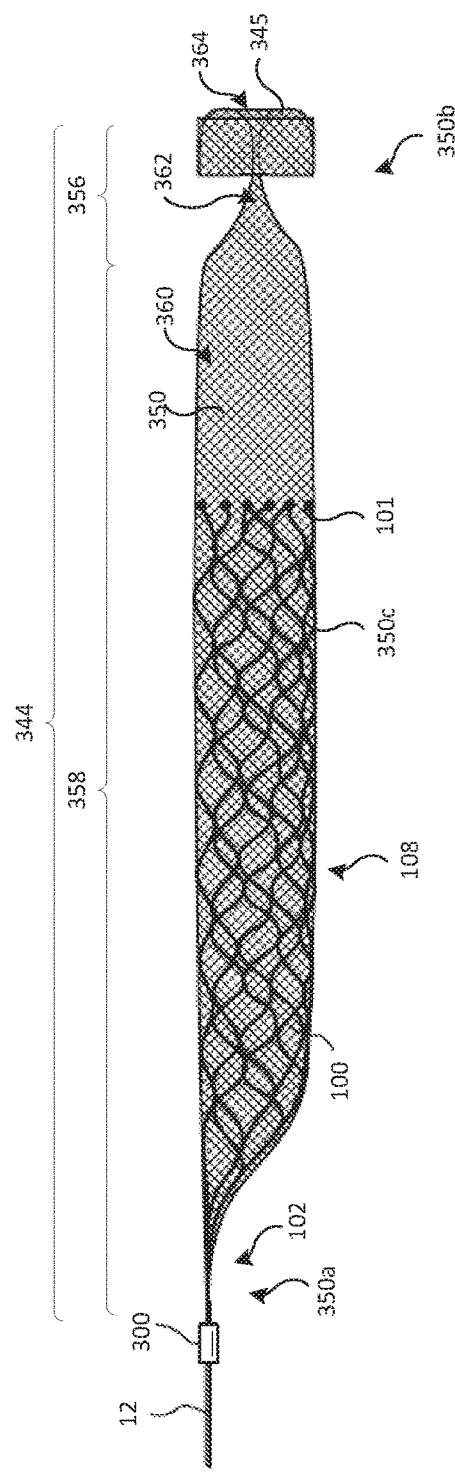
FIG. 3A
FIG. 3B

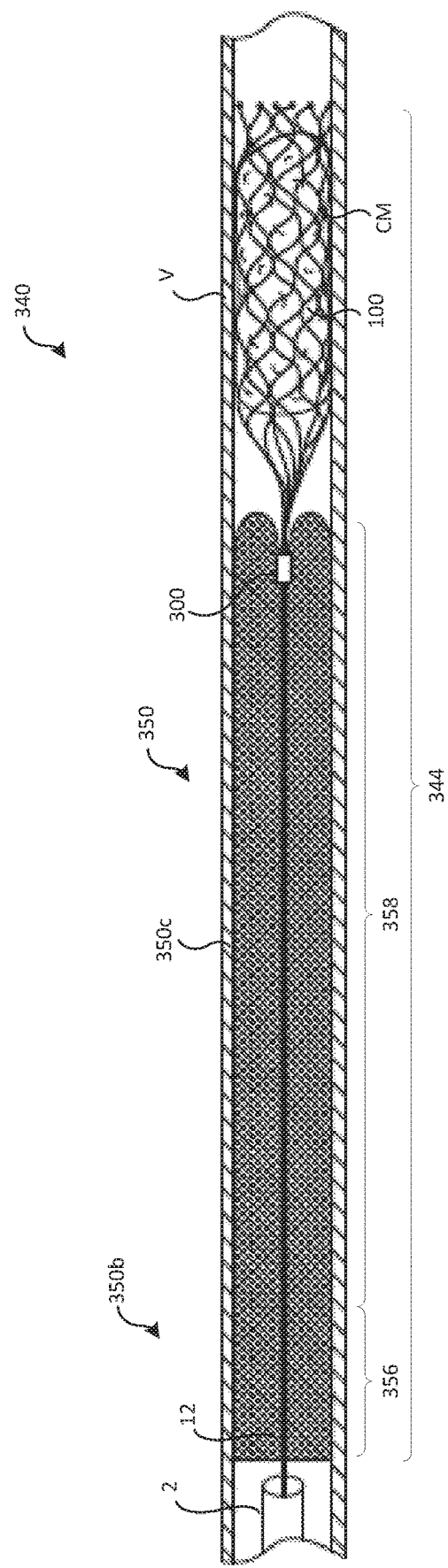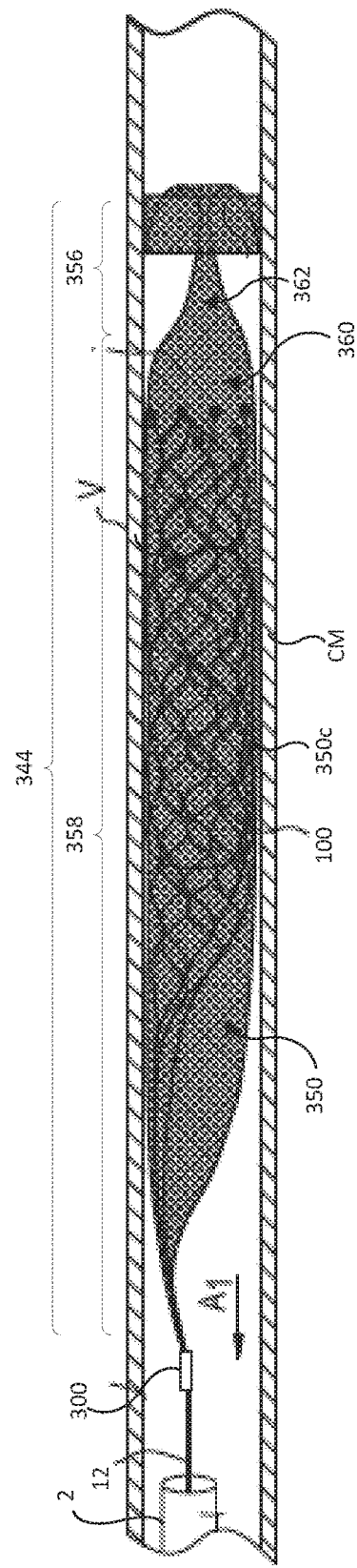
FIG. 5A
FIG. 5B

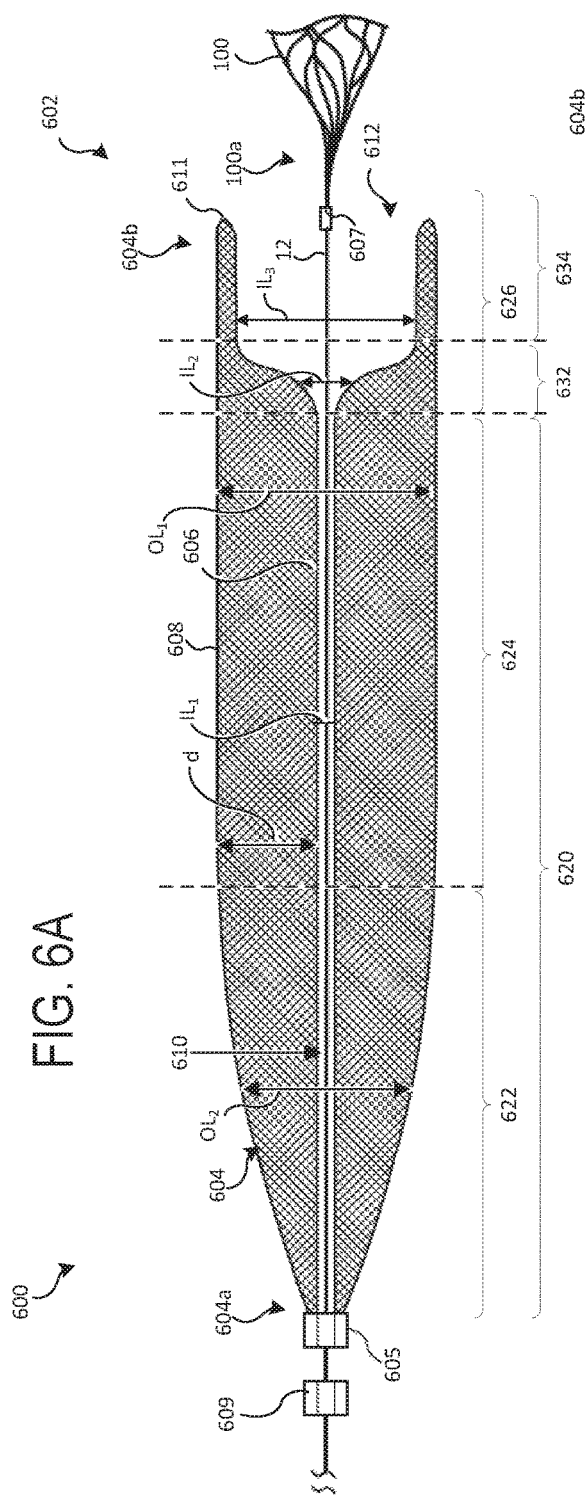
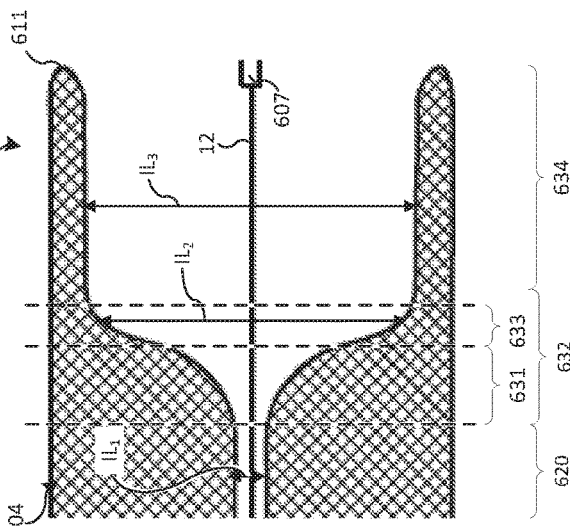
FIG. 6A
FIG. 6B

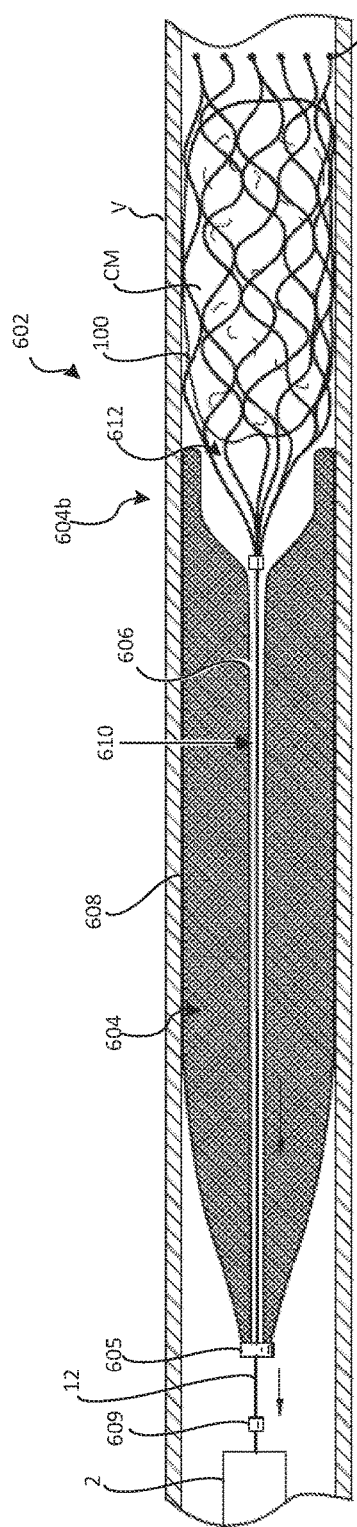
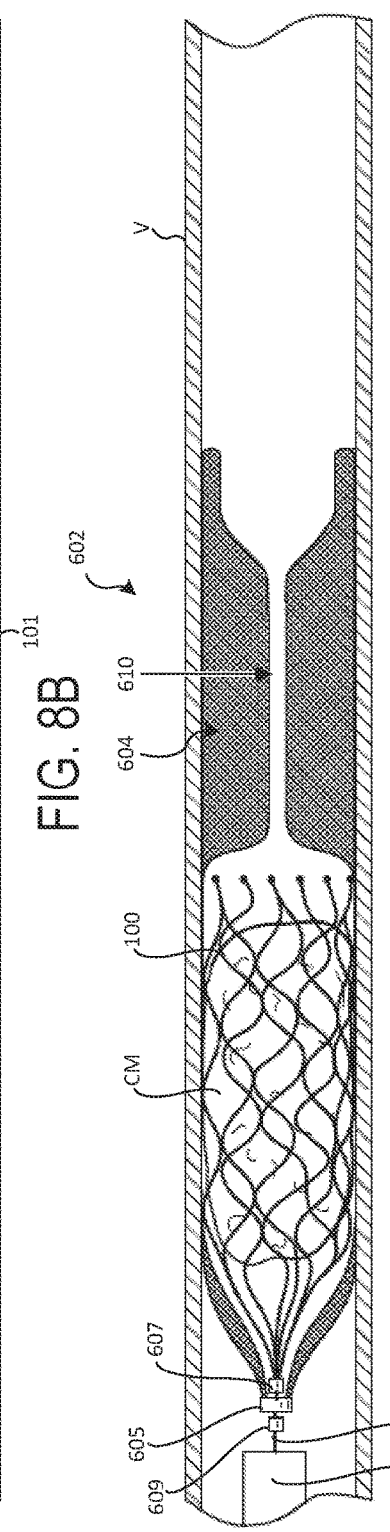
FIG. 8A
FIG. 8B
FIG. 8C

RETRIEVAL OF MATERIAL FROM VESSEL LUMENS

TECHNICAL FIELD

The present technology relates generally to devices and methods for removing obstructions from body lumens. Some embodiments of the present technology relate to devices and methods for removing clot material from blood vessels.

BACKGROUND

Many medical procedures use medical device(s) to remove an obstruction (such as clot material) from a body lumen, vessel, or other organ. An inherent risk in such procedures is that mobilizing or otherwise disturbing the obstruction can potentially create further harm if the obstruction or a fragment thereof dislodges from the retrieval device. If all or a portion of the obstruction breaks free from the device and flows downstream, it is highly likely that the free material will become trapped in smaller and more tortuous anatomy. In many cases, the physician will no longer be able to use the same retrieval device to again remove the obstruction because the device may be too large and/or immobile to move the device to the site of the new obstruction.

Even in successful procedures, a physician must be cautious to prevent the walls of the vessel or body lumen from imparting undesired forces to shear or dislodge the obstruction as it passes through the vasculature during removal. These forces have the potential of fragmenting the obstruction. In some cases, the obstruction can simply break free from the retrieval device and can lodge in a new area causing more concern than the original blockage.

Procedures for treating ischemic stroke by restoring flow within the cerebral vasculature are subject to the above concerns. The brain relies on its arteries and veins to supply oxygenated blood from the heart and lungs and to remove carbon dioxide and cellular waste from brain tissue. Blockages that interfere with this blood supply eventually cause the brain tissue to stop functioning. If the disruption in blood occurs for a sufficient amount of time, the continued lack of nutrients and oxygen causes irreversible cell death (infarction). Accordingly, it is desirable to provide immediate medical treatment of an ischemic stroke. To access the cerebral vasculature, a physician typically advances a catheter from a remote part of the body (typically a leg) through the abdominal vasculature and into the cerebral region of the vasculature. Once within the cerebral vasculature, the physician deploys a device for retrieval of the obstruction causing the blockage. Concerns about dislodged obstructions or the migration of dislodged fragments increases the duration of the procedure at time when restoration of blood flow is paramount. Furthermore, a physician might be unaware of one or more fragments that dislodge from the initial obstruction and cause blockage of smaller more distal vessels.

Many physicians currently perform thrombectomies (i.e. clot removal) with stents to resolve ischemic stroke. Typically, the physician deploys a stent into the clot in an attempt to push the clot to the side of the vessel and re-establish blood flow. Tissue plasminogen activator ("tPA") is often injected into the bloodstream through an intravenous line to break down a clot. However, it takes time for the tPA to reach the clot because the tPA must travel through the vasculature and only begins to break up the clot once it reaches the clot material. tPA is also often administered to supplement the effectiveness of the stent. Yet, if attempts at clot dissolution are ineffective or incomplete, the physician can attempt to remove the stent while it is expanded against or enmeshed within the clot. In doing so, the physician must effectively drag the clot through the vasculature, in a proximal direction, into a guide catheter located within vessels in the patients neck (typically the carotid artery). While this procedure has been shown to be effective in the clinic and easy for the physician to perform, there remain some distinct disadvantages using this approach.

For example, one disadvantage is that the stent may not sufficiently retain the clot as it pulls the clot to the catheter. In such a case, some or all of the clot might remain the vasculature. Another risk is that as the stent mobilizes the clot from the original blockage site, the clot might not adhere to the stent as the stent is withdrawn toward the catheter. This is a particular risk when passing through bifurcations and tortuous anatomy. Furthermore, blood flow can carry the clot (or fragments of the clot) into a branching vessel at a bifurcation. If the clot is successfully brought to the end of the guide catheter in the carotid artery, yet another risk is that the clot may be "stripped" or "sheared" from the stent as the stent enters the guide catheter. Regardless, simply dragging an expanded stent (either fully or partially expanded) can result in undesired trauma to the vessel. In most cases, since the stent is oversized compared to the vessel, dragging a fixed metallic (or other) structure can pull the arteries and/or strip the cellular lining from the vessel, causing further trauma such as a hemorrhagic stroke (leakage of blood from a cerebral vessel). Also, the stent can become lodged on plaque on the vessel walls resulting in further vascular damage.

In view of the above, there remains a need for improved devices and methods that can remove occlusions from body lumens and/or vessels.

SUMMARY

At least some of the embodiments disclosed herein are devices, systems, and methods for retrieving clot material from a blood vessel lumen. For example, some embodiments are directed to a clot retrieving device that includes an elongated shaft configured to be intravascularly positioned at or adjacent clot material within a blood vessel lumen, and a retrieval assembly coupled to a distal region of the elongated shaft. The retrieval assembly may include a flexible cover and a capture structure. The retrieval assembly may be deployed within the blood vessel lumen at or near the clot material such that the capture structure engages or otherwise becomes enmeshed with at least a portion of the clot material and at least a portion of the cover presses outwardly against the blood vessel wall proximal of the capture structure. Pulling the elongated shaft proximally everts the cover over the capture structure such that the cover at least partially ensheaths the capture structure and associated clot material. The retrieval assembly can then be withdrawn to remove the clot retrieval device and associated clot material from the patient.

In at least some embodiments of the present technology, the retrieval assembly is coupled to the elongated shaft via a connection assembly. The connection assembly may include, for example, a connector coupling the cover to the distal zone of the elongated shaft. In some embodiments, a portion of the cover may protrude proximally from the connector. In some embodiments, the device may include a jacket at least partially over the proximal terminus of the connector and the portion of the cover that protrudes proximally from the connector. As such, the jacket prevents direct contact between the cover and the protruding portion of the cover inverts over the connection assembly.

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause (1, 14, 27, etc.). The other clauses can be presented in a similar manner.

1. A clot retrieving device, comprising:
an elongated shaft having a distal region;
a capture structure having a proximal portion coupled to the distal region of the elongated shaft and a distal portion having a distal terminus; and
a cover having a first portion coupled to the distal region of the elongated shaft and a second portion extending from the first portion, the cover having a first configuration in which the second portion of the cover extends proximally from the first portion, and the cover having a second configuration in which the capture structure is at least partially ensheathed within the first portion of the cover and the second portion of the cover extends distally from the first portion, and in the second configuration the second portion has (a) a first region distal to a distal terminus of the capture structure, the first region tapering radially inwardly in a distal direction, and (b) a second region extending distally and radially outwardly from the first region.

2. The clot retrieving device of Clause 1 wherein, in the second configuration, the second region of the second portion extends distally and circumferentially radially outwardly from the first region.

3. The clot retrieving device of Clause 1 or Clause 2 wherein, in the second configuration, the second portion of the cover has a third region extending proximally from the second region.

4. The clot retrieving device of Clause 3 wherein, in the second configuration, the second portion of the cover has a fourth region that extends distally and radially outwardly from the third region, wherein the third region and the fourth region meet at a proximal folded edge.

5. The clot retrieving device of any one of Clauses 1-4 wherein, in the second configuration, the first and second regions of the second portion together define a channel extending therethrough.

6. The clot retrieving device of Clause 5 wherein, in the second configuration, the first portion of the cover defines an axially-extending cavity that is continuous with the channel of the second portion.

7. The clot retrieving device of Clause 5 or Clause 6 wherein a diameter of the channel decreases in a distal direction along the first region and increases in a distal direction along the second region.

8. The clot retrieving device of any one of Clauses 1-7 wherein, when the cover is unconstrained in the first configuration, the cross-sectional area at the second portion of the cover is greater than the cross-sectional area at the first portion of the cover.

9. The clot retrieving device of any one of Clauses 1-8 wherein the cover is a braid comprising a plurality of interwoven filaments.

10. The clot retrieving device of Clause 9 wherein at least some of the plurality of filaments comprise a superelastic material.

11. The clot retrieving device of Clause 9 wherein at least some of the plurality of filaments are drawn-filled tube ("DFT") wires comprising a radiopaque core material surrounded by a superelastic material.

12. The clot retrieving device of any one of Clauses 1-11 wherein the capture structure is a stent.

13. The clot retrieving device of Clause 12 wherein the stent is a cut tube.

14. A clot retrieving device, comprising:
an elongated shaft having a distal region;
a capture structure having a proximal portion coupled to the distal region of the elongated shaft and a distal portion having a distal terminus; and
a cover coupled to the distal region of the elongated shaft, the cover having a first portion and a second portion extending from the first portion, wherein the cover has (a) a first configuration in which the second portion of the cover extends proximally from the first portion, and (b) a second configuration in which the capture structure is at least partially ensheathed within the first portion of the cover and the second portion extends distally from the first portion, and wherein, in the second configuration, the second portion has:
a neck portion distal to the capture structure, the neck portion having a cross-sectional area that decreases then increases in a distal direction,
a broad portion that curves radially outwardly and proximally from a distal region of the neck portion, and
a channel extending through the neck portion that terminates at an opening at a distal face of the cover.

15. The clot retrieving device of Clause 14 wherein, in the second configuration, the broad portion of the second portion curves circumferentially radially outwardly and proximally from the distal region of the neck portion.

16. The clot retrieving device of Clause 14 or Clause 15 wherein, in the second configuration, the second portion of the cover has an inverted portion that extends distally and radially outwardly from the broad portion, wherein the broad portion and the inverted portion meet at a curved edge.

17. The clot retrieving device of any one of Clauses 14-16 wherein, in the second configuration, a length of the neck portion and a length of the broad portion define the distal face of the cover.

18. The clot retrieving device of any one of Clauses 14-17 wherein, in the second configuration, the broad portion surrounds and is spaced apart from at least a portion of the length of the neck portion.

19. The clot retrieving device of any one of Clauses 14-18 wherein, in the second configuration, a cross-sectional area of the broad portion is greater than the cross-sectional area of the first portion of the cover.

20. The clot retrieving device of any one of Clauses 14-19 wherein, when the cover is unconstrained in the first configuration, the cross-sectional area at the second portion of the cover is greater than the cross-sectional area at the first portion of the cover.

21. The clot retrieving device of any one of Clauses 14-20 wherein in the second configuration the cover is inverted relative to the first configuration.

22. The clot retrieving device of any one of Clauses 14-21 wherein the cover is a braid comprising a plurality of interwoven filaments.

23. The clot retrieving device of Clause 22 wherein at least some of the plurality of filaments comprise a superelastic material.

24. The clot retrieving device of Clause 22 wherein at least some of the plurality of filaments are drawn-filled tube ("DFT") wires comprising a radiopaque core material surrounded by a superelastic material.

25. The clot retrieving device of any one of Clauses 14-24 wherein the capture structure is a stent.

26. The clot retrieving device of Clause 25 wherein the stent is a cut tube.

27. A device for removing material from a vessel, comprising:
an elongated shaft configured to position and advance a capture structure and a cover within the vessel,
the capture structure configured to interlock with a portion of the material, and the cover configured to invert when advanced proximally and,
when inverted, a first portion of the cover is configured to ensheath the capture structure and a second portion of the cover is configured to extend distally from the first portion, taper radially inward from a distal terminus of the capture structure to a narrow portion, and then curve radially outward from the narrow portion.

28. The clot retrieving device of Clause 27 wherein, when inverted, the second portion of the cover is configured to curve circumferentially radially outward from the narrow portion.

29. The clot retrieving device of Clause 27 or Clause 28 wherein the device is configured to be removed from the vessel and the inverted cover is configured to evert after removal.

30. The clot retrieving device of Clause 29 wherein the device having the everted cover is configured to be repositioned within the vessel or positioned within a different vessel.

31. A method for using a clot retrieval device to retrieve clot material from a blood vessel of a patient, the clot retrieval device including a capture structure and a cover having a first portion and a second portion, the method comprising:
expanding the clot retrieval device within the blood vessel lumen into a first configuration such that the second portion of the cover extends proximally from the first portion of the cover and the second portion of the cover contacts an interior surface of the vessel wall;
moving the capture structure proximally relative to the cover to transform the clot retrieval device from the first configuration into a second configuration in which (a) the first portion of the cover surrounds the capture structure, and (b) the second portion extends distally from the first portion, the second portion tapering radially inward distal to a distal terminus of the capture structure to a narrow region, and then curves radially outwardly from the narrow region to form a wide region; and
retaining at least a portion of the clot material within the cover and removing the clot material and clot retrieval device from the patient with the clot retrieval device in the second configuration.

32. The method of Clause 31 wherein the wide region includes:
a first portion extending distally and radially outwardly from a distal terminus of the narrow region, and
a second portion extending proximally from a distal terminus of the first portion of the wide region.

33. The method of Clause 32 wherein the wide region further includes a third portion extending distally and radially outwardly from a distal terminus of the wide region, wherein the second portion of the wide region and the third portion of the wide region meet at a proximal edge of the wide region.

34. The method of any one of Clauses 31-33 wherein the clot retrieval device is constrained within a delivery sheath during delivery of the clot retrieval device to the clot material, and wherein expanding the clot retrieval device includes withdrawing the delivery sheath proximally beyond the cover.

35. The method of any one of Clauses 31-34, further comprising inverting the first portion of the cover while the second portion of the cover remains in contact with the vessel wall.

36. The method of any one of Clauses 31-35 wherein, when the clot retrieval device is positioned in the blood vessel in the first configuration, the second portion of the cover exerts a greater radially outward force on the vessel wall than the first portion.

37. The method of any one of Clauses 31-36 wherein expanding the clot retrieval device includes expanding the capture structure distal of the clot material.

38. A device for retrieving clot material from a blood vessel, the device comprising:
an elongated member having a distal region configured to be intravascularly positioned at or near the clot material within the blood vessel; and
a cover having a proximal portion, an intermediate portion, and a distal portion, the cover slideably coupled to the distal region of the elongated member at a connector, the cover having an inner layer and an outer layer continuous with the inner layer at the distal terminus of the cover, wherein the proximal end portions of each of the inner layer and the outer layer are fixed relative to one another at the connector, and wherein, at least when the cover is in an expanded, relaxed state:
the inner layer has (a) a first cross-sectional dimension at the proximal portion of the cover, (b) a distally increasing cross-sectional dimension along the intermediate portion of the cover, and (c) a second cross-sectional dimension at the distal portion of the cover, wherein the second cross-sectional dimension is greater than the first cross-sectional dimension, and
the outer layer has a cross-sectional dimension that is generally constant along the distal portion and the intermediate portion of the cover.

39. The device of Clause 38 wherein the cross-sectional dimension of the outer layer along the distal and intermediate portions of the cover is greater than an inner diameter of the portion of the blood vessel adjacent to the clot material such that, when the cover is expanded within the blood vessel lumen, the outer layer exerts a radially outward force on the blood vessel wall along at least the distal and intermediate portions of the cover.

40. The device of Clause 38 or Clause 39 wherein, at least when the cover is in an expanded, relaxed state, the outer layer along the proximal portion of the cover has a distal region and a proximal region extending proximally from the distal region to the connector, and wherein (a) the distal region has a generally constant cross-sectional dimension, and (b) a cross-sectional dimension of the proximal region decreases in a proximal direction.

41. The device of Clause 40 wherein, at least when the cover is in an expanded, relaxed state, the cross-sectional dimension of the distal region of the outer layer is substantially the same as the cross-sectional dimension along the distal and intermediate portions of the cover.

42. The device of any one of Clauses 38-41 wherein, at least when the cover is in an expanded, relaxed state, the first cross-sectional dimension of the inner layer is generally constant along the proximal portion of the cover.

43. The device of any one of Clauses 38-42 wherein, at least when the cover is in an expanded, relaxed state, the second cross-sectional dimension of the inner layer is generally constant along the distal portion of the cover.

44. The device of any one of Clauses 38-43 wherein, at least when the cover is in an expanded, relaxed state:
the first cross-sectional dimension of the inner layer is generally constant along the proximal portion of the cover, and
the second cross-sectional dimension of the inner layer is generally constant along the distal portion of the cover.

45. The device of any one of Clauses 38-44 wherein the distal terminus of the cover defines an opening configured to receive a capture structure therethrough, and wherein the cover includes a cavity extending proximally from the opening to the connector.

46. The device of Clause 45 wherein the intermediate portion of the inner layer is convex towards the cavity.

47. The device of Clause 45 wherein the intermediate portion of the inner layer has a distal region that is concave towards the cavity, and a proximal region that is convex towards the cavity.

48. The device of any one of Clauses 38-47 wherein the distal terminus of the cover is a folded edge.

49. The device of any one of Clauses 38-48 wherein the cover is an inverted tubular braid.

50. The device of any one of Clauses 38-49 wherein the elongated member is a solid wire.

51. The device of any one of Clauses 38-50, wherein, when the capture structure is received in the cover, a first portion of the inner layer is displaced radially outward to accommodate the capture structure, and a second portion of the inner layer, located distal of the first portion, remains collapsed radially inward to form at least a partial closure distal of the capture structure.

52. A system for retrieving clot material from a blood vessel, the system comprising:
an elongated member having a distal region configured to be intravascularly positioned at or near the clot material within the blood vessel;
a capture structure having a proximal portion coupled to the distal region of the elongated member at a first connector; and
a cover coupled to the distal region of the elongated member at a second connector, the second connector proximal of the first connector along the elongated member, wherein the cover has a first portion extending proximally from the distal terminus, a second portion extending proximally from first portion, and a third portion extending proximally from the second portion to the second connector,
wherein the cover has an inner layer and an outer layer continuous with the inner layer at the distal terminus of the cover, each of the inner layer and the outer layer having proximal ends fixed at the second connector, and wherein, at least when the cover is in an expanded, relaxed state:
the inner layer has a funnel-shaped region along the first portion of the cover and a neck region extending along the second and third portions of the cover, and
the outer layer has a generally cylindrical shape along the first and second portions of the cover, and a decreasing cross-sectional dimension along the third portion of the cover.

53. The system of Clause 52 wherein the funnel-shaped region of the cover has a distal portion with a generally constant cross-sectional dimension and a tapered proximal portion.

54. The system of Clause 52 or Clause 53 wherein, at least when the cover is in an expanded, relaxed state, the distal terminus of the cover surrounds an opening configured to receive the capture structure therethrough.

55. The system of Clause 54 wherein the inner layer surrounds a cavity extending from the opening to the third portion of the cover.

56. The system of any one of Clauses 52-55 wherein, as the capture structure is moved proximally along the neck region of the inner layer while the cover is expanded within the blood vessel such that the outer layer contacts with the blood vessel wall, a distance between the inner layer and the outer layer decreases along the portion of the cover axially aligned with the capture structure.

57. The system of any one of Clauses 52-56 wherein the cover is an inverted tubular braid.

58. The system of any one of Clauses 52-57 wherein the cover is a mesh and the capture structure is a stent formed of a cut tube.

59. The system of any one of Clauses 52-58, wherein, when the capture structure is received in the cover, a first portion of the inner layer is displaced radially outward to accommodate the capture structure, and a second portion of the inner layer, located distal of the first portion, remains collapsed radially inward to form at least a partial closure distal of the capture structure.

60. A system for retrieving clot material from a blood vessel, the system comprising:
an elongated member having a distal region configured to be intravascularly positioned at or near the clot material within the blood vessel;
a capture structure having a proximal portion coupled to the distal region of the elongated member; and
a dual-layer cover coupled to the distal region of the elongated member at a location proximal of the capture structure, wherein the cover has a radially expansile outer layer that tends to self-expand toward an inner wall of the blood vessel, and an inner layer that tends to collapse inward toward the elongated member such that the inner layer is spaced radially inward from the outer layer; and
the cover being slidable on the elongated member so that the capture structure can be received in the cover.

61. The system of Clause 60, wherein, when the capture structure is received in the cover, a first portion of the inner layer is displaced radially outward to accommodate the capture structure, and a second portion of the inner layer, located distal of the first portion, remains collapsed radially inward to form at least a partial closure distal of the capture structure.

62. The system of Clause 60 or 61, wherein the cover has a closed proximal end.

63. The system of any one of Clauses 60-62, wherein a distalmost portion of the inner layer is not collapsed radially inward, so as to form an enlarged distal opening of the cover.

64. The system of any one of Clauses 60-63, wherein the distalmost portion of the inner layer extends proximally in at least partial contact with a radially adjacent portion of the outer layer.

65. The system of any one of Clauses 60-64, wherein at least the distal region of the elongated member comprises a wire.

66. The system of any one of Clauses 60-65, wherein at least the distal region of the elongated member comprises a stent retriever.

67. The system of any one of Clauses 60-66, wherein a distal terminus of the cover is a folded edge.

68. The system of any one of Clauses 60-67, wherein the cover is an inverted tubular braid and the capture structure is a stent formed of a cut tube.

69. The system of any of Clauses 60-68, wherein the cover is coupled to the elongated member at a connector, and wherein the cover has a proximal portion, an intermediate portion, and a distal portion, and wherein, at least when the cover is in an expanded, relaxed state:
the inner layer has (a) a first cross-sectional dimension at the proximal portion of the cover, (b) a distally increasing cross-sectional dimension along the intermediate portion of the cover, and (c) a second cross-sectional dimension at the distal portion of the cover, wherein the second cross-sectional dimension is greater than the first cross-sectional dimension, and
the outer layer has a cross-sectional dimension that is generally constant along the distal portion and the intermediate portion of the cover.

70. A device for retrieving clot material from a blood vessel lumen, the device comprising:
an elongated shaft having a distal zone;
a capture structure having a proximal region coupled to the distal zone of the elongated shaft;
a cover having a first portion coupled to the distal zone of the elongated shaft and a free second portion, the cover having a first position in which the second portion extends proximally from the first portion, and a second position inverted relative to the first position in which the second portion extends distally from the first portion such that the cover at least partially surrounds the capture structure; and
a connector coupled to the elongated shaft proximal of the capture structure, the connector including an inner band and an outer band, wherein (a) the inner band at least partially surrounds a portion of the distal zone of the elongated shaft, (b) the outer band at least partially surrounds the inner band, and (c) the first portion of the cover is secured between the inner band and the outer band.

71. The device of Clause 70 wherein the connector is coupled to the distal zone of the elongated shaft by a crimp and/or a binding agent.

72. The device of Clause 70 wherein the connector is configured to move with respect to the elongated shaft.

73. The device of any one of Clauses 70-72 wherein the connector is a first connector and the device further comprises a second connector at least partially surrounding the proximal region of the capture structure, and wherein the inner band of the first connector has a first inner diameter and the second connector has a second inner diameter greater than or equal to the first inner diameter of the inner band.

74. The device of any one of Clauses 70-73, wherein the connector is crimped to the first portion of the cover.

75. The device of any one of Clauses 72-74, further comprising a stop fixed to the elongated shaft proximal of the connector.

76. The device of Clause 75 wherein the stop includes a coil attached to the elongated shaft.

77. The device of any one of Clauses 70-76 wherein the connector is a first connector, the device further comprising a second connector, wherein the second connector and the inner band and/or the outer band are composed of a radiopaque material.

78. The device of any one of Clauses 70-77 wherein the inner band and/or the outer band are composed of a radiopaque material.

79. The device of any one of Clauses 70-78 wherein the cover is composed of a plurality of drawn-filled tube ("DFT") wires, and at least a portion of the outer band comprises platinum.

80. The device of any one of Clauses 70-79 wherein at least a portion of the cover comprises a superelastic material.

81. The device of any one of Clauses 70-80 wherein the inner and outer bands have generally the same length.

82. The device of any one of Clauses 70-81 wherein a distal terminus of the inner band and a distal terminus of the outer band are at least generally aligned along a plane approximately normal to the elongated shaft.

83. The device of any one of Clauses 70-82 wherein a proximal terminus of the inner band and a proximal terminus of the outer band are at least generally aligned along a plane approximately normal to the elongated shaft.

84. The device of any one of Clauses 70-83 wherein the cover includes a plurality of interwoven wires, and a portion of the wires protrude proximally from a proximal terminus of the outer band, and wherein the device further comprises a jacket over the proximal terminus of the outer band and the protruding portion of the wires.

85. The device of Clause 84 wherein the jacket further extends over a portion of the elongated shaft proximal of the proximal terminus of the outer band.

86. The device of any one of Clauses 70-85 wherein the inner band and the outer band each include a proximal terminus, and the proximal terminus of the inner band extends proximally beyond the proximal terminus of the outer band, the device further comprising a jacket over the proximal terminus of the outer band and a portion of the inner band that extends proximal of the proximal terminus of the outer band.

87. The device of any one of Clauses 70-86 wherein the capture structure is a stent and the cover is a braid.

88. A device for retrieving clot material from a blood vessel lumen, the device comprising:
an interventional element having an elongated proximal region;
a manipulation member having a distal zone, wherein the proximal region of the interventional element is coupled to the distal zone of the manipulation member;
a cover having a first portion coupled to the distal zone of the manipulation member and a free second portion, the cover having a first position in which the second portion extends proximally from the first portion, and a second position inverted relative to the first position in which the second portion extends distally from the first portion such that the cover at least partially surrounds the interventional element;
an inner band proximal to the interventional element and at least partially surrounding a portion of the distal zone of the manipulation member; and
an outer band at least partially surrounding the inner band, wherein the first portion of the cover is secured between the inner band and the outer band.

89. The device of Clause 88 wherein the inner band, the cover and the outer band are coupled to the distal zone of the manipulation member by a crimp and/or a binding agent.

90. The device of Clause 88 wherein the inner band and the outer band are configured to move with respect to the manipulation member.

91. The device of any one of Clauses 88-90 wherein the inner band and the outer band are crimped to the first portion of the cover.

92. The device of any one of Clauses 88-91, further comprising a stop fixed to the manipulation member and proximal of the inner band, wherein the stop has an inner diameter greater than the inner diameter of the inner band.

93. The device of any one of Clauses 88-92, further comprising a connector at least partially surrounding the proximal region of the interventional element and a portion of the distal zone of the manipulation member, wherein at least a portion of the cover comprises a superelastic material, and the connector and/or the outer band are composed of a radiopaque material.

94. The device of any one of Clauses 88-93 wherein a proximal terminus of the inner band and a proximal terminus of the outer band are generally aligned along a plane approximately normal to the manipulation member.

95. A method for retrieving clot material from a treatment site within a blood vessel lumen, the method comprising:
providing a clot retrieving device including an elongated shaft having a distal zone and a retrieval assembly at the distal zone, the retrieval assembly having:
a capture structure with a proximal region coupled to the distal zone of the elongated shaft,
a cover having a first portion coupled to the distal zone of the elongated shaft and a free second portion, the cover having a first position in which the second portion extends proximally from the first portion, and a second position in which the second portion extends distally from the first portion such that the cover at least partially surrounds the capture structure, and
a connector coupled to the elongated shaft proximal of the capture structure, the connector including an inner band and an outer band, wherein (a) the inner band at least partially surrounds the distal zone of the elongated shaft, (b) the outer band at least partially surrounds the inner band, and (c) the first portion of the cover is secured between the inner band and the outer band;
intravascularly advancing the clot retrieving device within a delivery catheter to the treatment site such that the retrieval assembly is positioned proximate the clot material at the treatment site;
deploying the retrieval assembly within the blood vessel lumen such that the capture structure expands at the clot material and the cover is in the first position; and
withdrawing the retrieval assembly proximally through the delivery catheter to remove the clot material from the treatment site.

96. The device of Clause 95 wherein the connector is coupled to the distal zone of the elongated shaft by a crimp and/or a binding agent.

97. The device of Clause 95, further comprising moving the connector axially relative to the elongated shaft.

98. The device of any one of Clauses 95-97 wherein the retrieval assembly further includes a stop proximal to the connector, and wherein the stop includes a coil attached to the elongated shaft.

99. The device of any one of Clauses 95-98 wherein deploying the retrieval assembly includes inverting the cover from the first position to the second position.

100. A device for retrieving clot material from a blood vessel lumen, the device comprising:
an elongated shaft having a distal zone;
a capture structure having a proximal region coupled to the distal zone of the elongated shaft;
a cover having a first end portion coupled to the distal zone of the elongated shaft and a free second end portion, the cover having a first position in which the second end portion extends proximally from the first end portion, and a second position in which the second end portion extends distally from the first end portion such that the cover at least partially surrounds the capture structure and is inverted relative to the first position;
a connector coupled to the distal zone of elongated shaft, the connector including an inner band and an outer band, wherein (a) the inner band at least partially surrounds the distal zone of the elongated shaft and a portion of the proximal region of the capture structure, (b) the outer band at least partially surrounds the inner band, and (c) the first end portion of the cover is secured between the inner band and the outer band.

101. The device of Clause 100, further comprising a jacket material over a proximal terminus of the inner band and a portion of the elongated shaft proximal of the proximal terminus of the inner band.

102. The device of Clause 101 wherein the jacket material is an inner jacket material, the device further comprising an outer jacket material over a proximal terminus of the outer band and at least a portion of the inner jacket material proximal of the proximal terminus of the outer band.

103. The device of Clause 101 or Clause 102 wherein the jacket material is an inner jacket material, the device further comprising an outer jacket material over a proximal terminus of the outer band and at least a portion of the elongated shaft proximal of the proximal terminus of the outer band.

104. The device of any of Clauses 100-104, further comprising an inner jacket material and an outer jacket material, wherein the inner jacket material is over a proximal terminus of the inner band and the outer jacket material is over a proximal terminus of the outer band.

105. The device of Clause 100 wherein the proximal region of the capture structure, the connector, and the first end portion of the cover are coupled to the distal zone of the elongated shaft by a crimp.

106. The device of any one of Clauses 100-105 wherein at least one of the inner band and the outer band is composed of a radiopaque material.

107. The device of any one of Clauses 100-106 wherein the cover is composed of a plurality of drawn-filled tube ("DFT") wires, and at least a portion of the outer band comprises platinum.

108. The device of any one of Clauses 100-107 wherein at least a portion of the cover comprises a superelastic material.

109. The device of any one of Clauses 100-108 wherein the inner and outer bands have generally the same length.

110. The device of any one of Clauses 100-109 wherein a distal terminus of the inner band and a distal terminus of the outer band are generally aligned along a plane normal to the elongated shaft.

111. The device of any one of Clauses 100-110 wherein a proximal terminus of the inner band and a proximal terminus of the outer band are generally aligned along a plane normal to the elongated shaft.

112. The device of any of Clauses 100-111 wherein the proximal region of the capture structure, the connector, and the first end portion of the cover are coupled to the distal zone of the elongated shaft.

113. The device of any one of Clauses 100-112 wherein the cover includes a plurality of interwoven wires, and a portion of the wires protrude proximally from a proximal terminus of the outer band, and wherein the device further comprises a jacket material over the proximal terminus of the outer band and the protruding portion of the wires.

114. The device of any one of Clauses 100-113 wherein the inner band and the outer band each include a proximal terminus, and the proximal terminus of the inner band extends proximally beyond the proximal terminus of the outer band, and wherein the device further comprises a jacket material over the proximal terminus of the outer band and a portion of the inner band proximal of the proximal terminus of the outer band.

115. The device of any one of Clauses 100-114 wherein the capture structure is a stent and the cover is a braid.

116. A device for retrieving clot material from a blood vessel lumen, the device comprising:
- an interventional element having an elongated proximal region and an opening extending laterally through the proximal region;
- a manipulation member having a distal zone and a coupling element at the distal zone, wherein at least a portion of the coupling element extends through the opening at the proximal region of the interventional element;
- a cover having a first end portion coupled to the distal zone of the manipulation member and a free second end portion, wherein the cover has a first position in which the second end portion extends proximally from the first end portion, and a second position in which the second end portion extends distally from the first end portion such that the cover at least partially surrounds the interventional element and is inverted relative to the first position.
- an inner band at least partially surrounding the distal zone of the manipulation member and a portion of the proximal region of the interventional element; and
- an outer band at least partially surrounding the inner band, wherein the first end portion of the cover is secured between the inner band and the outer band.

117. The device of Clause 116, further comprising a jacket material over a proximal terminus of the inner band and at least a portion of the elongated shaft proximal of the proximal terminus of the inner band.

118. The device of Clause 117 wherein the jacket material is an inner jacket material, the device further comprising an outer jacket material over a proximal terminus of the outer band and at least a portion of the inner jacket material proximal of the proximal terminus of the outer band.

119. The device of Clause 116, further comprising an inner jacket material and an outer jacket material, wherein the inner jacket material covers a proximal terminus of the inner band and the outer jacket material covers a proximal terminus of the outer band.

120. The device of any of Clauses 116-119 wherein the proximal region of the interventional element, the inner band, the outer band and the first end portion of the cover are coupled to the distal zone of the elongated shaft by a crimp.

121. The device of any one of Clauses 116-120 wherein at least a portion of the distal zone of the manipulation member is bent.

122. The device of any one of Clauses 116-121 wherein at least one of the inner band and the outer band is composed of a radiopaque material, and the cover is composed of a plurality of DFT wires.

123. The device of any one of Clauses 116-122 wherein the cover includes a plurality of interwoven wires, and a portion of the wires protrude proximally from a proximal terminus of the outer band, and wherein the device further comprises an inner jacket material and an outer jacket material, the inner jacket material covering a proximal terminus of the inner band and the outer jacket material covering a proximal terminus of the outer band and the portion of protruding wires.

124. A method for retrieving clot material from a treatment site within a blood vessel lumen, the method comprising:
- providing a clot retrieving device including an elongated shaft having a distal zone and a retrieval assembly at the distal zone, the retrieval assembly having:
  - a capture structure with a proximal region coupled to the distal zone of the elongated shaft,
  - a cover having a first end portion coupled to the distal zone of the elongated shaft and a free second end portion, the cover having a first position in which the second end portion extends proximally from the first end portion, and a second position in which the second end portion extends distally from the first end portion such that the cover at least partially surrounds the capture structure and is inverted relative to the first position, and
  - a connector coupled to the distal zone of elongated shaft, the connector including an inner band and an outer band, wherein (a) the inner band at least partially surrounds the distal zone of the elongated shaft and the proximal region of the capture structure, (b) the outer band at least partially surrounds the inner band, and (c) the first end portion of the cover is secured between the inner band and the outer band;
- intravascularly advancing the clot retrieving device within a delivery catheter to the treatment site such that the retrieval assembly is positioned proximate the clot material at the treatment site;
- deploying the retrieval assembly within the blood vessel lumen such that the retrieval assembly expands to the first position; and
- withdrawing the retrieval assembly proximally through the delivery catheter to remove clot material from the treatment site.

125. The method of Clause 124, further comprising an inner jacket material over a proximal terminus of the inner band, and an outer jacket material over a proximal terminus of the outer band.

126. The method of Clause 124 or Clause 125 wherein the proximal region of the capture structure, the connector, and the first end portion of the cover are coupled to the distal zone of the elongated shaft by a crimp.

127. The method of any one of Clauses 124-126 wherein the cover includes a plurality of interwoven wires, and a portion of the wires protrude proximally from a proximal terminus of the outer band, and wherein the device further comprises a jacket material at least partially over the proximal terminus of the outer band and the protruding portion of the wires.

128. The method of any one of Clauses 124-127 wherein at least one of the inner band and the outer band is composed of a radiopaque material, and the cover is composed of a plurality of DFT wires.

129. The method of any one of Clauses 124-128 wherein the inner band and the outer band each include a proximal terminus, and the proximal terminus of the inner band extends proximally beyond the proximal terminus of the outer band, and wherein the device further comprises a jacket material at least partially over the proximal terminus of the outer band and the inner band proximally adjacent the proximal terminus of the outer band.

130. A device for retrieving clot material from a blood vessel lumen, the device comprising:
  an elongated shaft having a distal zone;
  a capture structure having a proximal region coupled to the distal zone of the elongated shaft;
  a cover including a plurality of filaments, the cover having a first portion coupled to the distal zone of the elongated shaft and a free second portion, the cover having a first position in which the second portion extends proximally from the first portion, and a second position inverted relative to the first position in which the second portion extends distally from the first portion such that the cover at least partially surrounds the capture structure;
  a connector coupling the first portion of the cover to the distal zone of the elongated shaft, wherein at least a portion of the filaments protrude proximally from a proximal terminus of the connector; and
  a jacket at least partially over the proximal terminus of the connector and the protruding portion of the filaments, wherein the jacket prevents direct contact between the cover and the protruding portions of the filaments as the cover moves from the first position to the second position.

131. The device of Clause 130 wherein the cover is a braid, and the capture structure is a stent.

132. The device of Clause 130 or Clause 131 wherein the jacket includes a polymer.

133. The device of any one of Clauses 130-132 wherein the jacket includes a fluoropolymer.

134. The device of any one of Clauses 130-133 wherein at least a portion of the jacket comprises polytetrafluoroethylene ("PTFE").

135. The device of any one of Clauses 130-134 wherein the jacket includes a heat-shrinkable material.

136. The device of any one of Clauses 130-135 wherein the jacket is at least partially over a portion of the elongated shaft proximal of the proximal terminus of the connector.

137. The device of any one of Clauses 130-136 wherein the inner band at least partially surrounds the proximal region of the capture structure.

138. The device of any one of Clauses 130 wherein the connector is a first connector, and the device further comprises a second connector distal of the first connector along the elongated shaft, wherein the second connector at least partially surrounds the proximal region of the capture structure and the distal zone of the elongated shaft.

139. The device of any one of Clauses 130-138 wherein the first connector is configured to move with respect to the elongated shaft.

140. The device of any one of Clauses 130-139, further comprising a stop fixed to the elongated shaft proximal of the first connector.

141. The device of any one of Clauses 130-140 wherein the connector includes an inner band and an outer band, and wherein:
  the inner band at least partially surrounds a portion of the distal zone of the elongated shaft,
  the outer band at least partially surrounds the inner band, and
  the first portion of the cover is secured between the inner band and the outer band.

142. The device of Clause 141 wherein the portion of the elongated shaft is a first portion, and the device further comprises a buffer material positioned over a second portion of the elongated shaft proximal of the proximal terminus of the inner band.

143. The device of Clause 142 wherein the buffer material is a coil.

144. A device for retrieving clot material from a blood vessel lumen, the device comprising:
  an interventional element;
  a manipulation member having a distal zone;
  a cover having a first portion coupled to the distal zone of the manipulation member and a free second portion, the cover having a first position in which the second portion extends proximally from the first portion, and a second position inverted relative to the first position in which the second portion extends distally from the first portion such that the cover surrounds at least a portion of the interventional element;
  a connector coupling the first portion of the cover to the distal zone of the manipulation member, wherein at least a portion of the cover extends proximally from a proximal terminus of the connector; and
  a jacket extending from the proximal terminus of the connector and covering the extending portion of the cover, thereby preventing the extending portion of the cover from engaging the remaining portion of the cover as the cover moves from the first position to the second position.

145. The device of Clause 144 wherein the interventional element includes a proximal region at least partially surrounded by the connector.

146. The device of Clause 145 or Clause 146 wherein the connector includes an inner band and an outer band, and wherein the jacket is an outer sleeve, the device further comprising an inner sleeve over a proximal terminus of the inner band and a portion of the manipulation member proximal of the proximal terminus of the inner band.

147. The device of any one of Clauses 144-146 wherein the connector is a first connector, the device further comprising a second connector at least partially surrounding the proximal region of the interventional element and the portion of the distal zone of the manipulation member.

148. The device of any one of Clauses 144-147 wherein the connector includes an inner band and an outer band, and wherein the inner band is proximal of the proximal region of the interventional element and at least partially surrounds a portion of the distal zone of the manipulation member, and the outer band at least partially surrounds the inner band.

149. The device of Clause 146 or Clause 148 wherein a proximal terminus of the inner band extends proximally beyond a proximal terminus of the outer band, and wherein the jacket is at least partially over the inner band proximal of the proximal terminus of the outer band.

150. The device of any one of Clauses 144, 145, 147, 148 or 149 wherein the inner band and the outer band are configured to move with respect to the manipulation member.

151. The device of any one of Clauses 144-150, further comprising a stop fixed to the manipulation member proximal of the connector.

152. The device of any one of Clauses 144-151 wherein the jacket is a heat-shrinkable material.

153. The device of any one of Clauses 144-152 wherein at least a portion of the heat-shrinkable material is composed of a fluoropolymer.

154. The device of any one of Clauses 144-151 wherein:

the interventional element includes an elongated proximal region and an opening extending laterally through the proximal region, and the manipulation member includes a coupling element at the distal zone of the manipulation member, wherein at least a portion of the coupling element extends through the opening of the interventional element.

155. A method for retrieving clot material from a treatment site within a blood vessel lumen, the method comprising:

providing a clot retrieving device including an elongated shaft having a distal zone and a retrieval assembly at the distal zone, the retrieval assembly having:
a capture structure with a proximal region coupled to the distal zone of the elongated shaft,
a cover having a plurality of filaments, a first portion coupled to the distal zone of the elongated shaft and a free second portion, the cover having a first position in which the second portion extends proximally from the first portion, and a second position inverted relative to the first position in which the second portion extends distally from the first portion such that the cover at least partially surrounds the capture structure,
a connector coupling the first portion of the cover to the distal zone of the elongated shaft, wherein at least a portion of the filaments protrude proximally from a proximal terminus of the connector, and
a jacket at least partially over the proximal terminus of the connector and the protruding portion of the filaments;
intravascularly advancing the clot retrieving device within a delivery catheter to the treatment site such that the retrieval assembly is positioned proximate the clot material at the treatment site;
deploying the retrieval assembly within the blood vessel lumen such that the retrieval assembly expands to the first position; and
withdrawing the retrieval assembly proximally through the delivery catheter to remove clot material from the treatment site.

156. The method of Clause 155 wherein the connector at least partially surrounds the proximal region of the capture structure.

157. The method of Clause 155 wherein the connector is a first connector proximal of the proximal region of the capture structure, and the device further comprises a second connector at least partially surrounding the proximal region of the capture structure.

158. The method of any one of Clauses 155-157 wherein the jacket is at least partially over a portion of the elongated shaft proximal of the proximal terminus of the connector.

159. The method of any one of Clauses 155-158 wherein the connector includes an inner band and an outer band, wherein:

the inner band at least partially surrounds a portion of the distal zone of the elongated shaft,
the outer band at least partially surrounds the inner band, and
the first portion of the cover is secured between the inner band and the outer band.

160. The method of any one of Clauses 155-159 wherein the jacket is a heat-shrinkable material composed of a fluoropolymer.

Additional features and advantages of the subject technology are described below, and in part will be apparent from the description, or may be learned by practice of the subject technology. The advantages of the subject technology will be realized and attained by the structure particularly pointed out in the written description and claims hereof as well as the appended drawings.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present disclosure.

FIG. 3A is a side view of a distal portion of a clot retrieval device shown with a retrieval assembly shown in a first configuration in accordance with embodiments of the present technology.

FIG. 3B is a side view of the distal portion of the clot retrieval device of FIG. 3A, shown with the retrieval assembly in a second, everted configuration.

FIGS. 5A and 5B illustrate a method of removing clot material from a blood vessel lumen using the clot retrieval device shown in FIGS. 3A and 3B.

FIG. 6A is a side view of a distal portion of a clot retrieval device in accordance with some embodiments of the present technology.

FIG. 6B is an enlarged view of a portion of the cover shown in FIG. 6A.

FIGS. 8A-8C illustrate a method of removing clot material from a blood vessel lumen using the clot retrieval device shown in FIG. 6A.

DETAILED DESCRIPTION

The present technology provides devices, systems, and methods for removing clot material from a blood vessel lumen. Although many of the embodiments are described below with respect to devices, systems, and methods for treating a cerebral or intracranial embolism, other applications and other embodiments in addition to those described herein are within the scope of the technology. For example, the retrieval devices of the present technology may be used to remove emboli from body lumens other than blood vessels (e.g., the digestive tract, etc.) and/or may be used to remove emboli from blood vessels outside of the brain (e.g., pulmonary blood vessels, blood vessels within the legs, etc.). In addition, the retrieval devices of the present technology may be used to remove luminal obstructions other than clot material (e.g., plaque, resected tissue, foreign material, etc.).

An overview of the retrieval devices of the present technology and associated methods of use is described below under heading 1.0 with reference to FIGS. 1A-2G. Some embodiments of various subcomponents of the retrieval devices of the present technology are described below under headings 2.0 and 3.0. In particular, some embodiments of covers are described further under heading 2.0 with reference to FIGS. 3A-8C, and some embodiments of connection assemblies are described further under heading 3.0 with reference to FIGS. 9A-15.

1.0 OVERVIEW

Figure 1A:
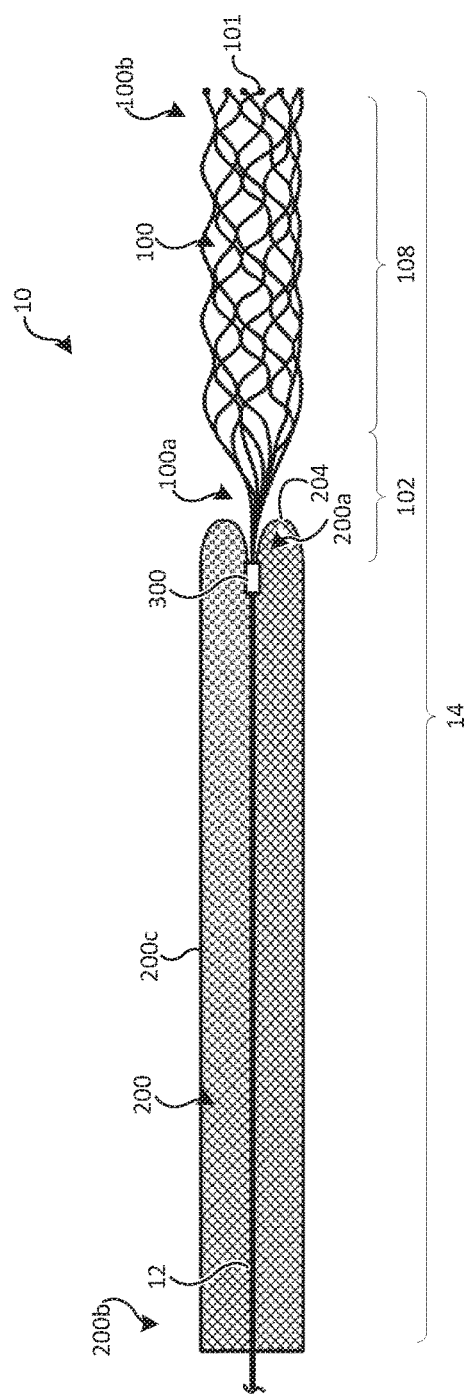
FIG. 1A is a side view of a distal portion of a clot retrieval device shown with a retrieval assembly in a first configuration in accordance with the present technology.
Figure 1B:
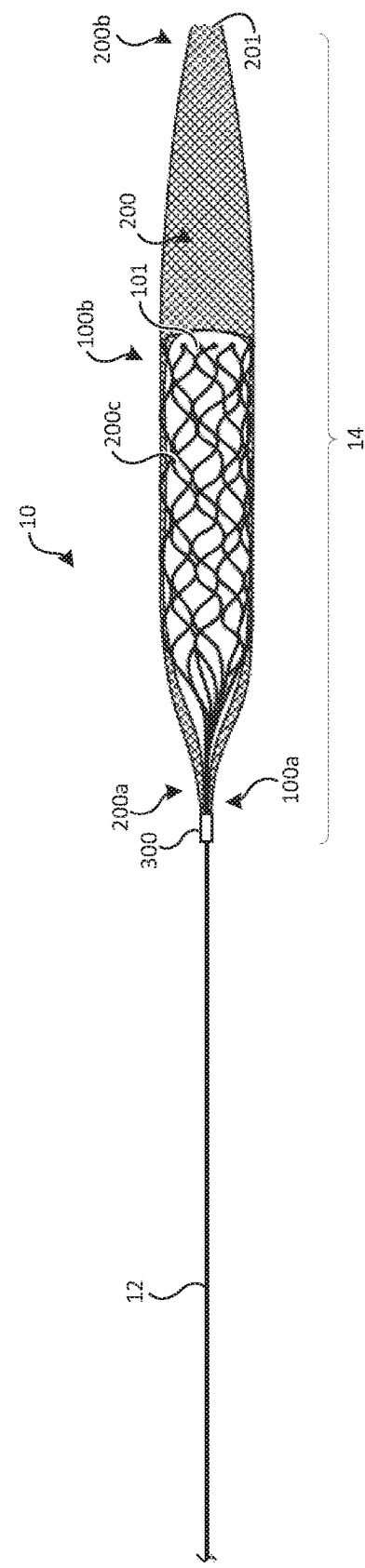
FIG. 1B is a side view of the distal portion of the clot retrieval device of FIG. 1A, shown with the retrieval assembly shown in a second, everted configuration.

FIGS. 1A and 1B are side views of a distal portion of some embodiments of a retrieval device or a clot retrieving device 10 ("device 10") outside of a blood vessel in an expanded, relaxed (e.g., unconstrained) configuration in accordance with the present technology. The clot retrieving device 10 is shown in first and second configurations in FIGS. 1A and 1B, respectively. As shown in FIGS. 1A and 1B, the clot retrieving device 10 includes an elongated shaft 12 ("shaft 12") and a retrieval assembly 14 coupled to a distal region of the elongated shaft 12 via a connection assembly 300. The retrieval assembly 14 is configured to be intravascularly positioned at or adjacent clot material within a blood vessel lumen and includes a capture structure 100 and a flexible cover 200. A portion of the cover is removed in FIGS. 1A and 1B for ease of viewing the capture structure 100. In some embodiments, the capture structure 100 and the cover 200 are fixed to the elongated shaft 12 at generally the same location, or the capture structure 100 and cover 200 may be coupled to the shaft 12 at different locations and/or may be slidable with respect to the elongated shaft 12.

The capture structure 100 has a low-profile configuration (not shown) when constrained within a delivery catheter (e.g., a microcatheter) and an expanded configuration for securing and/or engaging clot material or other obstructions within a blood vessel lumen (e.g., a cerebral blood vessel lumen) and/or for restoring blood flow within the blood vessel. The capture structure 100 has a proximal portion 100a coupled to the shaft 12 and a distal portion 100b. The capture structure 100 further includes an open cell framework or body 108 (FIG. 1A) and a coupling region 102 (FIG. 1A) extending proximally from the body 108. In some embodiments, for example as shown in FIGS. 1A and 1B, a distal portion 100b of the capture structure 100 can be generally tubular (e.g., cylindrical), and the proximal portion 100a of the capture structure 100 tapers proximally to the coupling region 102. In some embodiments, the distal terminus of the distal portion 100b coincides with a distal terminus 101 of the capture structure 100 and/or retrieval assembly 14.

Referring again to FIGS. 1A and 1B, in some embodiments the capture structure 100 is a mesh structure formed of a superelastic material (e.g., Nitinol) or other resilient or self-expanding material configured to self-expand when released from the delivery catheter. For example, in some embodiments the capture structure 100 may be a stent and/or stentriever, such as Medtronic's Solitaire™ Revascularization Device, Stryker Neurovascular's Trevo® ProVue™ Stentriever, or other suitable devices. In other embodiments, the capture structure 100 may include a plurality of braided filaments. Examples of suitable capture structures 100 include any of those disclosed in U.S. Pat. No. 7,300,458, filed Nov. 5, 2007, U.S. Pat. No. 8,940,003, filed Nov. 22, 2010, U.S. Pat. No. 9,039,749, filed Oct. 1, 2010, and U.S. Pat. No. 8,066,757, filed Dec. 28, 2010, each of which is incorporated by reference herein in its entirety.

The cover 200 includes a first end portion 200a coupled to the shaft 12 via the connection assembly 300, a free second end portion 200b, and a cover wall 200c extending between the first end portion 200a and the second end portion 200b. As used herein to describe the second end portion 200b of the cover 200, the term "free" refers to a portion of the cover 200 that is not fixed to the elongated shaft 12 and may move radially and/or longitudinally with respect to the shaft 12. The cover 200 is flexible such that it is movable between a first position (FIG. 1A) in which the free second end portion 200b is proximal of the first end portion 200a and a second position (FIG. 1B) in which the cover 200 is inverted over the capture structure 100 such that a distal terminus 201 (FIG. 1B) of the cover 200 is at or distal to the distal terminus 101 of the capture structure 100 and/or to the first end portion 200a. As shown in FIG. 1A, when the cover 200 is in the first position in an expanded, relaxed state, some embodiments of the cover 200 may have a leading edge 204 that overlaps the coupling region 102 of the capture structure 100 but does not extend beyond the coupling region 102 to overlap the body 108 of the capture structure 100. In some embodiments, the leading edge 204 of the cover 200 may also overlap all or a portion of the length of the body 108 when the cover 200 is in the first position. As shown in FIG. 1B, when the cover 200 is in the second position, the free second end portion 200b is distal of the first end portion 200a and distal of the distal terminus 101 of the capture structure 100. As such, when in the second position, the cover wall 200c surrounds the capture structure 100.

The cover 200 can comprise a mesh and/or braid of a plurality of wires (e.g., filaments, threads, sutures, fibers or the like) that have been interwoven to form a structure having openings (e.g., a porous fabric). The mesh and/or braid can be composed of metals, polymers, composites, and/or biologic materials. Polymer materials can include Dacron, polyester, polypropylene, nylon, Teflon, polytetrafluoroethylene (PTFE), tetrafluoroethylene, polyethylene terephthalate, polyactic acid (PLA) silicone, polyurethane, polyethylene, polycarbonate, styrene, polyimide, PEBAX, Hytrel, polyvinyl chloride, high-density polyethylene, low-density polyethylene, polyether ether ketone (PEEK), rubber, latex, and/or other suitable polymers known in the art. Other materials known in the art of elastic implants can also be used. Metal materials can include, but are not limited to, nickel-titanium alloys (e.g. Nitinol), platinum, cobalt-chromium alloys, stainless steel, tungsten or titanium. In certain embodiments, metal filaments may be highly polished and/or surface treated to further improve their hemocompatibility. The cover 200 can be constructed solely from metallic materials without the inclusion of any polymer materials, solely from polymer materials without the inclusion of any metallic materials, or a combination of polymer and metallic materials.

In some embodiments, some or all of the wires of the cover 200 are drawn-filled tube ("DFT") wires having a radiopaque core (e.g., platinum, tantalum, gold, tungsten, etc.) surrounded by a superelastic material (e.g., Nitinol, a cobalt-chromium alloy, etc.). The radiopaque core may comprise about 5% to about 50% (e.g., 10%, 15%, 20%, 25%, 30%, 35%, 40%, 45%) of the total-cross-sectional area of the individual wires. In some embodiments, the cover 200 may have 72-144 total wires (e.g., 72, 96 128, 144, etc.) Moreover, some or all of the wires may have a wire diameter of about 0.005 inches to about 0.015 inches (e.g., 0.008 inches, 0.01 inches, etc.). In some embodiments, all of the wires have the same diameter, and in other embodiments some of the wires have different diameters. Further details regarding cover embodiments in accordance with the present technology are described below with reference to FIGS. 3A-8C.

Figure 2A:
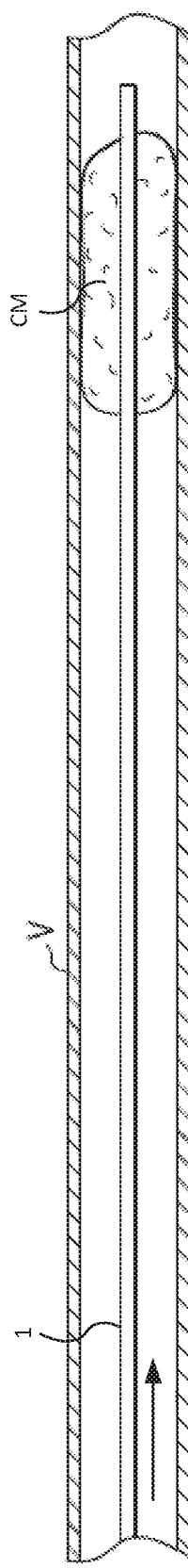
FIGS. 2A-2G illustrate a method of removing clot material from a blood vessel lumen using the clot retrieval device shown in FIGS. 1A and 1B.
Figure 2B:
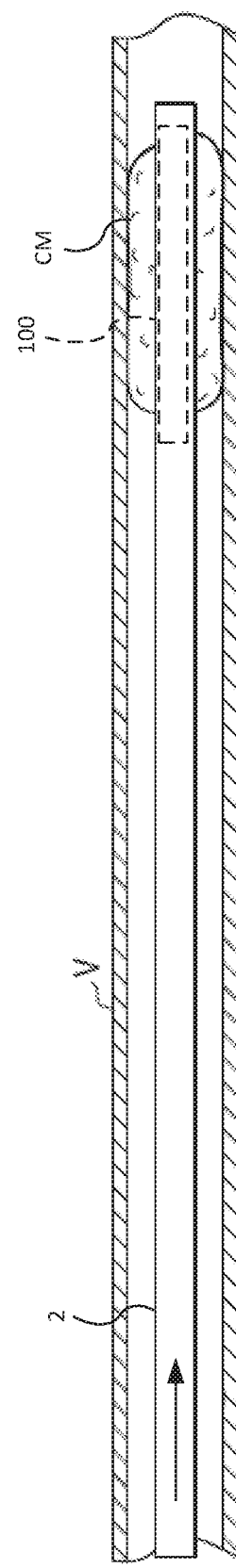
Figure 2C:
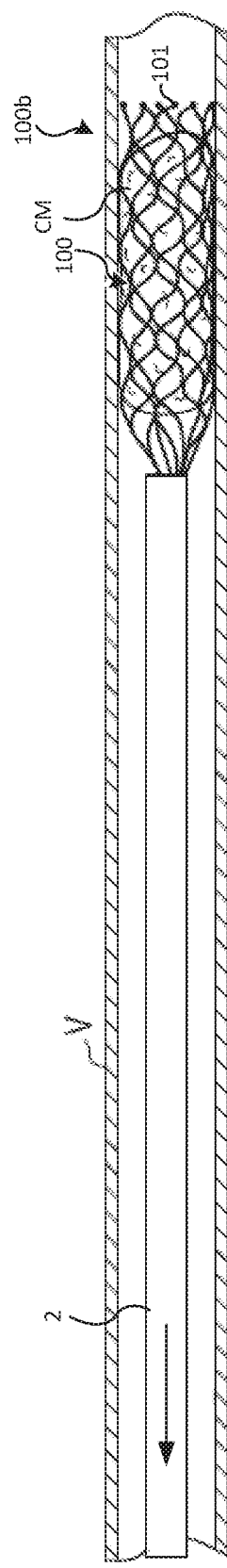
Figure 2D:
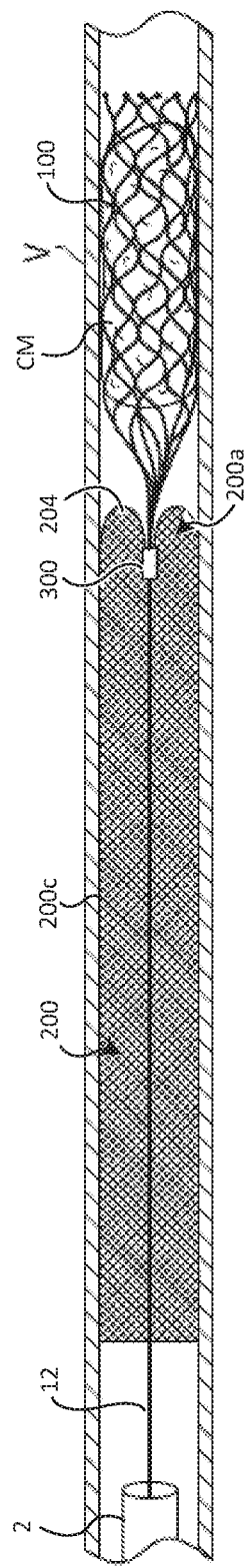

FIGS. 2A-2G illustrate a method of removing clot material from the lumen of a blood vessel V using the clot retrieving device 10 of the present technology. As shown in FIG. 2A, a guidewire 1 may be advanced through the clot material CM such that a distal terminus of the guidewire 1 is distal of the clot material CM. Next, a delivery catheter 2 may be delivered over the guidewire 1 so that a distal portion of the delivery catheter 2 is positioned at or near the clot material CM. As shown in FIG. 2B, in some embodiments the delivery catheter 2 may be advanced over the guidewire 1 through the clot material CM such that a distal terminus of the delivery catheter 2 is distal of the clot material CM. With the delivery catheter 2 in position, the guidewire 1 may be withdrawn. The clot retrieving device 10 may then be advanced through the delivery catheter 2 in a low-profile configuration until a distal terminus 101 of the capture structure 100 (shown schematically in FIG. 2B) is at or adjacent the distal terminus of the delivery catheter 2. As shown in FIGS. 2C and 2D, the delivery catheter 2 may then be pulled proximally relative to the clot retrieving device 10 to release the capture structure 100, thereby allowing the capture structure 100 to self-expand within the clot material CM. As the capture structure 100 expands, the capture structure 100 engages and/or secures the surrounding clot material CM, and in some embodiments may restore or improve blood flow through the clot material CM. In some embodiments, the capture structure 100 may be expanded distal of the clot material CM such that no portion of the capture structure 100 is engaging the clot material CM while the capture structure 100 is in the process of expanding toward the vessel wall. In some embodiments, the capture structure 100 is configured to expand into contact with the blood vessel wall, or the capture structure 100 may expand to a diameter that is less than that of the blood vessel lumen such that the capture structure 100 does not engage the entire circumference of the blood vessel wall.

As shown in FIG. 2D, the delivery catheter 2 may continue advancing proximally to release the cover 200 such that at least a portion of the cover wall 200c expands into contact with the blood vessel wall and the cover 200 is in the first position. Once the delivery catheter 2 is moved proximal of the cover 200 in the first position and both the cover 200 and the capture structure 100 are expanded within the vessel lumen, the retrieval assembly 14 is in the first configuration.

Figure 2E:
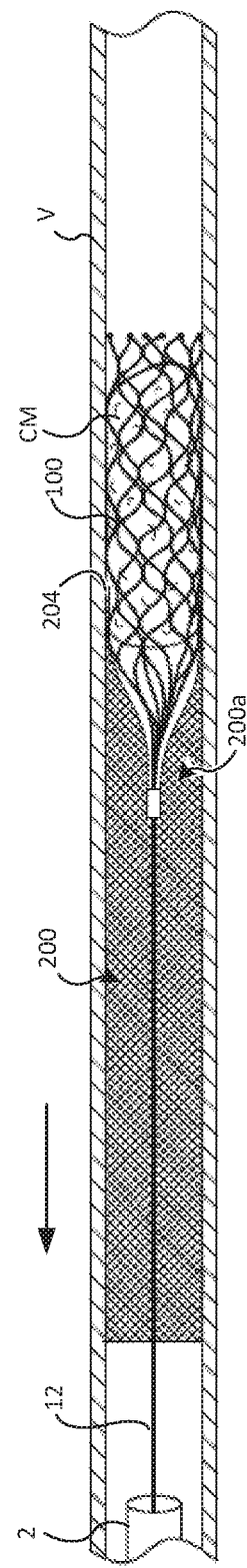
Figure 2F:
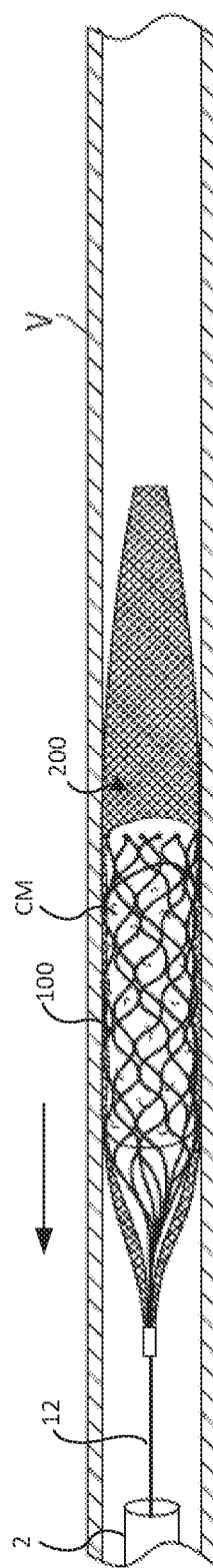
Figure 2G:
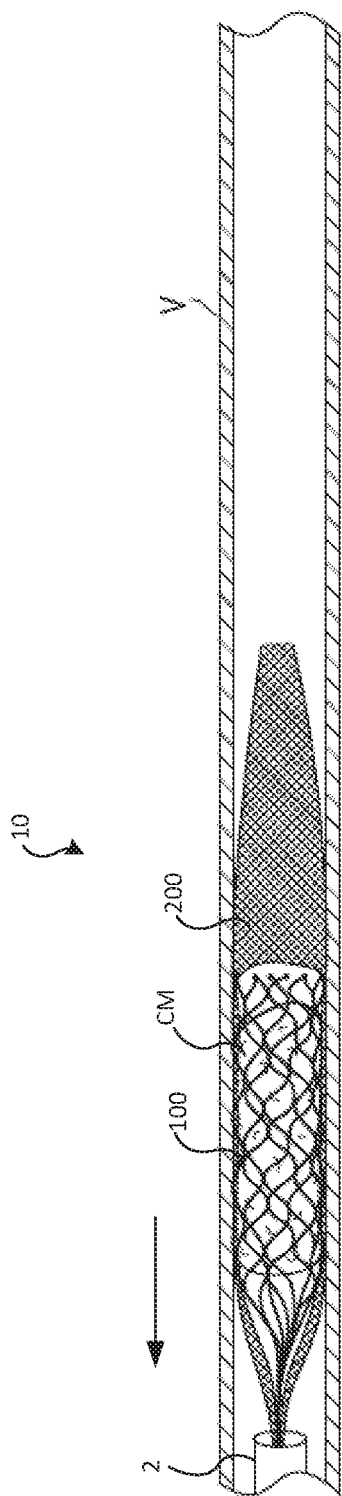

As shown in FIG. 2E, when the elongated shaft 12 is pulled proximally while the retrieval assembly 14 is in the first configuration, friction between the blood vessel wall and the cover wall 200c prevents or resists proximal movement of the free second end portion 200b of the cover 200 while the first end portion 200a of the cover 200 moves in a proximal direction with the capture structure 100. In other words, expansion of the cover 200 provides sufficient friction against the walls of the vessel V to overcome the column strength of the cover wall 200c, thereby causing the cover wall 200c to remain in place and/or move less than the first end portion 200a of the cover 200 so that the cover wall 200c inverts over the proximally advancing capture structure 100 and any associated clot material CM. As the elongated shaft 12 is moved proximally and the cover 200 is inverting, the capture structure 100 moves proximally relative to the leading edge 204 of the cover 200 so that the length of the capture structure 100 coextensive with the cover 200 increases. Eventually, the cover 200 completely inverts from the first position over the capture structure 100, thereby further securing any clot material held by or within the capture structure. As shown in FIG. 2G, the clot retrieving device 10 may continue advancing proximally until the retrieval assembly 14 is positioned within the delivery catheter 2. The delivery catheter 2, device 10, and associated clot material CM may then be withdrawn from the patient.

2.0 SELECTED EMBODIMENTS OF COVERS AND ASSOCIATED METHODS OF USE

FIGS. 3A-8C show various embodiments of covers for use with the clot retrieving devices of the present technology. Although the covers discussed below are described with reference to the clot retrieving device 10 shown in FIGS. 1A-2G, any of the covers disclosed herein may be used with any of the clot retrieval devices disclosed herein. For example, any of the covers discussed below may be used with any of the connection assemblies discussed with reference to FIGS. 9A-15.

FIGS. 3A and 3B are side views of a retrieval assembly 344 of a clot retrieving device 340 shown outside of a blood vessel in an expanded, relaxed (e.g., unconstrained) configuration in accordance with the present technology. The clot retrieving device 340 and retrieval assembly 344 can include components that are generally similar in structure and function as those of the clot retrieving device 10 shown in FIGS. 1A-2G. For example, the clot retrieving device 340 includes the elongated shaft 12 and the connection assembly 300. As such, common acts and structure are identified by the same reference numbers, and only significant differences in operation and structure are described below.

The retrieval assembly 344 may include the capture structure 100 and a cover 350 coupled to the elongated shaft 12 by the connection assembly 300. In some embodiments, the capture structure 100 and the cover 350 are fixed to the elongated shaft 12 at generally the same location, or the capture structure 100 and cover 200 may be coupled to the shaft 12 at different locations and/or may be slidable with respect to the elongated shaft 12. Additional details regarding the connection assembly 300 and relative positions of the capture structure 100 and cover 350 are described in greater detail below with reference to FIGS. 9A-15.

The cover 350 may be a mesh structure. For example, in some embodiments the cover 350 is a braided tube having one or more preset shapes. The cover 350 can comprise a mesh and/or braid of a plurality of wires (e.g., filaments, threads, sutures, fibers or the like) that have been interwoven to form a structure having openings (e.g., a porous fabric). The mesh and/or braid can be composed of metals, polymers, composites, and/or biologic materials. Polymer materials can include Dacron, polyester, polypropylene, nylon, Teflon, polytetrafluoroethylene (PTFE), tetrafluoroethylene, polyethylene terephthalate, polyactic acid (PLA) silicone, polyurethane, polyethylene, polycarbonate, styrene, polyimide, PEBAX, Hytrel, polyvinyl chloride, high-density polyethylene, low-density polyethylene, polyether ether ketone (PEEK), rubber, latex, and/or other suitable polymers known in the art. Other materials known in the art of elastic implants can also be used. Metal materials can include, but are not limited to, nickel-titanium alloys (e.g. Nitinol), platinum, cobalt-chromium alloys, stainless steel, tungsten or titanium. In certain embodiments, metal filaments may be highly polished or surface treated to further improve their hemocompatibility. The cover 350 can be constructed solely from metallic materials without the inclusion of any polymer materials, solely from polymer materials without the inclusion of any metallic materials, or a combination of polymer and metallic materials.

In some embodiments, some or all of the wires of the cover 350 are DFT wires having a radiopaque core (e.g., platinum, tantalum, gold, tungsten, etc.) surrounded by a superelastic material (e.g., Nitinol, a cobalt-chromium alloy, etc.). The radiopaque core may comprise about 5% to about 50% (e.g., 10%, 15%, 20%, 25%, 30%, 35%, 40%, 45%) of the total-cross-sectional area of the individual wires. In some embodiments, the cover 200 may have 72-144 total wires (e.g., 72, 96 128, 144, etc.) Moreover, some or all of the wires may have a wire diameter of about 0.005 inches to about 0.015 inches (e.g., 0.008 inches, 0.01 inches, etc.). In some embodiments, all of the wires have the same diameter, and in other embodiments some of the wires have different diameters.

The cover 350 includes a first end portion 350a coupled to the shaft 12 via the connection assembly 300, a free second end portion 350b, and a cover wall 350c extending between the first end portion 350a and the second end portion 350b. As used herein to describe the second end portion 350b of the cover 350, the term "free" refers to a portion of the cover 350 that is not fixed to the elongated shaft 12 and may move radially and/or longitudinally with respect to the shaft 12. As shown in FIGS. 3A and 3B, the cover wall 350c includes a body portion 358 and an end portion 356 extending from the body portion 358. The cover 350 is flexible such that it is movable between a first position (FIG. 3A) in which the free second end portion 350b is proximal of the first end portion 350a and a second position (FIG. 3B) in which the cover 350 is inverted over the capture structure 100 such that a distal terminus 345 (FIG. 3B) of the cover 350 is at or distal to the distal terminus 101 of the capture structure 100.

As shown in FIG. 3A, when the cover 350 is in the first position in an expanded, relaxed state, the cover 350 may have a leading edge 354 that overlaps the coupling region 102 of the capture structure 100 but does not extend beyond the coupling region 102 to overlap the body 108 of the capture structure 100. The leading edge 354 of the cover 350 may alternatively overlap all or a portion of the length of the body 108 when the cover 350 is in the first position. As shown in FIG. 3B, when the cover 350 is in the second position, the free second end portion 350b is distal of the first end portion 350a and distal of the distal terminus 101 of the capture structure 100. As such, when in the second position, the body portion 358 of the cover wall 350c defines an axially extending cavity 360 and the capture structure 100 is positioned within the cavity 360.

When the cover 350 is in the first configuration (FIG. 3A), the end portion 356 extends proximally from the body portion 358, and each of the body portion 358 and/or the end portion 356 may have a generally tubular shape. In the illustrated embodiment, the end portion 356 has a cross-sectional dimension (e.g., cross-sectional area, diameter, etc.) that is greater than a cross-sectional dimension (e.g., cross-sectional area, diameter, etc.) of the body portion 358. In other embodiments, the body portion 358 and/or the end portion 356 may have different shapes and/or relative sizes. As shown in FIG. 3B, when the cover 350 is in the second configuration, the body portion 358 may have a generally tubular shape, and at least a region of the end portion 356 may taper inwardly in a distal direction. The end portion 356 may define a channel 362 extending therethrough that is continuous with the cavity 360 and terminates at an opening 364.

Figure 3C:
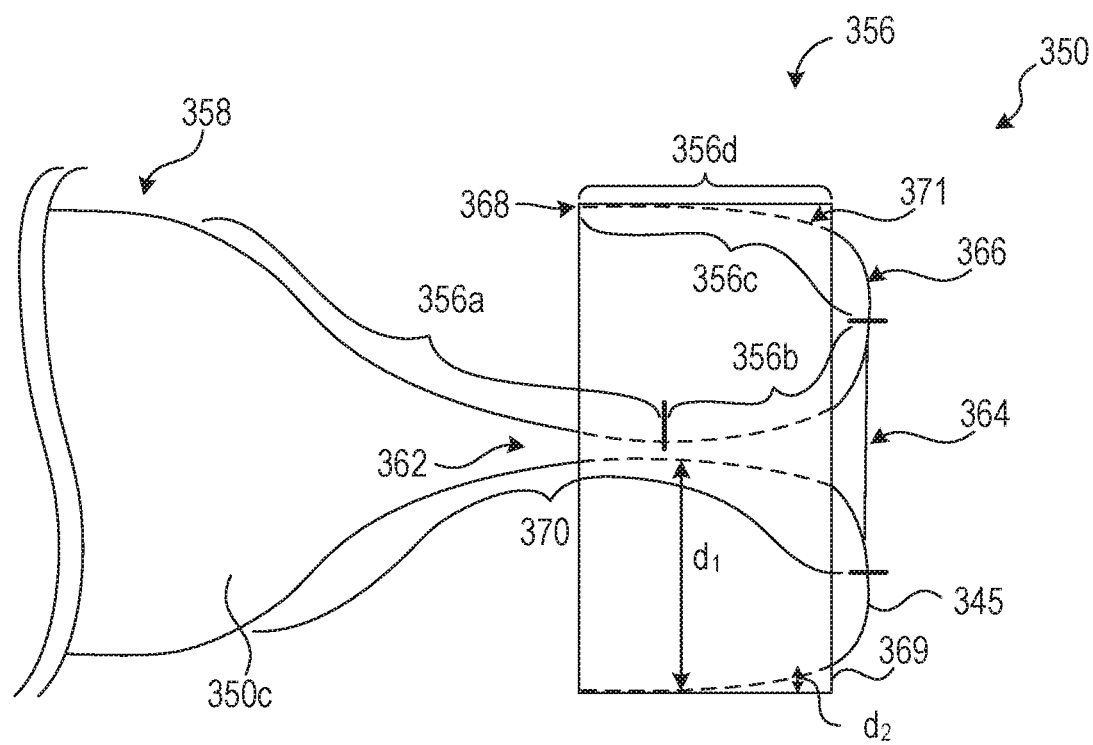
FIGS. 3C and 3D are enlarged side and isometric views, respectively, of a portion of the cover of FIGS. 3A and 3B in an everted configuration in accordance with some embodiments of the present technology.
Figure 3D:
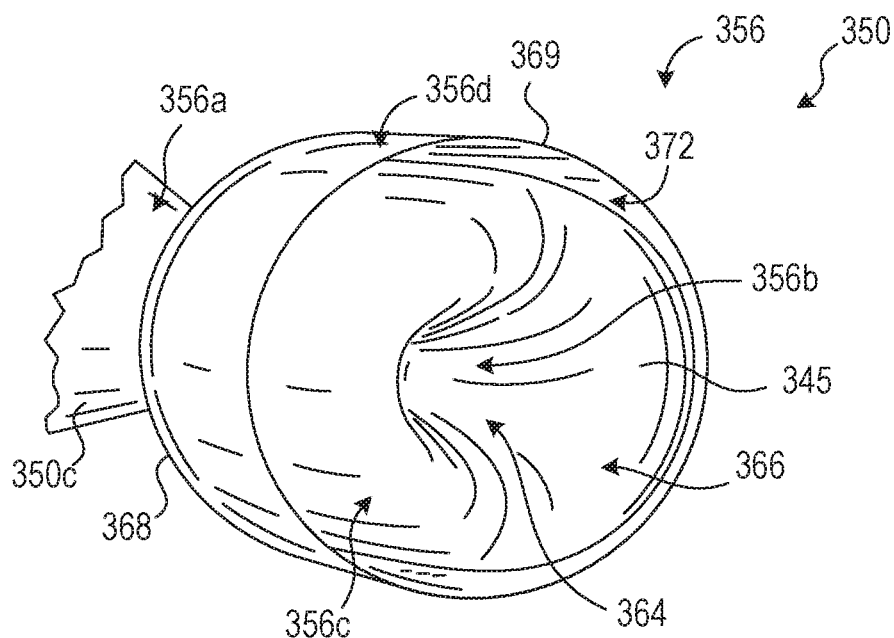

FIGS. 3C and 3D are enlarged side and isometric views, respectively, of the end portion 356 of the cover 350 in the second configuration. The cover 350 is shown without a braided pattern in FIGS. 3C and 3D for ease of viewing and describing the various regions of the end portion 356. As shown in FIGS. 3C and 3D, the end portion 356 may be heat set to have a predetermined shape in the expanded, relaxed state such that at least a length of the end portion 356 distal to a distal terminus 101 of the capture structure 100 (FIG. 1B) tapers radially inwardly, thereby enclosing associated clot material and preventing or otherwise reducing the escape of particles from an interior region of the cover 350. For example, the end portion 356 may have a preset shape in the second configuration such that the cover wall 350c folds onto itself one or more times, thereby forming a first region 356a extending distally and radially inwardly from the body portion 358 (visible in FIG. 3C only), a second region 356b extending distally and radially outwardly from the first region 356a, a broad or third region 356c extending proximally from the second region 356b, and an optional inverted or fourth region 356d extending distally from the third region 356c to a free edge 369. The first region 356a and the second region 356b may together form a neck 370 (FIG. 3C) that defines the channel 362 extending through the end portion 356. As such, the channel 362 has a cross-sectional dimension that may decrease then increase in a distal direction. In some embodiments, the fourth region 356d defines the most radially outward portion of the end portion 356.

In some embodiments, the second region 356b and the third region 356c may together define a curved distal face 366 of the end portion 356 and/or cover 350, and the third region 356c and the fourth region 356d may meet at a proximal, creased and/or folded edge 368 of the end portion 356. The distal terminus 345 of the cover 350 may coincide with the portion of the distal face 366 where the second region 356b meets the third region 356c. In some embodiments, the free edge 369 of the fourth region 356d is proximal of the distal face 366. Overlapping portions of the neck 370 and third region 356c may be in contact with one another or may be separated by a distance $d_1$ (FIG. 3C), and overlapping portions of the third region 356c and the fourth region 356d may be in contact with one another or may be separated by a distance $d_2$ (FIG. 3C). In some embodiments distance $d_1$ is greater than distance $d_2$.

The end portion 356 of FIGS. 3B-3D advantageously facilitates manually retracting the cover 350 following an initial use of the cover and capture structure 100. After an initial use of the retrieval device 340, at which point it will have reached the configuration shown in FIG. 3B, it may be necessary to perform a "second pass" with the device so as to retrieve any clot that remain in the treatment area following the first pass. The clinician can grasp the end portion 356 gently between the thumb and forefinger and urge it in the proximal direction to begin the process of retraction. The cover 356 can be retracted in this manner until it reaches the initial, or fully retracted, configuration shown in FIG. 3A. At this point the capture structure 100 can be cleaned of any retrieved thrombus and the device 340 can be used for a second pass, and any subsequent passes, until a satisfactory removal of thrombus has been achieved.

The broadened and "curled-back" shape of the end portion 356 facilitates manual retraction of the cover and subsequent re-use of the device 340, which can be difficult with a device, such as the clot retrieving device 10, that lacks such a feature. For example, as shown in FIG. 1B, when the cover forms a collapsed, inwardly tapered distal end in the everted or deployed configuration, it can be difficult to push it proximally or "peel back" the cover wall so as to reverse the process of everting. The broadened shape of the end portion 356 allows it to be easily grasped and pushed proximally, while the curled-back shape of the cover wall in the end portion 356 helps to cause the cover to reverse or undo its everted configuration during retraction. Note that these functions and properties apply to the end portion 356 shown in FIGS. 3A-3D, as well as the end portions 356 shown in FIGS. 4A-4N.

Figures 4A, 4B, 4C:
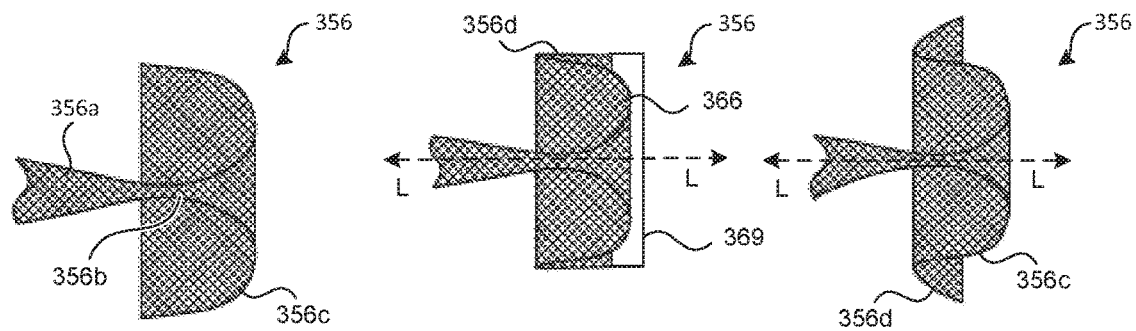
FIGS. 4A-4N are side views of different end regions of covers in a first configuration in accordance with some embodiments of the present technology.
Figures 4D, 4E, 4F:
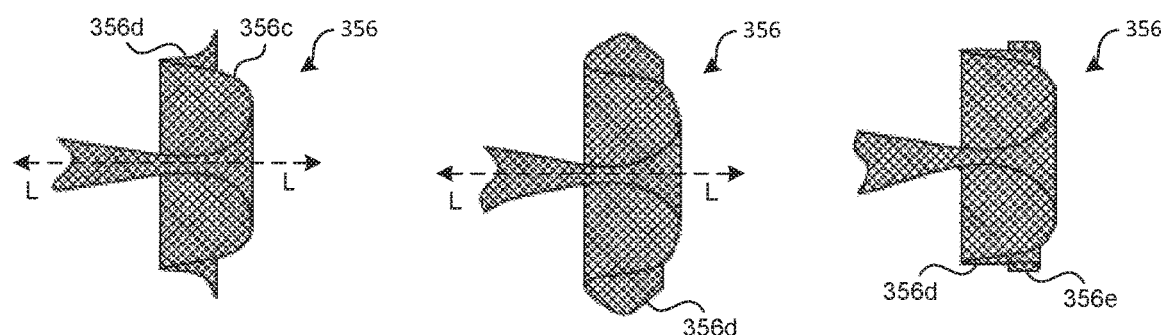

In several embodiments, the end portion 356 may have other shapes and/or configurations when the cover 350 is in the second configuration in an expanded, relaxed state. For example, although the cover wall 350c along the end portion 356 is folded on itself two times in the example shown in FIGS. 3A-3D, the end portion 356 may be folded on itself more or fewer than two times. For example, in some embodiments the end portion 356 may not be folded on itself, or the end portion 356 may be folded on itself only one time such that the end portion 356 only includes the first through third regions 356a-356c and does not include the fourth region 356d as shown in FIG. 4A. In some embodiments, the end portion 356 may be folded on itself three times such that it includes a fifth region 356e extending proximally from the fourth region 356d (FIG. 4F).

Figures 4G, 4H, 4I:
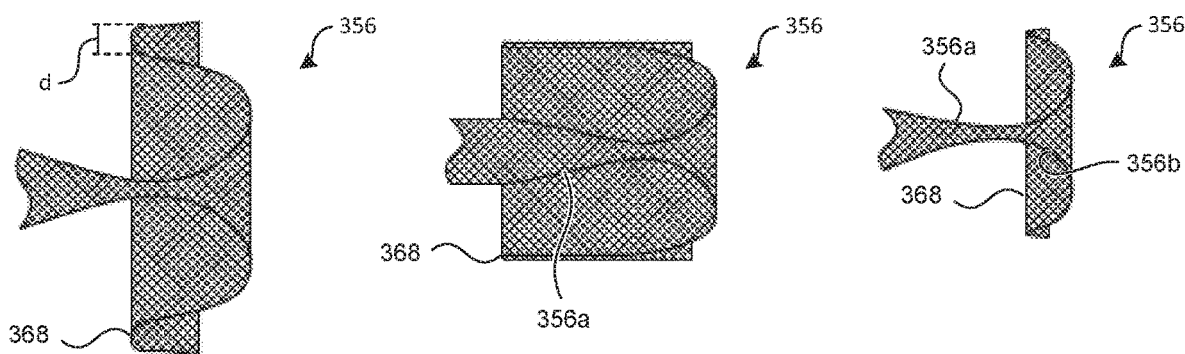

As shown in FIG. 4B, in some embodiments the free edge 369 of the fourth region 356d may be distal of the distal face 366, and the fourth region 356d may extend generally parallel to a longitudinal axis L of the end portion 356. In some embodiments, the fourth region 356d may extend distally and radially outwardly and be concave towards the third region 356c (FIG. 4C), and in some embodiments the fourth region 356d may extend distally and radially outwardly and be convex towards the third region 356c (FIG. 4D). In some embodiments, the fourth region 356d may extend distally and radially outwardly, then radially inwardly (FIG. 4E). As shown in FIG. 4G, in some embodiments the portion of the cover 350 comprising the folded edge 368 may extend radially outwardly generally perpendicular to the longitudinal axis L of the end portion 356 for a distance d. In some embodiments the folded edge 368 may be proximal of the first region 356a (FIG. 4H), or the folded edge 368 may be distal of the first region 356a (FIGS. 4I and 4M). In some embodiments, the neck 370 may include an intermediate region 356f between the first and second regions 356a, 356b that has a generally constant diameter (FIG. 4J).

Figures 4J, 4K, 4L:
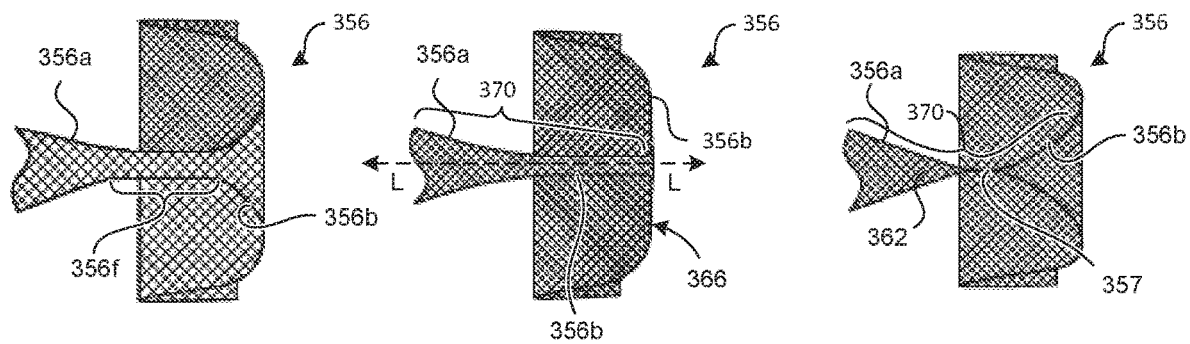
Figures 4M, 4N:
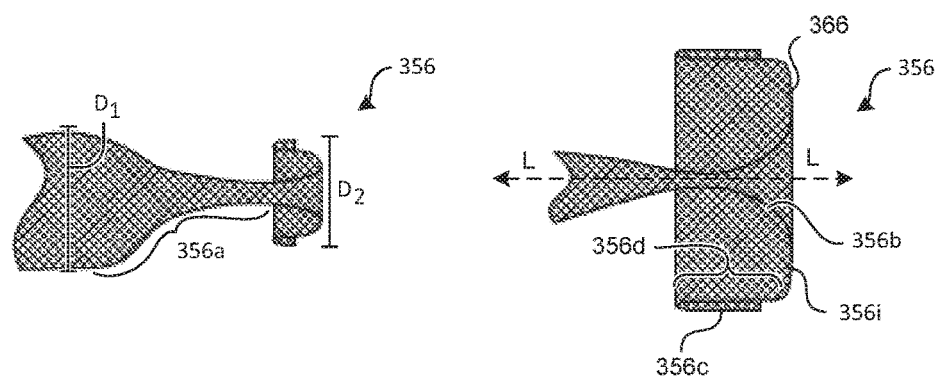

As shown in FIG. 4K, in some embodiments the second region 356b extends distally from the first region 356a generally parallel to the longitudinal axis L of the end portion 356, then extends radially outwardly generally perpendicular to the longitudinal axis L so that the distal face 366 of the end portion 356 and/or cover 350 is generally flat (in contrast to the curved distal face 366 in FIG. 3C). As such, a cross-sectional dimension of the neck 370 tapers in a distal direction then remains generally constant such that the neck 370 does not include a portion that extends radially outwardly. Moreover, as shown in FIG. 4L, in some embodiments the neck 370 tapers down distally to a pinched portion 357 at or along which all or a portion of the cover wall comes together such that the channel 362 is at least partially blocked. In some embodiments, the body portion 358 may have a diameter $D_1$ that is greater than the diameter $D_2$ of the end portion 356 when the cover 350 is in a relaxed, expanded state (FIG. 4M).

In some embodiments, the diameter $D_1$ of the body portion 358 is less than or equal to the diameter $D_2$ of the end portion 356 when the cover 350 is in a relaxed, expanded state (FIG. 3B). As shown in FIG. 4N, in some embodiments, the end portion 356 includes a transition region 356i between the second region 356b and the third region 356c. The transition region 356i may extend radially outwardly from the second region 356b generally perpendicular to the longitudinal axis L of the end portion 356 (i.e., the transition region 356i generally does not extend distally or proximally). In such embodiments, at least a portion of the distal face 366 of the end portion 356 and/or cover 350 is generally flat. In addition, also as shown in FIG. 4N, in some embodiments at least a portion of the third region 356c may extend proximally and generally parallel to the longitudinal axis L of the end portion 356 (i.e., not radially outwardly as shown in FIG. 3C).

In use, the clot retrieving device 340 may be delivered through a delivery catheter 2 (e.g., a microcatheter) to a treatment site within a blood vessel lumen (e.g., a cerebral blood vessel) as described above with reference to FIGS. 2A and 2B. The delivery catheter 2 may then be pulled proximally relative to the clot retrieving device 340 to release the capture structure 100, thereby allowing the capture structure 100 to self-expand within the clot material CM as described above with reference to FIG. 2C. The delivery catheter 2 may continue advancing proximally to release the cover 350 such that at least a portion of the cover wall 350c expands into contact with the blood vessel wall and the cover 350 is in the first position. FIG. 5A, for example, shows the retrieval assembly 344 expanded within the blood vessel lumen in a first configuration. As discussed above, in some embodiments, when the cover 350 is in the first position in a relaxed, expanded state, the end portion 356 may have a cross-sectional dimension (e.g., cross-sectional area, diameter, etc.) that is greater than a cross-sectional dimension (e.g., cross-sectional area, diameter, etc.) of the body portion 358. Accordingly, when the cover 350 is expanded within the blood vessel, both the body portion 358 and the end portion 356 may expand into contact with the blood vessel wall, but the end portion 356 exerts a greater radially outward force on the vessel wall V than the body portion 358. As such, when the retrieval assembly 344 is pulled proximally, the end portion 356 of the cover 350 resists proximal movement to a greater extent than the body portion 358. In some embodiments, only the end portion 356 expands into contact with the blood vessel wall V.

FIG. 5B is a side view of the retrieval assembly 344 in the blood vessel in a second configuration and with the cover 350 in a second, inverted position. As shown in FIG. 5B, when the cover 350 is in the second position in the blood vessel lumen, both the body portion 358 and the broad portion of the end portion 356 (e.g., the third and/or fourth regions 356c, 356d (FIG. 3C)) are in apposition with the blood vessel wall V, while the neck 370 (see FIG. 3C) is not in contact with the blood vessel wall V. As such, as the retrieval assembly 344 is pulled proximally, captured clot material CM having a size greater than the diameter of the channel 362 is prevented from escaping the cavity 360.

FIG. 6A is a cross-sectional side view of one embodiment of a retrieval assembly 602 of a clot retrieving device 600 shown outside of a blood vessel in an expanded, relaxed configuration in accordance with the present technology. The clot retrieving device 600 and retrieval assembly 602 can include components that are generally similar in structure and function as those of the clot retrieving device 10 shown in FIGS. 1A-2G. For example, the clot retrieving device 600 includes the elongated shaft 12, and the retrieval assembly 602 includes the capture structure 100 (only a portion shown for ease of illustration). As such, common acts and structure are identified by the same reference numbers, and only significant differences in operation and structure are described below.

The retrieval assembly 602 may include the capture structure 100 and a cover 604. The proximal region 100a of the capture structure 100 may be coupled to the shaft 12 by connector 607, and a proximal region 604a of the cover 604 may be coupled to the shaft 12 by connector 605. Connector 605 may be positioned along the shaft 12 proximal of connector 607. The connector 607 can be similar to the connector 1201 (and any variations thereof) described with respect to FIGS. 12A-15, and the connector 605 can be similar to the connectors 901, 1001, 1101 (and any variations thereof) described with respect to FIGS. 9A-15.

In some embodiments, the connector 607 and/or proximal region 100a of the capture structure 100 is fixed to the shaft 12, and the connector 605 and/or proximal region 604a of the cover 604 is slidably coupled to the shaft 12. As such, the connector 607 and/or proximal region 100a of the capture structure 100 is movable along the shaft 12 relative to the connector 605 and/or proximal region 604a of the cover 604. In those embodiments where the cover 604 is slidably attached to the shaft 12, the clot retrieving device 600 may include a stop 609 fixed to the shaft 12 proximal of connector 605 that prevents axial movement of connector 605 along the shaft 12 proximal of the stop 609. For example, the stop 609 and/or connector 607 may have a shape and size that inhibit movement of the cover 604 and/or connector 605. In some embodiments, the stop 609 and/or connector 607 can have an outer dimension that is larger than an interior dimension of connector 605 (or vice versa) such that movement of the connector 605 distally beyond connector 607 and/or proximally beyond stop 609 is inhibited or prevented. In some embodiments, the stop 609 may be formed integrally with the shaft 12. In several embodiments, the clot retrieving device 600 may include more than one stop. In some embodiments, the stop 609 can comprise a radiopaque material.

In some embodiments, the cover 604 and/or connector 605 can be fixedly attached to the shaft 12. The cover 604 and/or connector 605 can be fixedly attached to the shaft 12 by, for example, soldering, welding, crimping, adhesive(s), or a combination thereof. In some embodiments, the cover 604 and/or connector 605 can be rotatably coupled to the shaft 12. For example, in some embodiments, the cover 604 and/or connector 605 may be slidably and rotatably coupled to the shaft 12. In some embodiments, the connector 605 may be fixed at a certain axial location along the shaft 12 but is still free to rotate about the shaft 12. In any of the foregoing embodiments, the capture structure 100 and/or connector 607 can be slidably and/or rotatably coupled to the shaft 12.

As shown in FIG. 6A, the cover 604 may be formed of a two-layer mesh structure having an inner layer 606 and an outer layer 608. The inner layer 606 may be continuous with the outer layer 608 at a distal terminus 611 of the cover 604, and the proximal end portions of the inner and outer layer 606, 608 may be fixed relative to one another at connector 605. As such, the cover 604 may have a closed proximal region 604a. The cover 604 may include an opening 612 at its distal region 604b, and the inner layer 606 may define a cavity 610 that extends distally from connector 605 along the length of the cover 604 and terminates at the opening 612. The cavity 610 and/or opening 612 may be configured to receive the elongated shaft 12 and the capture structure 100 therein. In some embodiments, the cover 604 may be formed of an inverted tubular braid such that the distal terminus 611 of the cover 604 may comprise a folded edge of the braid and the first and second ends of the tubular braid are adjacent one another at a proximal region 604a of the cover 604. The folded edge may surround and define the opening 612 at the distal region 604b of the cover 604.

In those embodiments where the cover 604 is a mesh and/or braid, the cover 604 may include a plurality of wires (e.g., filaments, threads, sutures, fibers or the like) that have been interwoven to form a structure having openings (e.g., a porous fabric). The mesh and/or braid can be composed of metals, polymers, composites, and/or biologic materials. Polymer materials can include Dacron, polyester, polypropylene, nylon, Teflon, polytetrafluoroethylene (PTFE), tetrafluoroethylene, polyethylene terephthalate, polyactic acid (PLA) silicone, polyurethane, polyethylene, polycarbonate, styrene, polyimide, PEBAX, Hytrel, polyvinyl chloride, high-density polyethylene, low-density polyethylene, polyether ether ketone (PEEK), rubber, latex, and/or other suitable polymers known in the art. Other materials known in the art of elastic implants can also be used. Metal materials can include, but are not limited to, nickel-titanium alloys (e.g. Nitinol), platinum, cobalt-chromium alloys, stainless steel, tungsten or titanium. In certain embodiments, metal filaments may be highly polished or surface treated to further improve their hemocompatibility. The cover 604 can be constructed solely from metallic materials without the inclusion of any polymer materials, solely from polymer materials without the inclusion of any metallic materials, or a combination of polymer and metallic materials.

In some embodiments, some or all of the wires of the cover 604 are DFT wires having a radiopaque core (e.g., platinum, tantalum, gold, tungsten, etc.) surrounded by a superelastic material (e.g., Nitinol, a cobalt-chromium alloy, etc.). The radiopaque core may comprise about 5% to about 50% (e.g., 10%, 15%, 20%, 25%, 30%, 35%, 40%, 45%) of the total-cross-sectional area of the individual wires. In some embodiments, the cover 200 may have 72-144 total wires (e.g., 72, 96 128, 144, etc.) Moreover, some or all of the wires may have a wire diameter of about 0.005 inches to about 0.015 inches (e.g., 0.008 inches, 0.01 inches, etc.). In some embodiments, all of the wires have the same diameter, and in other embodiments some of the wires have different diameters.

As shown in FIG. 6A, in some embodiments the cover 604 may have a proximal portion 620, an intermediate portion 632, and a distal portion 634. The proximal portion 620 may extend from the connector 605 to a proximal terminus of the intermediate portion 632, the intermediate portion 632 may extend from a distal terminus of the proximal portion 620 to a proximal terminus of the distal portion 634, and the distal portion 634 may extend from a distal terminus of the intermediate portion 632 to a distal terminus 611 of the cover 604. At least when the cover 604 is in an expanded, relaxed state (as shown in FIG. 6A), the inner layer 606 may have (a) a first cross-sectional dimension $IL_1$ at the proximal portion 620 of the cover 604, (b) an increasing second cross-sectional dimension $IL_2$ along the intermediate portion 632 of the cover 604, and (c) a third cross-sectional dimension $IL_3$ at the distal portion 634 of the cover 604 that is greater than the first cross-sectional dimension $IL_1$. In some embodiments, the first cross-sectional dimension $IL_1$ of the inner layer 606 is generally constant along the proximal portion 620 of the cover 604, and the third cross-sectional dimension $IL_3$ of the inner layer 606 is generally constant along the distal portion 634 of the cover 604.

FIG. 6B is an enlarged view of a portion of the cover 604 shown in FIG. 6A. As shown in FIG. 6B, in some embodiments the inner layer 606 is convex towards the cavity 610 along the intermediate portion 632. In some embodiments, the inner layer 606 is concave towards the cavity 610 along the intermediate portion 632. In some embodiments, the inner layer 606 has a proximal region 631 and a distal region 633 along the intermediate portion 632. As shown in FIG. 6B, in some embodiments, the proximal region 631 is convex towards the cavity 610, and the distal region 633 is concave towards the cavity 610. In some embodiments, the proximal region 631 is concave towards the cavity 610, and the distal region 633 is convex towards the cavity 610.

Referring again to FIG. 6A, at least when the cover 604 is in the expanded, relaxed state, the outer layer 608 of the cover 604 may have a first cross-sectional dimension $OL_1$ that is generally constant along the distal portion 634 and the intermediate portion 632 of the cover 604. The first cross-sectional dimension $OL_1$ of the outer layer 608 may be greater than an inner diameter of the portion of the blood vessel adjacent to the clot material such that, when the cover 604 is expanded within a portion of the blood vessel V (see FIG. 7), the outer layer 608 exerts a radially outward force on the blood vessel wall along at least the distal and intermediate portions 634, 632 of the cover 604. In some embodiments, at least when the cover 604 is in an expanded, relaxed state, the outer layer 608 along the proximal portion 620 of the cover 604 has a proximal region 622 and a distal region 624. As shown in FIG. 6A, the proximal region 622 may extend distally from the connector 605 to a proximal terminus of the distal region 624, and the distal region 624 may extend distally from a distal terminus of the proximal region 622 to a proximal terminus of the intermediate portion 620. In some embodiments, a cross-sectional dimension of the proximal region 622 decreases in a proximal direction, and the distal region 624 has a generally constant cross-sectional dimension. Moreover, the cross-sectional dimension of the distal region 624 may be substantially the same as the cross-sectional dimension along the distal and intermediate portions 632, 634 of the cover 604.

Figure 7:
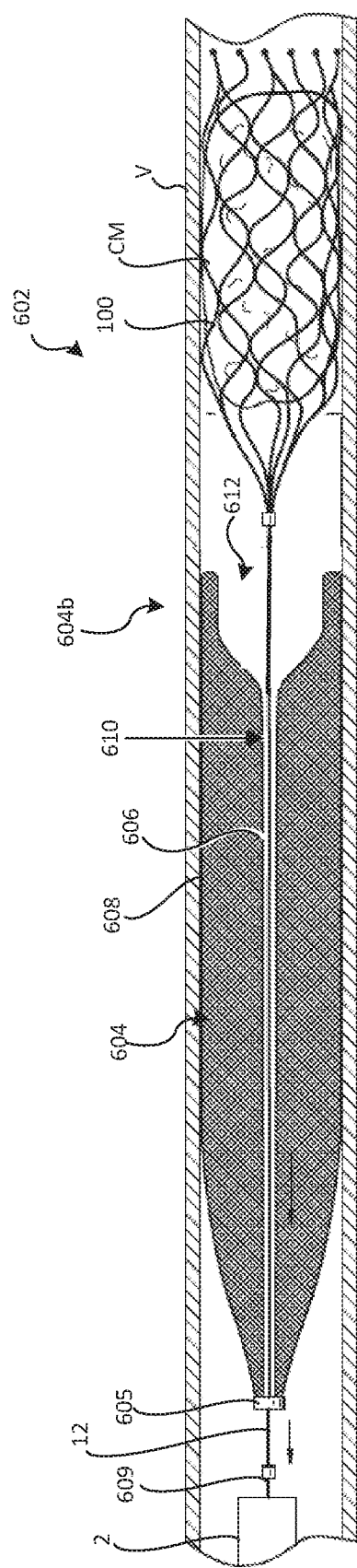
FIG. 7 is a side view of the clot retrieval device shown in FIG. 6A positioned in a blood vessel in an expanded state.

FIG. 7 is a side view of the retrieval assembly 602 positioned in a blood vessel V (e.g., a cerebral blood vessel) at a treatment site in an expanded state. In use, the retrieval assembly 602 may be delivered through a delivery catheter 2 (e.g., a microcatheter) to the treatment site as described above with reference to FIGS. 2A and 2B. The delivery catheter 2 may then be pulled proximally relative to the retrieval assembly 602 to release the capture structure 100, thereby allowing the capture structure 100 to self-expand within the clot material CM as described above with reference to FIG. 2C. The delivery catheter 2 may continue advancing proximally to release the cover 604 such that at least a portion of the outer layer 608 expands into contact with the wall of the blood vessel V.

With the capture structure 100 engaging the clot material CM, the elongated shaft 12 may be pulled proximally. Friction between the outer layer 608 and the vessel wall V holds the cover 604 in place within the blood vessel lumen and/or resists proximal movement to a greater degree than the capture structure 100. As such, the elongated shaft 12 slides proximally through the cavity 610 and connector 605 and pulls the capture structure 100 proximally through the opening 612 at the distal region 604b of the cover 604, as shown in FIG. 8A. As shown in FIG. 8B, as the capture structure 100 is pulled through the narrow cavity 610, the capture structure 100 forces the inner layer 806 radially outwardly along the portion of the inner layer 806 aligned with the capture structure 100. Once the capture structure 100 is completely within the cavity 610, the inner layer 606 collapses radially inwardly distal of a distal terminus 101 of the capture structure 100, thereby forming a narrowed or substantially or completely closed region 630 and enclosing the capture structure 100 within the inner layer 606. Such narrowing or closure of the region 630 helps prevent the escape of thrombus from the capture structure 100 and/or cover 604 during withdrawal of the device 600 from the blood vessel V.

Once the connector 605 abuts connector 607 and/or stop 609, proximal movement of the elongated shaft 12 pulls the cover 604 and the capture structure 100 proximally together. As shown in FIG. 8C, the clot retrieving device 600 may continue advancing proximally until the retrieval assembly 602 is positioned within the delivery catheter 2. The delivery catheter 2, device 600, and associated clot material CM may then be withdrawn from the patient.

The cover 604 of FIGS. 6A-8C can be easily retracted to the initial position shown in FIG. 6A to facilitate performing a second (and subsequent) "pass" to retrieve any thrombus that may remain in the treatment area following a first pass. After the first pass (see FIG. 8C), the cover 604 can be easily grasped, e.g. at the connector 605, and retracted proximally to the position shown in FIG. 6A by sliding it along the shaft 12. Because the cover 604 does not evert during the process of covering the capture structure 100, there is no need to reverse any eversion during retraction. This in turn allows for a simpler retraction process. Following retraction of the cover 604, the capture structure 100 can be cleaned of any thrombus and used in the second and subsequent passes.

3.0 SELECTED EMBODIMENTS OF CONNECTION ASSEMBLIES AND ASSOCIATED METHODS OF USE

FIGS. 9A-15 show various embodiments of connection assemblies for use with the clot retrieving devices of the present technology. Although the connection assemblies discussed below are described with reference to the clot retrieving device 10 shown in FIGS. 1A-2G, any of the connection assemblies may be used with any of the clot retrieving devices, capture structures, and/or covers disclosed herein. For example, any of the connection assemblies discussed below may be used with any of the covers discussed above with reference to FIGS. 3A-8C. Moreover, only the first end portion 200a of the cover 200 and proximal portion 100a of the capture structure 100 are shown in FIGS. 9A-15 for ease of illustration.

Figure 9A:
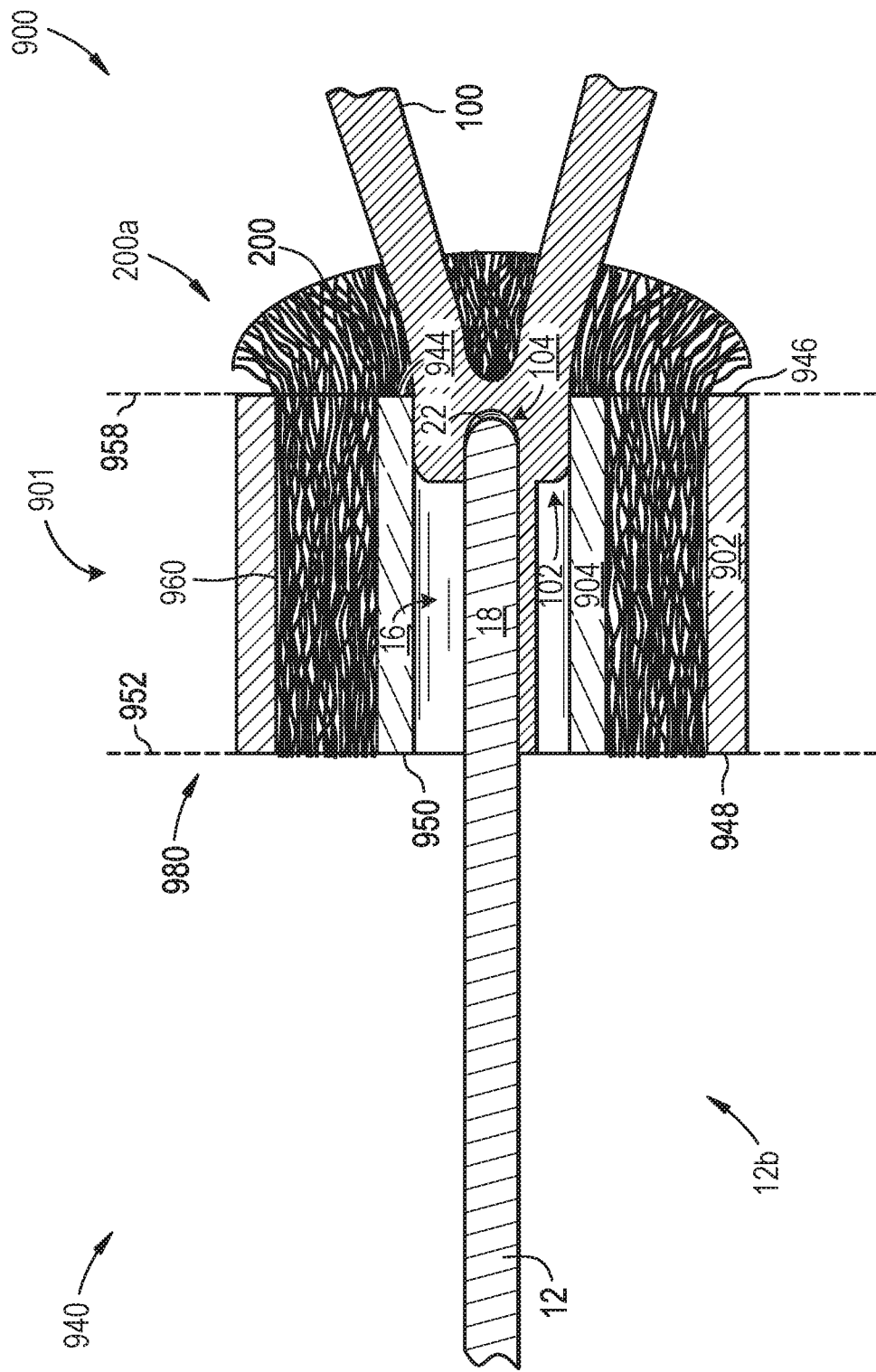
FIG. 9A is a cross-sectional side view of a distal portion of a clot retrieving device in accordance with some embodiments of the present technology.
Figure 9B:
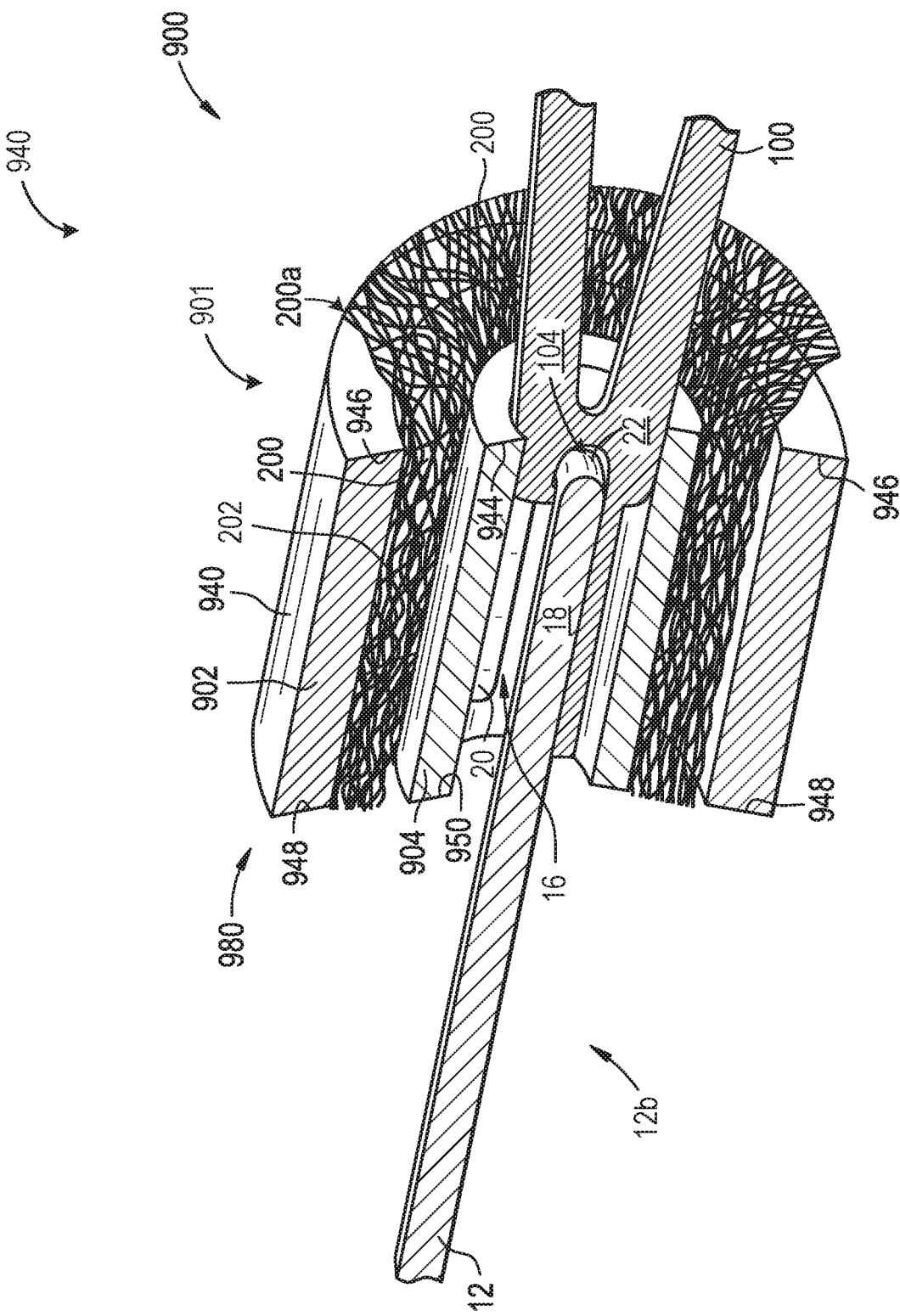
FIG. 9B is a cross-sectional isometric view of the distal portion of the clot retrieving device shown in FIG. 9A.

FIGS. 9A and 9B are side and isometric enlarged views, respectively, of one embodiment of a connection assembly 900 of a clot retrieving device 940 shown outside of a blood vessel in accordance with the present technology. The clot retrieving device 940 can include components that are generally similar in structure and function as those of the clot retrieving device 10 shown in FIGS. 1A-2G. For example, the clot retrieving device 940 includes the elongated shaft 12, the capture structure 100, and the cover 200. As such, common acts and structure are identified by the same reference numbers, and only significant differences in operation and structure are described below.

As shown in FIGS. 9A and 9B, in some embodiments of the clot retrieving device 940, the coupling region 102 of the capture structure 100 may include an opening 104, and a coupling region 16 of the shaft 12 may extend through the opening 104. For example, the coupling region 16 of the shaft 12 can include a first region 18, a second region 20 (only visible in FIG. 9B), and a bend 22 between the first and second regions 18 and 20. In some embodiments, the coupling region 16 can form a hook such that the elongated shaft 12 is bent back on itself (e.g., approximately 180 degrees) and the second region 20 of the shaft 12 is proximal of the bend 22 and the opening 104. In other embodiments, the capture structure 100 may be coupled to the shaft 12 via other connection means.

The connection assembly 900 may include a connector 901 that comprises an outer band 902 and an inner band 904. The inner band 904 is positioned around a portion of the elongated shaft 12, and the outer band 902 is located radially outwardly of the inner band 904. At least a portion of the outer band 902 may be axially aligned and/or overlap with at least a portion the length of the inner band 904. In some embodiments of the device in FIGS. 9A and 9B, the inner band 904 is positioned around the interconnected coupling regions 16 and 102 of the shaft 12 and the capture structure 100, respectively, and the first portion 200a of the cover 200 is between the inner band 904 and the outer band 902. For example, the first portion 200a of the cover can be clamped between the outer band 902 and the inner band 904, or otherwise adhered to the outer and inner bands 902, 904. As such, the outer and inner bands 902, 904 couple the cover 200 and the capture structure 100 to the shaft 12, and fix the first end portion 200a of the cover 200 and the proximal portion 100a of the capture structure 100 relative to one another and to relative to the elongated shaft 12. In some embodiments, the connector 901 may include more or fewer than two bands.

Each of the inner band 904 and the outer band 902 can be generally cylindrical, or the inner band 904 and/or the outer band 902 may have different shapes. The inner band 904 can have a cross-sectional dimension that is about 0.027 inches or less, about 0.021 inches or less, and/or about 0.015 inches or less. The outer band 902 can have a cross-sectional dimension that is greater than that of the inner band 904. The outer band 902 can have a cross-sectional dimension that is about 0.027 inches or less, 0.021 inches or less, and/or 0.015 inches or less.

The inner band 904 includes a proximal terminus 950, a distal terminus 944, and a length extending between the proximal terminus 950 and the distal terminus 944. Likewise, the outer band 902 includes a proximal terminus 948, a distal terminus 946, and a length extending between the proximal terminus 948 and the distal terminus 946. In some embodiments, the proximal terminus 950 of the inner band 904 defines the proximal terminus of the connector 901 (alone or in conjunction with the outer band 902) and/or the distal terminus 944 of the inner band 904 defines the distal terminus of the connector 901 (alone or in conjunction with the outer band 902). Likewise, in some embodiments, the proximal terminus 948 of the outer band 902 defines the proximal terminus of the connector 901 (alone or in conjunction with the inner band 904) and/or the distal terminus 946 of the outer band 902 defines the distal terminus of the connector 901 (alone or in conjunction with the inner band 904).

As shown in FIGS. 9A and 9B, the inner band 904 and the outer band 902 may have generally the same length, but the inner band 904 and the outer band 902 may have different lengths. In some embodiments, the proximal terminus 950 of the inner band 904 can be generally aligned with the proximal terminus 948 of the outer band 902 along a plane 952 approximately normal to the elongated shaft 12 such that the proximal terminus 950 of the inner band 904 and the proximal terminus 948 of the outer band 902 are within about 0.005 inches of each other. Likewise, the distal terminus 944 of the inner band 904 can be generally aligned with the distal terminus 946 of the outer band 902 along a plane 958 approximately normal to the elongated shaft 12 such that the distal terminus 944 of the inner band 904 and the distal terminus 946 of the outer band 902 are within about 0.005 inches of each other.

In some embodiments the outer and inner bands 902, 904 are generally coextensive along their entire respective lengths, but the outer and inner bands 902, 904 may be offset along the longitudinal axis of the device 10 and/or may have different lengths such that the outer and inner bands 902, 904 are generally coextensive along only a portion of one or both of their respective lengths.

In some embodiments, the inner band 904 and/or outer band 902 can include a radiopaque material such as platinum, gold, tungsten, tantalum, platinum-iridium, and/or alloys of any of the foregoing materials. As such, the inner band 904 and/or outer band 902 may improve visualization of the retrieval assembly 14. For example, visualization of the connector 901 can assist the physician in confirming the location of the retrieval assembly 14, or more specifically, the capture structure 100, which may be distal to or generally aligned with the inner band 904 and/or outer band 902.

The connector 901 may be secured to the capture structure 100 and elongated shaft 12 by a crimp and/or a binding agent. For example, the inner band 904 may be secured to the capture structure 100 and/or the elongated shaft 12 by a crimp and/or a binding agent to fixedly attach the inner band 904 to the elongated shaft 12. Moreover, the outer band 902 may be secured to the first end portion 200a of the cover 200 by a crimp and/or a binding agent to fixedly attach the outer band 902 and the first end portion 200a of the cover 200 to the inner band 904, elongated shaft 12, and/or capture structure 100. Suitable binding agents include an adhesive, solder, welding flux, brazing filler, or other materials known and/or used in the art.

In some embodiments, the outer band 902, cover 200, and inner band 904 are not fixed at a single location along the elongated shaft 12, but instead are configured to rotate and/or translate along or relative to the elongated shaft 12. In these embodiments, the clot retrieving device 10 may include one or more stops (e.g., coils, bumpers, bands, second connectors, etc.) fixed at one or more locations along the elongated shaft 12 proximal and/or distal to the connector 901, thereby restricting axial movement of connector 901 (and associated first end portion 200a of the cover 200 and proximal portion 100a of the capture structure 100) to a predetermined length of the elongated shaft 12. An example of one such embodiment is described in further detail below with respect to FIGS. 12A-15.

The ability of the retrieval assembly 14 (e.g., the cover 200, capture structure 100, and connector 901) to rotate may be advantageous to relieve at least some of the tortious stress built up during the delivery of the clot retrieving device 10 through the vasculature. As previously described, the device 10 is often advanced from a remote part of the body and into the cerebral region of the vasculature. Along this path to a patient's treatment site, the device 10 may undergo many twists and turns that result in tortious stress being exerted on the device 10. Such tortional stress can create difficulty when the device 10 deploys from a retracted state to an expanded state. The ability to rotate with respect to the elongated shaft 12 can help relieve these stresses and improve control over deployment and positioning of the retrieval assembly 14.

The connector 901 can be assembled directly over the elongated shaft 12 or over a sacrificial wire or tool. When the connector 901 is formed over the elongated shaft 12, the outer band 902, cover 200, and inner band 904 can be positioned sequentially over the elongated shaft 12 (e.g., the outer band 902 first, then the cover 200, then the inner band 904). This can wedge the first end portion 200a of the cover 200 between the outer band 902 and the inner band 904. The first end portion 200a of the cover 200 thus presses outwardly against both the inner band 904 and outer band 902, thereby creating a surface friction between (a) the cover 200 and (b) the outer surface of the inner band 904 and inner surface of the outer band 902 that is sufficient to secure the cover 200 between the inner and outer bands 904 and 902.

When the connector 901 is formed over a sacrificial wire or tool, the outer band 902, cover 200, and inner band 904 can be positioned sequentially (e.g., the outer band 902 first, then the cover 200, then the inner band 904) over a sacrificial wire having a larger outer diameter than that of the elongated shaft 12 that the connector 980 is intended to be later inserted over. Once the outer band 902, cover 200, and inner band 904 are correctly positioned over the sacrificial wire, the outer band 902, cover 200, and inner band 904 can be, for example, crimped together and the sacrificial wire can be removed. The outer band 902, cover 200, and inner band 904 can then be slideably positioned over the elongated shaft 12. In such an embodiment, the outer band 902, cover 200, and inner band 904 may not be secured to the elongated shaft 12 and can be configured to move with respect to the elongated shaft 12, as previously described. Assembly of the connector 901 over a sacrificial wire, tool or mandrel in this manner allows for the connector 901 and cover 200 to be constructed separately from the shaft 12 and capture structure 100, and subsequent joining of the connector 901 and cover 200 to the shaft in a separate manufacturing step or location. This in turn offers flexibility and efficiency in the manufacture of the retrieval device.

Once the connector 901 is assembled over the elongated shaft 12 or sacrificial wire or tool, the cover 200 may have wires 960 (e.g., filaments) that protrude from the proximal terminus of the connector 901. The protruding wires 960 can be trimmed to be generally aligned with the plane 952 extending along the proximal terminus of the connector 901. As such, the wires 960 can be trimmed to not protrude, or to protrude less, from the proximal terminus of the connector 901.

Figure 10:
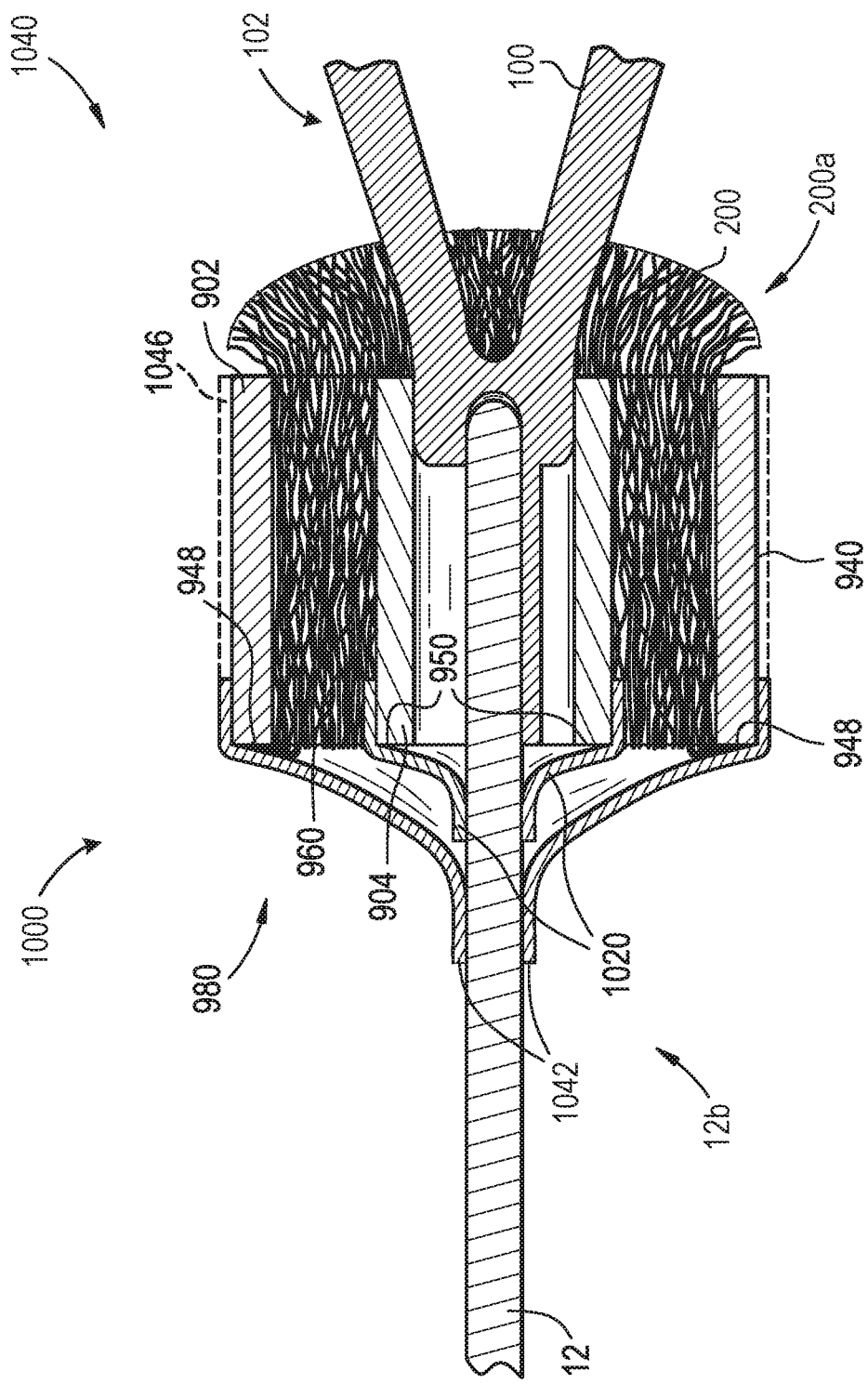
FIGS. 10 and 11 are cross-sectional side views of the distal portion of a clot retrieving device in accordance with some embodiments of the present technology.

FIG. 10 is a cross-sectional side view of some embodiments of a clot retrieving device 1040 having a connection assembly 1000 configured in accordance with the present technology. The connection assembly 1000 can include components that are generally similar in structure and function as those of the connection assembly 900 in FIGS. 9A and 9B. For example, the connection assembly 1000 includes the connector 901, the outer band 902, and the inner band 904 of the connection assembly 900, and all variations of the foregoing as described above. As such, common acts and structure are identified by the same reference numbers, and only significant differences in operation and structure are described below.

Figure 11:
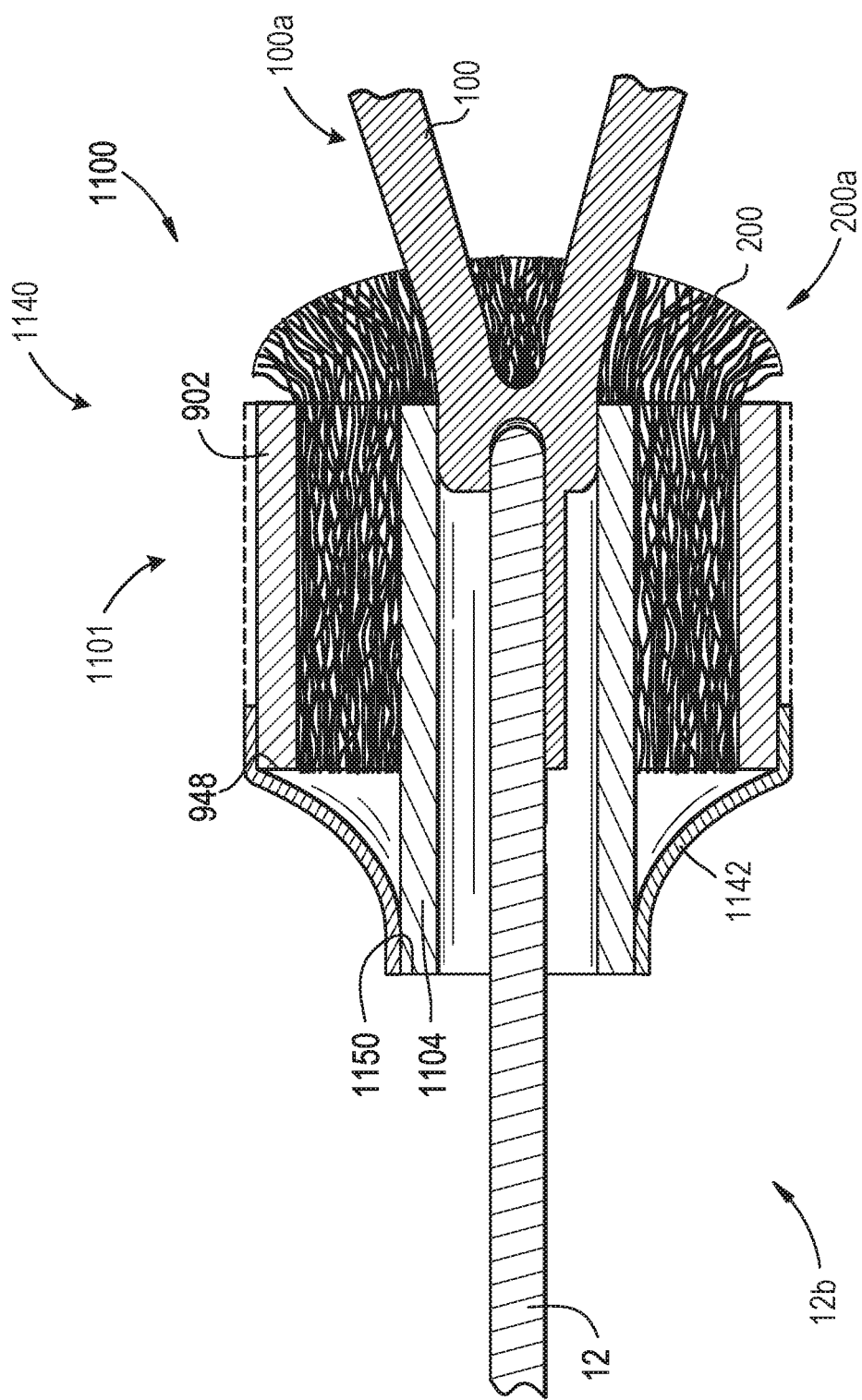

The connection assembly 1000 shown in FIG. 10 includes first and second jackets 1020 and 1042 at a proximal portion of the connector 901. The first jacket 1020 (e.g., an inner sleeve) may be positioned over a proximal terminus 950 of the inner band 904 and a portion of the elongated shaft 12 proximal of the inner band 904. The second jacket 1042 (e.g., an outer sleeve) may be positioned over a proximal terminus 948 of the outer band 902 and the elongated shaft 12 proximal of the outer band 902. As such, the second jacket 1042 is positioned radially outwardly of the first jacket 1020. In some embodiments, the connection assembly 1000 may include only the first jacket 1020, or only the second jacket 1042 (for example, as shown in FIG. 11).

As shown in FIG. 10, the proximal portion of the second jacket 1042 directly contacts and is fixed to the elongated shaft 12, and the proximal portion of the first jacket 1020 directly contacts and is fixed to the elongated shaft 12 at a position distal of the fixed portion of the second jacket 1042. The second jacket 1042 may extend along all (see 1046) or a portion of the outer surface of the outer band 902. Likewise, the first jacket 1020 may extend along all or a portion of the inner band 904. In some embodiments, the first and/or second jackets 1020 and 1042 may be indirectly coupled to the shaft 12 via an intermediate structure. For example, in some embodiments, the proximal portion of the first jacket 1020 is adhered to and in direct contact with the shaft 12 and the proximal portion of the second jacket 1042 is adhered to and in direct contact with the proximal portion of the first jacket 1020. In such embodiments, the proximal portion of the first jacket 1020 is positioned between the elongated shaft 12 and the proximal portion of the second jacket 1042 does not directly contact the elongated shaft 12.

The first and/or second jackets 1020 and 1042 can include a polymer material, including fluoropolymers such as polytetrafluoroethylene (PTFE). The first and/or second jackets 1020 and 1042 can also include polyimide, polyether ether ketone (PEEK), polyurethane, nylon, polyethylene, polyamide, or combinations thereof. The first and/or second jackets 1020 and 1042 may also include elastic materials such as any heat-shrinkable material including but not limited to Pebax, polyurethane, silicone, and/or polyisoprene. When a heat-shrinkable material is used, the heat-shrinkable material can be applied over the device and heated such that the heat-shrinkable material is thermally bonded and compressed to adhere to the exterior of the inner and outer bands 904 and 902 and the elongated shaft 12. The jacket(s) can take the form of a mass of adhesive, solder or other solidified liquid (rather than a pre-existing sheet, tube or other body of solid material) that is applied to the proximal terminus of the band(s) 902 and/or 904 so as to cover the wire ends.

As shown in FIG. 10, the first and/or second jackets 1020, 1042 may be advantageous for providing a smooth or otherwise atraumatic surface at the proximal edge of the connector 901. For example, in some embodiments, the cover 200 is composed of a plurality of wires and at least some of the wires protrude proximally from the proximal terminus 948 of the outer band 902. The second jacket 1042 covers the protruding ends of the wires to prevent the protruding ends from catching on the cover wall 200c (FIGS. 1A and 1B) as the cover wall 200c advances over the connector 980 while it inverts over the capture structure 100 and also to prevent trauma to the vessel walls.

FIG. 11 is a cross-sectional side view of clot retrieving device 1140 having a connection assembly 1100 in accordance with the present technology. The connection assembly 1100 can include components that are generally similar in structure and function as those of the connection assemblies 900 and 1000. For example, the connection assembly 1100 can include the outer band 902 that is generally similar to that discussed above with reference to FIGS. 9A and 9B. As such, common acts and structure are identified by the same reference numbers, and only significant differences in operation and structure are described below.

As shown in FIG. 11, the connection assembly 1100 includes a connector 1101 comprising the outer band 902, an inner band 1104 having a proximal terminus 1150 extending proximally beyond the proximal terminus 948 of the outer band 902, and a jacket 1142 extending between the outer band 902 and the inner band 1104. The inner band 1104 is generally similar to the inner band 904 described above with respect to FIGS. 9A and 9B, except the inner band 1104 has a length that is greater than that of the outer band 902 and extends proximally beyond the distal terminus 946 of the outer band 902. In addition, the jacket 1142 can be generally similar to the second jacket 1042 described above with respect to FIG. 10, except the jacket 1142 has a proximal portion adhered to an outer surface of the inner band 1104.

The connector 1101 shown in FIG. 11 may be configured to rotate about the longitudinal axis of the shaft 12 and/or translate along the length of the elongated shaft 12. In other embodiments, the connector 1101 may be secured to the elongated shaft 12 by a crimp and is not configured to move with respect to the elongated shaft 12.

Figure 12A:
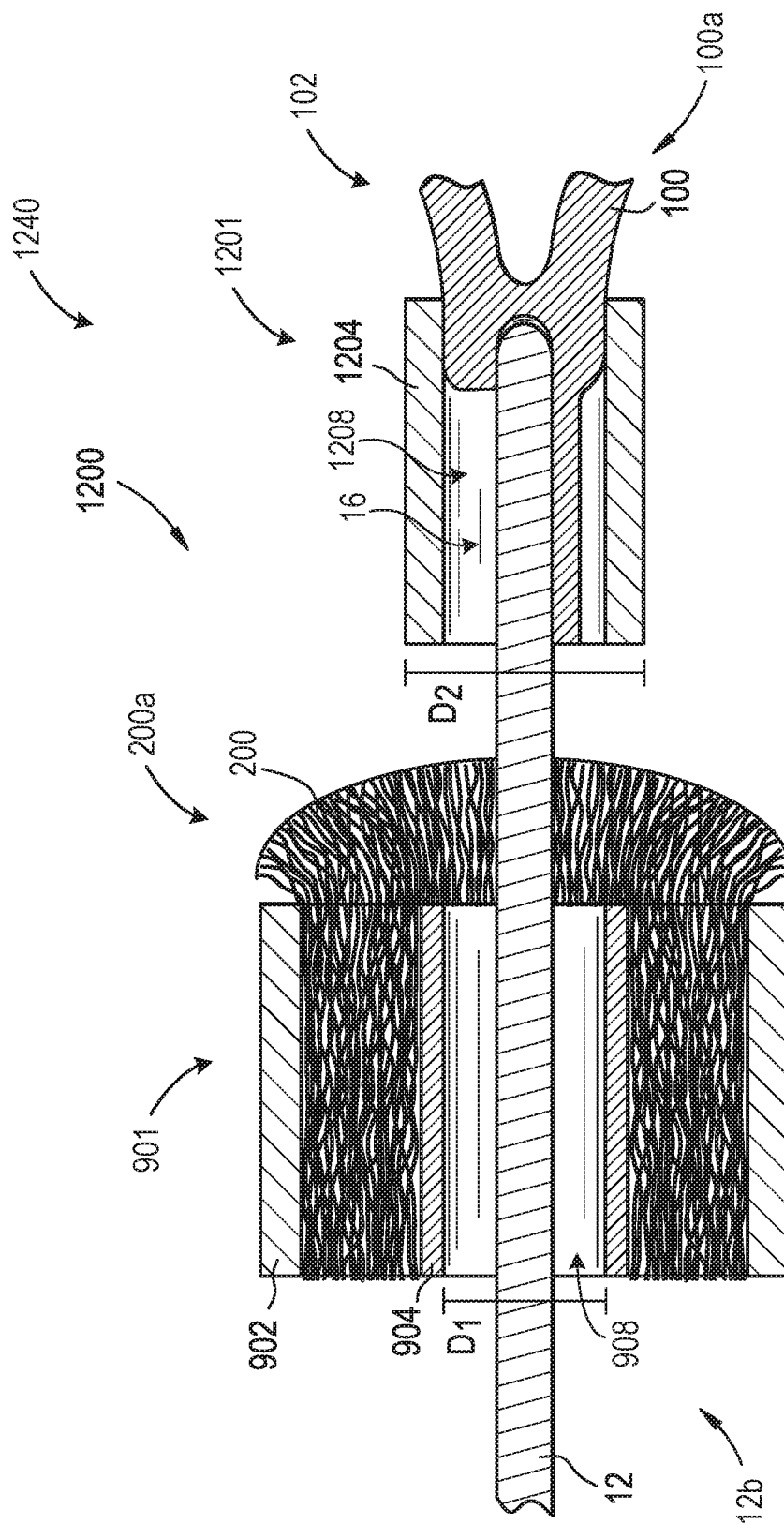
FIG. 12A is a cross-sectional side view of a distal portion of a clot retrieving device in accordance with some embodiments of the present technology.
Figure 12B:
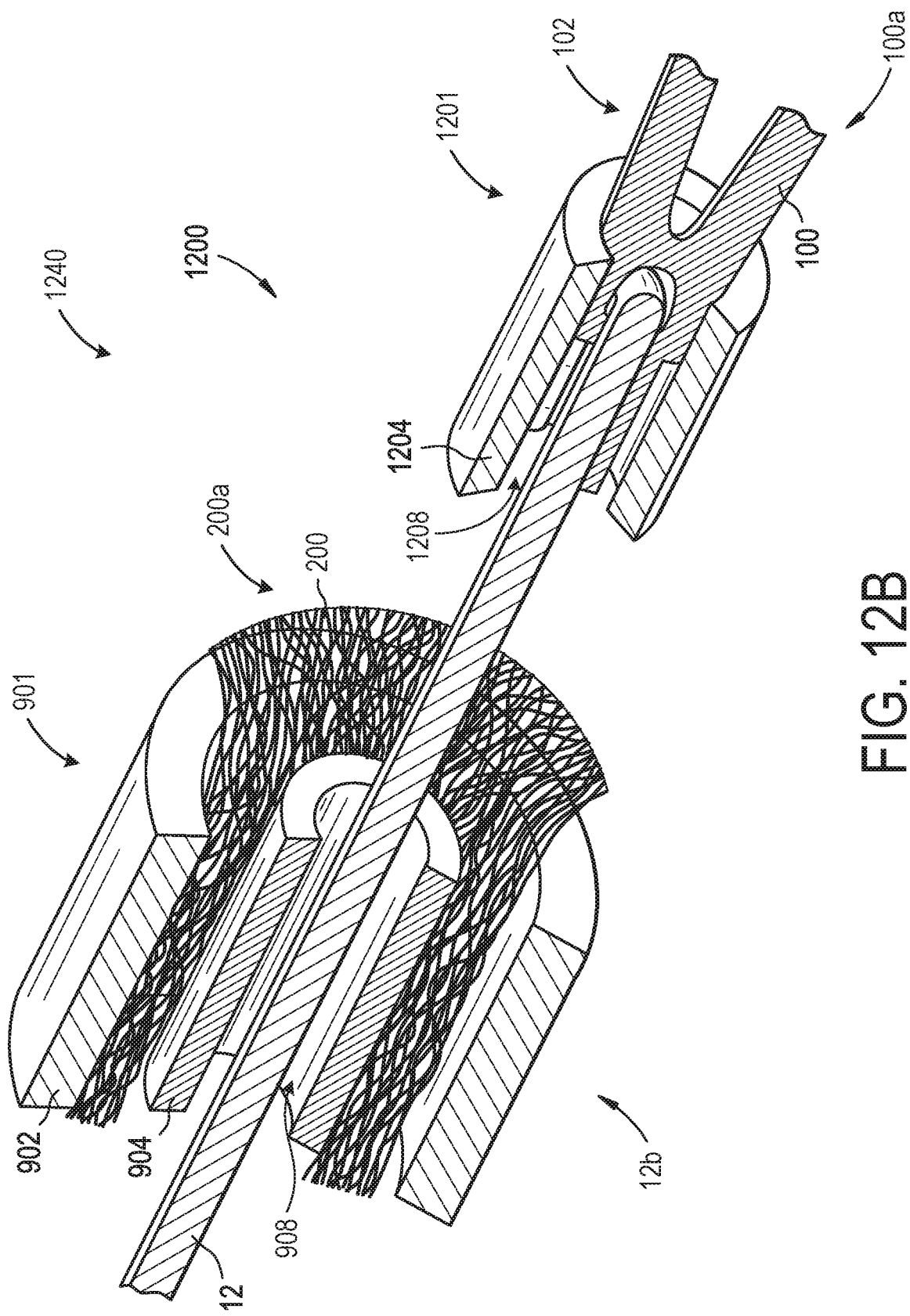
FIG. 12B is a cross-sectional isometric view of the distal portion of the clot retrieving device shown in FIG. 12A.

FIGS. 12A and 12B are cross-sectional side and isometric views of some embodiments of a clot retrieving device 1240 having a connection assembly 1200 in accordance with the present technology. The connection assembly 1200 can include components that are generally similar in structure and function as those of the connection assembly 900 in FIGS. 9A and 9B. For example, the connection assembly 1200 can include the connector 901 having the outer band 902 and the inner band 904 that are generally similar to those discussed above with reference to FIGS. 9A and 9B. As such, common acts and structure are identified by the same reference numbers, and only significant differences in operation and structure are described below. For example, in addition to the connector 901 (referred to with respect to FIGS. 12A and 12B as "the first connector 901"), the connection assembly 1200 may include a second connector 1201 coupled to the elongated shaft 12 distal of and spaced apart from the first connector 901. In other embodiments, the first connector 901 may abut or otherwise be adjacent to and in contact with the second connector 1201. Unlike connection assembly 900, the first connector 901 couples only the cover 200 (and not the capture structure 100) to the elongated shaft 12, while the second connector 1201 couples the capture structure 100 to the shaft 12.

The second connector 1201 may comprise a single band 1204 similar to any of the bands 902, 904, and 1104 described above with reference to FIGS. 9A-11. For example, the band 1204 may have a generally cylindrical sidewall that defines a lumen 1208 therethrough. In some embodiments, the second connector 1201 and/or band 1204 may include a radiopaque material to improve visualization of the band 1204 and/or position of the proximal region 100a of the capture structure 100. In other embodiments, the band 1204 may have different shapes or components. Moreover, in some embodiments, the connector 1201 may include more than one band. For example, in some embodiments the connector 1201 may include an outer band surrounding at least a portion of the band 1204.

In the embodiment shown in FIGS. 12A and 12B, the shaft 12 extends through a channel 908 defined by an interior surface of the inner band 904 of the first connector 901, and the second connector 1201 and/or band 1204 is positioned around the interconnected coupling regions 16 and 102 of the shaft 12 and the capture structure 100, respectively. As such, the second connector 1201 fixes the proximal portion 100a of the capture structure 100 to the elongated shaft 12. For example, the second connector 1201 and/or band 1204 can be secured to the capture structure 100 and/or the elongated shaft 12 by a crimp and/or a binding agent. The binding agent may fill any void within the lumen 1208 of the band 1204 and bond the second connector 1201 and/or band 1204 to the capture structure 100 and/or the elongated shaft 12.

In some embodiments, the elongated shaft 12 is slidably received through the channel 908 such that the connector 901 (and associated cover 200) is movable axially along the shaft 12 and/or free to rotate about the shaft 12. At least in these embodiments, the second connector 1201 can have an outer diameter D2 greater than an inner diameter D1 of the inner band 904. In such an embodiment, the second connector 1201 may serve as a mechanical stop and prevent the second connector 1201 from moving proximal of the first connector 901. In other embodiments, the first connector 901 is crimped or otherwise fixed to the shaft 12 such that the first connector 901 is not free to move axially and/or rotate.

Figure 13:
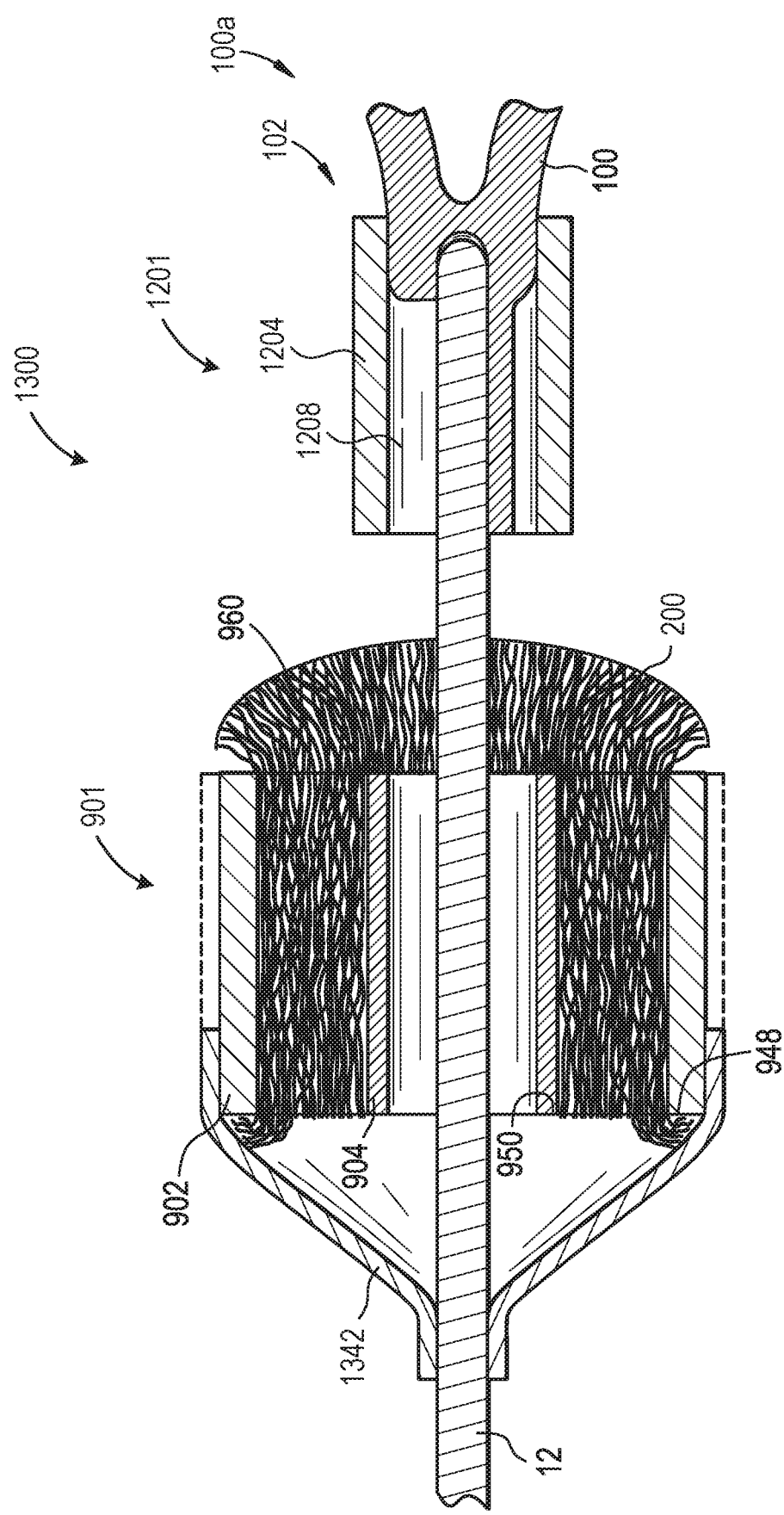
FIGS. 13-15 are cross-sectional side views of the distal portion of a clot retrieving device in accordance with some embodiments of the present technology.

FIG. 13 is a cross-sectional side view of some embodiments of a clot retrieving device 1340 having a connection assembly 1300 configured in accordance with present technology. The connection assembly 1300 can include components that are generally similar in structure and function as those of the connection assembly 1200 in FIGS. 12A and 12B. For example, the connection assembly 1300 includes the first connector 901 and the second connector 1201 that are generally similar to those discussed above with reference to FIGS. 9A, 9B, 12A and 12B. As such, common acts and structure are identified by the same reference numbers, and only significant differences in operation and structure are described below. For example, the connection assembly 1300 shown in FIG. 13 includes a jacket 1342 (e.g., an outer sleeve) positioned extending between the proximal terminus 948 of the outer band 902 and a portion of the elongated shaft 12 proximal of the outer band 902. In some embodiments, the connection assembly 1300 may include more than one jacket (e.g., two jackets, three jackets, etc.). For example, in some embodiments the connection assembly 1300 may include a jacket extending proximally from the inner band 904 (such as jacket 1020 shown in FIG. 10) to the shaft 12. The jacket 1342 may include any of the materials discussed above with reference to jackets 1020 and 1042. As shown in FIG. 13, the proximal portion of the jacket 1342 directly contacts and is fixed to the elongated shaft 12, but alternatively the jacket 1342 may be indirectly coupled to the shaft 12 via an intermediate structure (not shown) such that the proximal portion of the jacket 1342 does not directly contact the elongated shaft 12. The jacket 1342 may extend along all (shown schematically in hashed lines) or a portion of the outer surface of the outer band 902.

Figure 14:
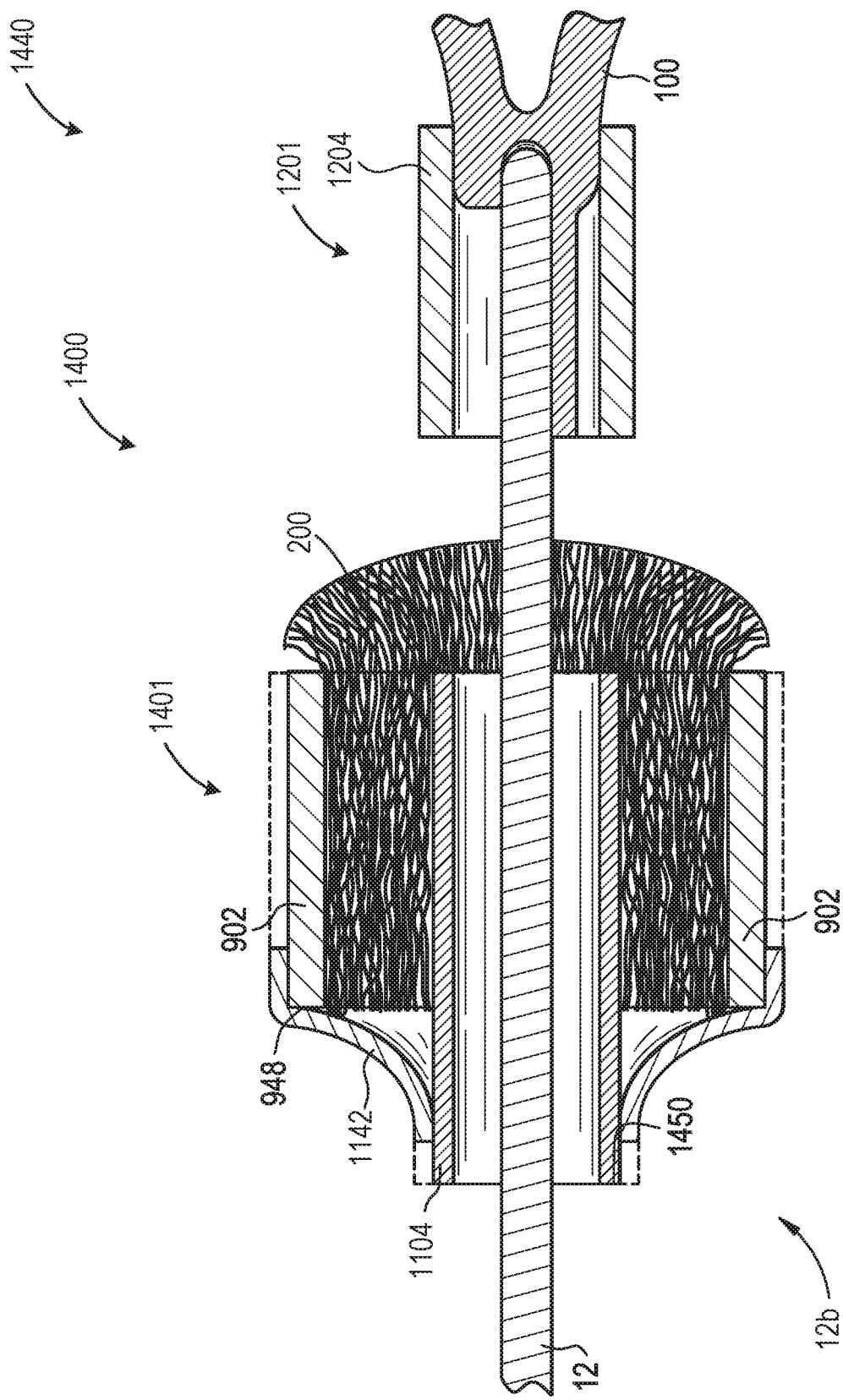

Some embodiments of a connection assembly 1400 and clot retrieving device 1440 in accordance with the present technology are shown in the cross-sectional side view of FIG. 14. The connection assembly 1400 may include the connection assembly 1100 of FIG. 11, as well as the connector 1201 of FIGS. 12A and 12B. For example, the connection assembly 1400 includes a connector 1401 comprising the outer band 902 and the inner band 1104. The inner band 1104 may have a proximal terminus 1450 extending proximally beyond the proximal terminus 948 of the outer band 902. The connection assembly 1400 further includes a jacket 1142 extending between the outer band 902 and the inner band 1104. In some embodiments, the connector 1401 shown in FIG. 14 may be configured to rotate about the longitudinal axis of the shaft 12 and/or translate along the length of the elongated shaft 12, or alternatively the connector 1401 may be secured to the elongated shaft 12 by a crimp and is not configured to move with respect to the elongated shaft 12.

Figure 15:
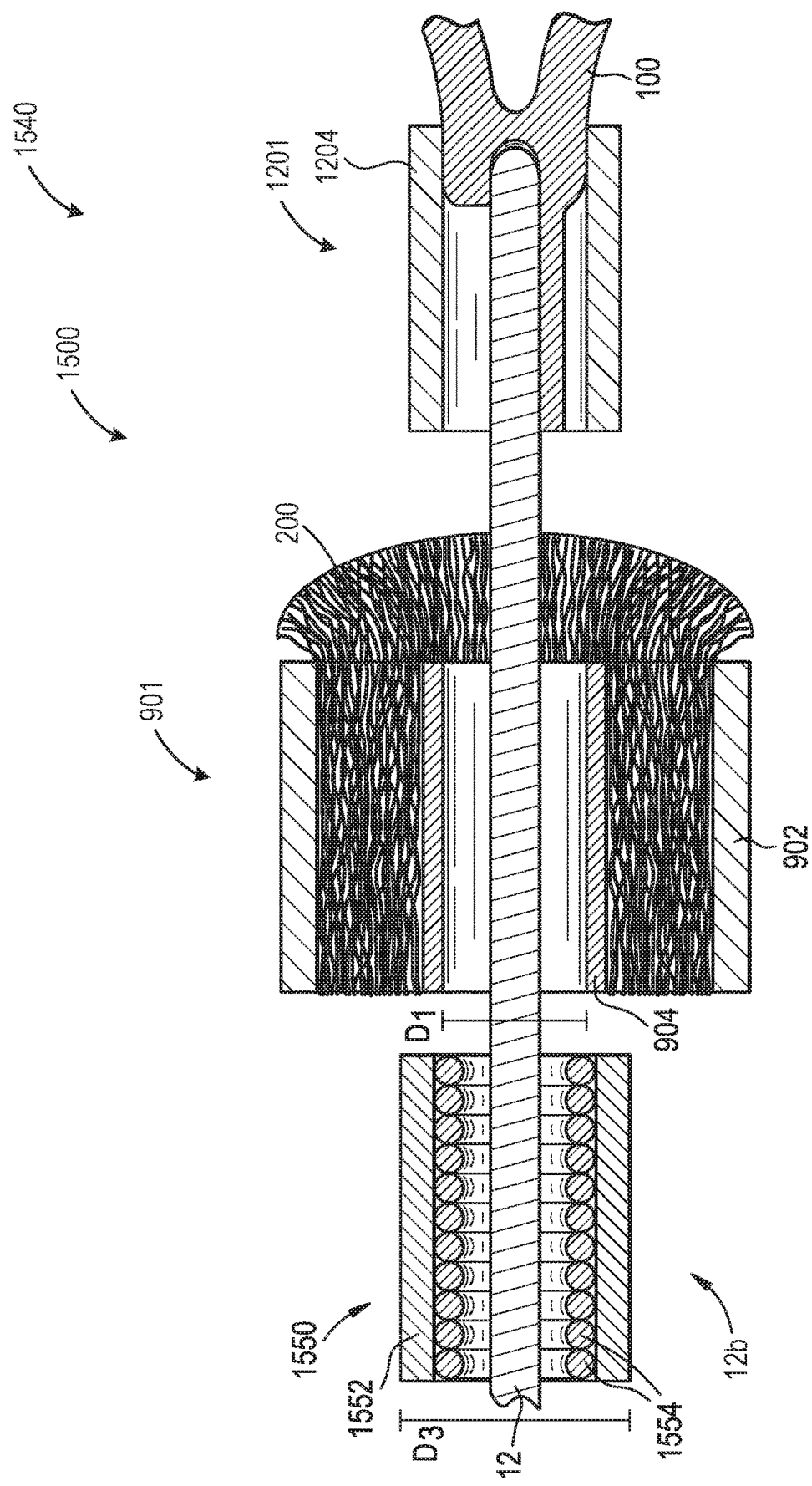

FIG. 15 is a cross-sectional side view of a connection assembly 1500 configured in accordance with some embodiments of the present technology. The connection assembly 1500 can include components that are generally similar in structure and function as those of the connection assembly 1200 in FIGS. 12A and 12B. For example, the connection assembly 1500 includes the first connector 901 and the second connector 1201 discussed above with reference to FIGS. 12A and 12B. The connection assembly 1500 may further include a stop 1550 (e.g., a bumper, band or coil) fixed to the elongated shaft 12 and proximal of the connector 901. The stop 1550 can include an outer sleeve 1552 surrounding a coil 1554 positioned around the elongated shaft 12. In some embodiments, such as those embodiments wherein the connector 901 is configured to move axially along the elongated shaft 12, it may be desired for the outer diameter D3 of the stop 1550 to be less than the outer diameter D1 of the inner band 904. In such an embodiment, the stop 1550 prevents the connector 901 from moving proximally past the stop 1550. The stop 1550 and/or the coil 1554 may also serve as a marker and include a radiopaque material. The coil 1554 may be formed of a metal and/or polymer material, and the sleeve 1552 may be a metal band crimped around the coil 1554 and/or a polymer material that shrinks when heated. The stop 1550 also provides mechanical support to the elongated shaft 12 over its length. As such, a particular length, diameter, and pitch of the stop 1550 can be selected to provide a desired flexibility/rigidity to the elongated shaft 12.

4.0 CONCLUSION

This disclosure is not intended to be exhaustive or to limit the present technology to the precise forms disclosed herein. Although specific embodiments are disclosed herein for illustrative purposes, various equivalent modifications are possible without deviating from the present technology, as those of ordinary skill in the relevant art will recognize. In some cases, well-known structures and functions have not been shown and/or described in detail to avoid unnecessarily obscuring the description of the embodiments of the present technology. Although steps of methods may be presented herein in a particular order, in alternative embodiments the steps may have another suitable order. Similarly, certain aspects of the present technology disclosed in the context of particular embodiments can be combined or eliminated in other embodiments. Furthermore, while advantages associated with certain embodiments may have been disclosed in the context of those embodiments, other embodiments can also exhibit such advantages, and not all embodiments need necessarily exhibit such advantages or other advantages disclosed herein to fall within the scope of the present technology. Accordingly, this disclosure and associated technology can encompass other embodiments not expressly shown and/or described herein.

Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "comprising" and the like are used throughout this disclosure to mean including at least the recited feature(s) such that any greater number of the same feature(s) and/or one or more additional types of features are not precluded. Directional terms, such as "upper," "lower," "front," "back," "vertical," and "horizontal," may be used herein to express and clarify the relationship between various elements. It should be understood that such terms do not denote absolute orientation. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments.

We claim:

1. A device for retrieving clot material from a blood vessel lumen, the device comprising:
    an elongated shaft having a distal zone;
    a capture structure having a proximal region coupled to the distal zone of the elongated shaft;
    a cover including a plurality of filaments, the cover having a first portion coupled to the distal zone of the elongated shaft and a free second portion, the cover having a first position in which the second portion extends proximally from the first portion, and a second position inverted relative to the first position in which the second portion extends distally from the first portion such that the cover at least partially surrounds the capture structure;
    a connector coupling the first portion of the cover to the distal zone of the elongated shaft, wherein at least a portion of the filaments protrude proximally from a proximal terminus of the connector and is radially aligned with or inward of an outer surface of the connector; and
    a jacket at least partially over the proximal terminus of the connector and the protruding portion of the filaments, wherein the jacket prevents direct contact between the cover and the protruding portions of the filaments as the cover moves from the first position to the second position.

2. The device of claim 1 wherein the cover is a braid, and the capture structure is a stent.

3. The device of claim 1 wherein the jacket includes a polymer.

4. The device of claim 1 wherein the jacket includes a heat-shrinkable material.

5. The device of claim 1 wherein the jacket is at least partially over a portion of the elongated shaft proximal of the proximal terminus of the connector.

6. The device of claim 1 wherein the inner band at least partially surrounds the proximal region of the capture structure.

7. The device of claim 1 wherein the connector is a first connector, and the device further comprises a second connector distal of the first connector along the elongated shaft, wherein the second connector at least partially surrounds the proximal region of the capture structure and the distal zone of the elongated shaft.

8. The device of claim 7 wherein the first connector is configured to move with respect to the elongated shaft.

9. The device of claim 8, further comprising a stop fixed to the elongated shaft proximal of the first connector.

10. The device of claim 1 wherein the connector includes an inner band and an outer band, and wherein:
the inner band at least partially surrounds a portion of the distal zone of the elongated shaft,
the outer band at least partially surrounds the inner band, and
the first portion of the cover is secured between the inner band and the outer band.

11. The device of claim 10 wherein the portion of the elongated shaft is a first portion, and the device further comprises a buffer material positioned over a second portion of the elongated shaft proximal of the proximal terminus of the inner band.

12. The device of claim 1 wherein the connector is fixed relative to the elongated shaft via the jacket.

13. A device for retrieving clot material from a blood vessel lumen, the device comprising:
an interventional element;
a manipulation member having a distal zone;
a cover having a first portion coupled to the distal zone of the manipulation member and a free second portion, the cover having a first position in which the second portion extends proximally from the first portion, and a second position inverted relative to the first position in which the second portion extends distally from the first portion such that the cover surrounds at least a portion of the interventional element;
a connector coupling the first portion of the cover to the distal zone of the manipulation member, wherein at least a portion of the cover extends proximally from a proximal terminus of the connector and is radially aligned with or inward of an outer surface of the connector; and
a jacket extending from the proximal terminus of the connector and covering the extending portion of the cover, thereby preventing the extending portion of the cover from engaging the remaining portion of the cover as the cover moves from the first position to the second position.

14. The device of claim 13 wherein the interventional element includes a proximal region at least partially surrounded by the connector.

15. The device of claim 13 wherein the connector includes an inner band and an outer band, and wherein the jacket is an outer sleeve, the device further comprising an inner sleeve over a proximal terminus of the inner band and a portion of the manipulation member proximal of the proximal terminus of the inner band.

16. The device of claim 13 wherein the connector is a first connector, the device further comprising a second connector at least partially surrounding the proximal region of the interventional element and the portion of the distal zone of the manipulation member.

17. The device of claim 13 wherein the connector includes an inner band and an outer band, and wherein the inner band is proximal of the proximal region of the interventional element and at least partially surrounds a portion of the distal zone of the manipulation member, and the outer band at least partially surrounds the inner band.

18. The device of claim 17 wherein a proximal terminus of the inner band extends proximally beyond a proximal terminus of the outer band, and wherein the jacket is at least partially over the inner band proximal of the proximal terminus of the outer band.

19. The device of claim 17 wherein the inner band and the outer band are configured to move with respect to the manipulation member.

20. The device of claim 13, further comprising a stop fixed to the manipulation member proximal of the connector.

21. The device of claim 16 wherein:
the interventional element includes an elongated proximal region and an opening extending laterally through the proximal region, and
the manipulation member includes a coupling element at the distal zone of the manipulation member, wherein at least a portion of the coupling element extends through the opening of the interventional element.

22. A method for retrieving clot material from a treatment site within a blood vessel lumen, the method comprising:
providing a clot retrieving device including an elongated shaft having a distal zone and a retrieval assembly at the distal zone, the retrieval assembly having:
a capture structure with a proximal region coupled to the distal zone of the elongated shaft,
a cover having a plurality of filaments, a first portion coupled to the distal zone of the elongated shaft and a free second portion, the cover having a first position in which the second portion extends proximally from the first portion, and a second position inverted relative to the first position in which the second portion extends distally from the first portion such that the cover at least partially surrounds the capture structure,
a connector coupling the first portion of the cover to the distal zone of the elongated shaft, wherein at least a portion of the filaments protrudes proximally from a proximal terminus of the connector and is radially inward of or substantially even with an outer surface of the connector, and
a jacket at least partially over the proximal terminus of the connector and the protruding portion of the filaments;
intravascularly advancing the clot retrieving device within a delivery catheter to the treatment site such that the retrieval assembly is positioned proximate the clot material at the treatment site;
deploying the retrieval assembly within the blood vessel lumen such that the retrieval assembly expands to the first position; and
withdrawing the retrieval assembly proximally through the delivery catheter to remove clot material from the treatment site.

23. The method of claim 22 wherein the connector at least partially surrounds the proximal region of the capture structure.

24. The method of claim 22 wherein the connector is a first connector proximal of the proximal region of the capture structure, and the device further comprises a second connector at least partially surrounding the proximal region of the capture structure.

25. The method of claim 22 wherein the jacket is at least partially over a portion of the elongated shaft proximal of the proximal terminus of the connector.

26. The method of claim 22 wherein the connector includes an inner band and an outer band, wherein:
- the inner band at least partially surrounds a portion of the distal zone of the elongated shaft,
- the outer band at least partially surrounds the inner band, and
- the first portion of the cover is secured between the inner band and the outer band.

* * * * *

UNITED STATES PATENT AND TRADEMARK OFFICE
CERTIFICATE OF CORRECTION

PATENT NO. : 10,722,257 B2
APPLICATION NO. : 15/594449
DATED : July 28, 2020
INVENTOR(S) : Skillrud et al.

Page 1 of 1

It is certified that error appears in the above-identified patent and that said Letters Patent is hereby corrected as shown below:

In the Claims

In Column 38, in Claim 1, Line 52, delete "protrude" and insert -- protrudes --, therefor.

Signed and Sealed this
Twenty-second Day of September, 2020

Andrei Iancu
*Director of the United States Patent and Trademark Office*